(12) United States Patent
Melker et al.

(10) Patent No.: US 8,755,857 B2
(45) Date of Patent: *Jun. 17, 2014

(54) OPTIMIZED GAS SUPPLY USING PHOTOPLETHYSMOGRAPHY

(75) Inventors: Richard J. Melker, Gainesville, FL (US); A. Joseph Layon, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 1992 days.

This patent is subject to a terminal disclaimer.

(21) Appl. No.: 11/535,295

(22) Filed: Sep. 26, 2006

(65) Prior Publication Data

US 2007/0027375 A1 Feb. 1, 2007

Related U.S. Application Data

(63) Continuation of application No. 10/751,308, filed on Jan. 2, 2004, now Pat. No. 7,127,278, which is a continuation-in-part of application No. 10/749,471, filed on Dec. 30, 2003, now Pat. No. 7,024,235, which is a continuation-in-part of application No. 10/176,310, filed on Jun. 20, 2002, now Pat. No. 6,909,912, and a continuation-in-part of application No. PCT/US03/19294, filed on Jun. 19, 2003.

(51) Int. Cl.
*A61B 5/1455* (2006.01)
*A61M 16/00* (2006.01)

(52) U.S. Cl.
USPC ............. 600/344; 600/340; 128/204.23

(58) Field of Classification Search
USPC ............. 600/310, 322, 323, 340, 344
See application file for complete search history.

(56) References Cited

U.S. PATENT DOCUMENTS

| | | | |
|---|---|---|---|
| 3,847,483 A | 11/1974 | Shaw | |
| 4,457,756 A | 7/1984 | Kern et al. | |
| 4,685,464 A | 8/1987 | Goldberger et al. | |
| 4,830,014 A | 5/1989 | Goodman et al. | |
| 5,005,571 A | 4/1991 | Dietz | |
| 5,046,491 A | 9/1991 | Derrick et al. | |
| 5,218,962 A | 6/1993 | Mannheimer | |
| 5,309,908 A | 5/1994 | Friedman et al. | |
| 5,311,865 A * | 5/1994 | Mayeux | 600/340 |
| 5,335,656 A | 8/1994 | Bowe et al. | |
| 5,335,659 A | 8/1994 | Pologe et al. | |
| 5,619,992 A * | 4/1997 | Guthrie et al. | 600/310 |

(Continued)

FOREIGN PATENT DOCUMENTS

| | | |
|---|---|---|
| WO | 9920332 A1 | 4/1999 |
| WO | WO 00/21435 A1 | 4/2000 |

(Continued)

OTHER PUBLICATIONS

EP Search Report Application No. 12165281.2-1269, Date Jun. 27, 2012.

(Continued)

*Primary Examiner* — Eric Winakur
(74) *Attorney, Agent, or Firm* — Thomas | Horstemeyer, LLP

(57) ABSTRACT

The present invention relates to optimized gas supply utilizing photoplethysmography. Flow rate, pressure or amount of gas adjusted as a function of blood oxygen saturation data, photoplethysmography signals, or both, obtained from the pulse oximeter probe.

28 Claims, 29 Drawing Sheets

(56) References Cited

U.S. PATENT DOCUMENTS

| | | | |
|---|---|---|---|
| 5,638,818 A * | 6/1997 | Diab et al. | 600/310 |
| 5,743,857 A | 4/1998 | Shinoda et al. | |
| 5,788,634 A | 8/1998 | Suda et al. | |
| 5,800,349 A | 9/1998 | Isaacson et al. | |
| 5,817,008 A | 10/1998 | Rafert et al. | |
| 6,115,621 A * | 9/2000 | Chin | 600/323 |
| 6,142,149 A | 11/2000 | Steen et al. | |
| 6,144,867 A | 11/2000 | Walker et al. | |
| 6,190,327 B1 | 2/2001 | Isaacson et al. | |
| 6,213,955 B1 | 4/2001 | Karakasoglu et al. | |
| 6,263,223 B1 | 7/2001 | Shepherd et al. | |
| 6,285,895 B1 * | 9/2001 | Ristolainen et al. | 600/323 |
| 6,334,065 B1 | 12/2001 | Al-Ali et al. | |
| 6,371,114 B1 | 4/2002 | Schmidt et al. | |
| 6,537,225 B1 * | 3/2003 | Mills | 600/323 |
| 6,679,265 B2 | 1/2004 | Strickland et al. | |

FOREIGN PATENT DOCUMENTS

| | | | |
|---|---|---|---|
| WO | 0124845 A2 | 4/2001 | |
| WO | WO 01/54575 A1 | 8/2001 | |
| WO | WO 01/62194 A1 | 8/2001 | |
| WO | 0178597 A1 | 10/2001 | |

OTHER PUBLICATIONS

Kyriacou, et al., "Investigation of oesophageal photoplethysmographic signals and blood oxygen saturation measurements in cardiothoracic surgery patients", Physiological Measurement, Institute of Physics Publishing, Bristol, GB, vol. 23, No. 3. Jun. 14, 2002, pp. 533-545.

US 4,928,691, 5/1990, Nicolson et al. (withdrawn).

EP Search Report for European Patent Application No. 12165265.5, dated Oct. 22, 2012.

Hertzman, Alrick B., "Applications of Photoelectric Plethysmography in Peripheral Vascular Disease," Amer. Heart J., 20 (1940), pp. 750-761.

Hertzman, Alrick B., "The Blood Supply of Various Skin Areas As Estimated by the Photoelectric Plethysmograph," Am. J. Physiol. 124 (1938), pp. 328-340.

* cited by examiner

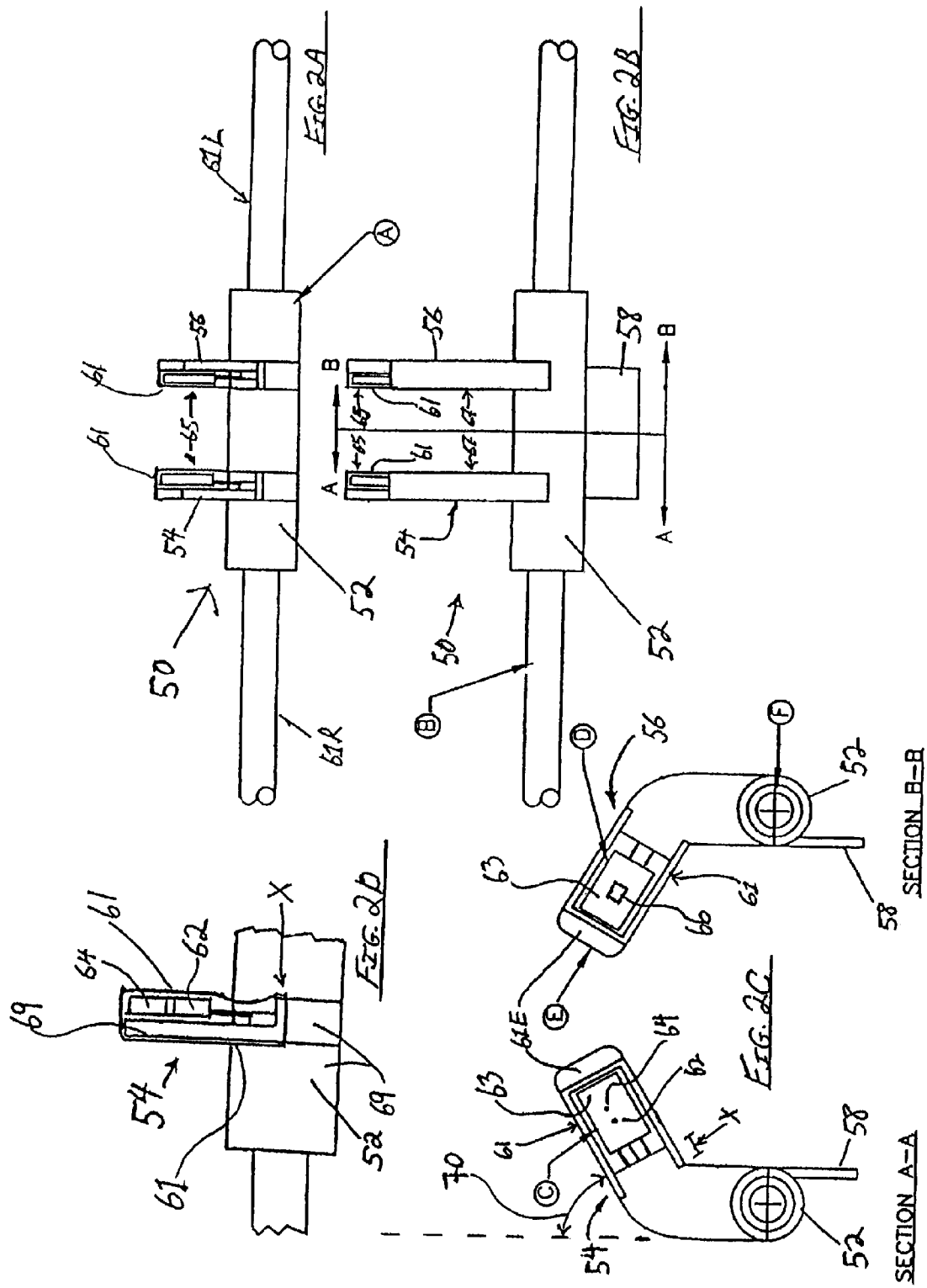

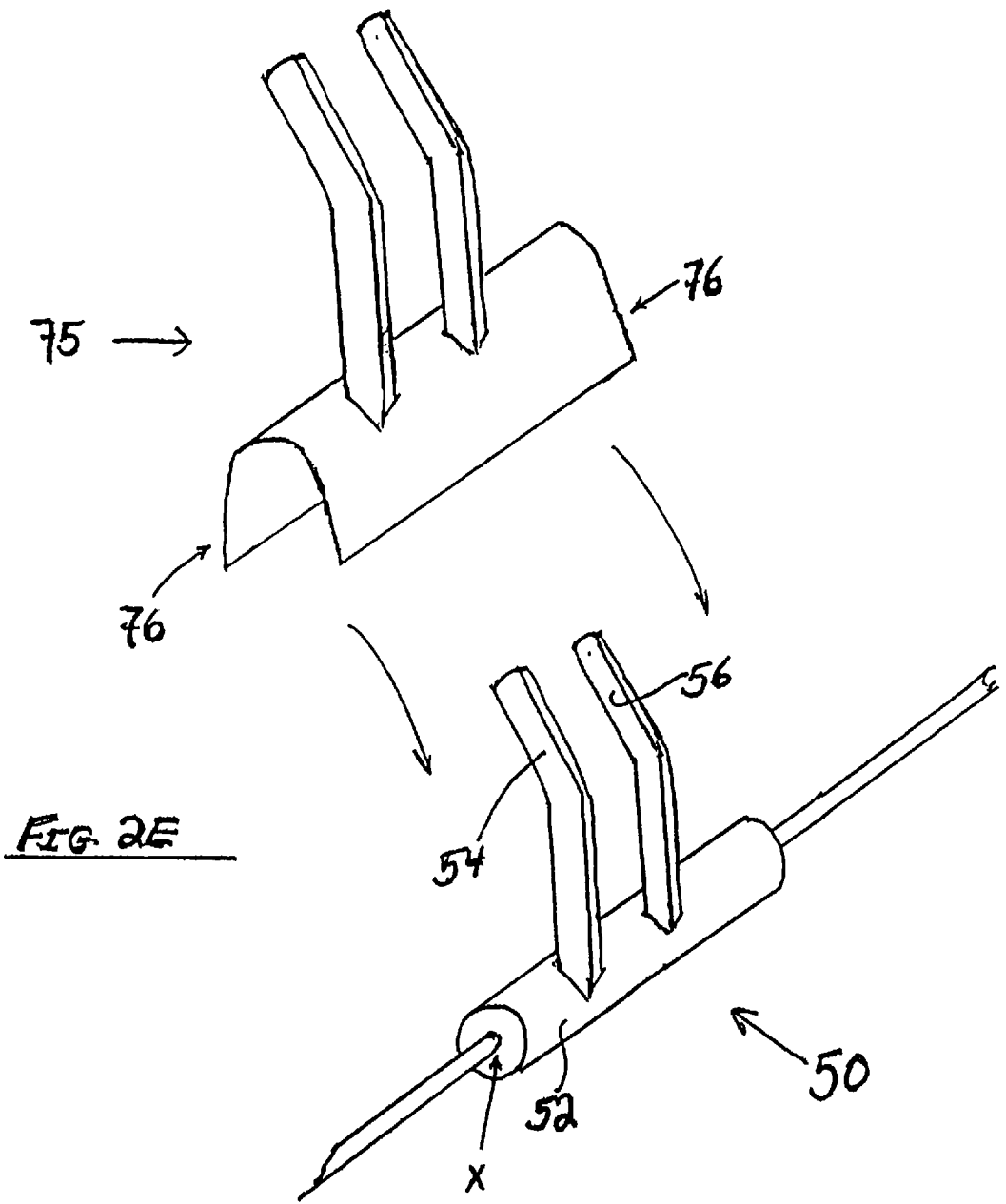

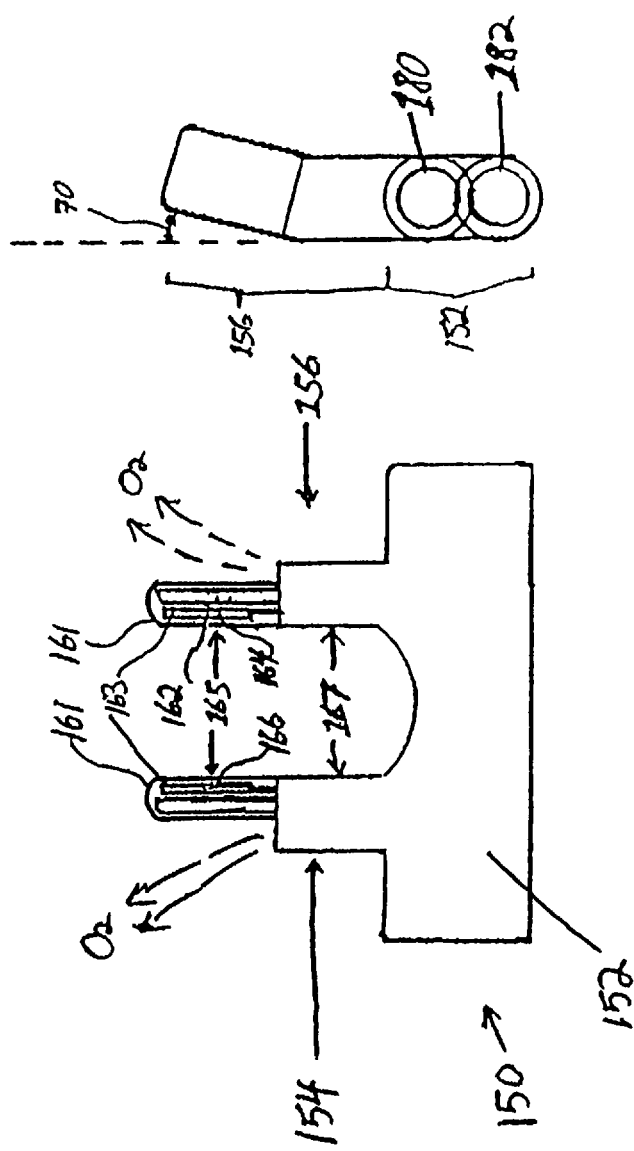

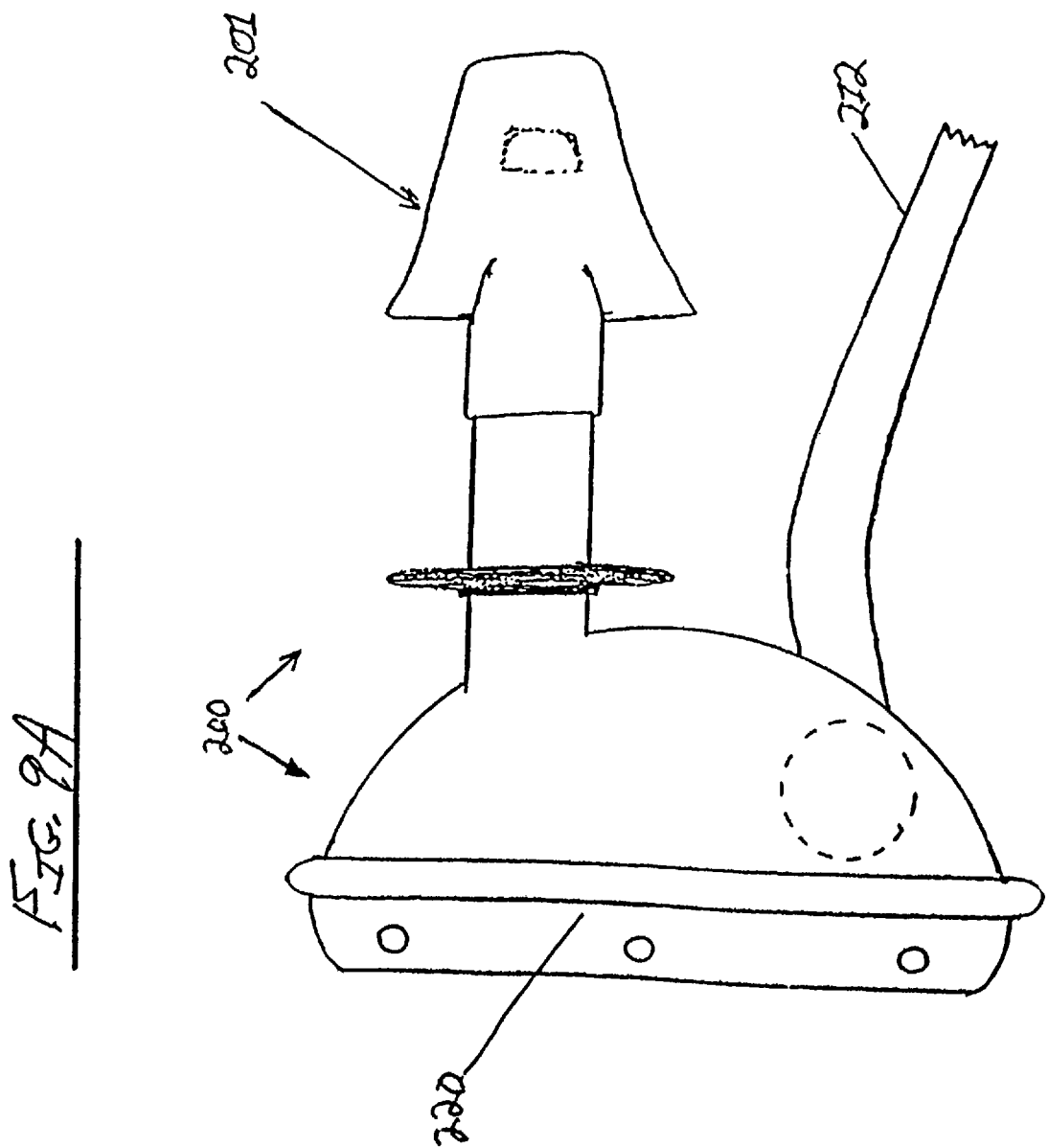

OPTIMIZED GAS SUPPLY USING PHOTOPLETHYSMOGRAPHY

CLAIM OF PRIORITY

This application is a continuation of U.S. patent application Ser. No. 10/751,308, Filed Jan. 2, 2004 now U.S. Pat. No. 7,127,278, which is a continuation in part of application Ser. No. 10/749,471 filed Dec. 30, 2003, now U.S. Pat. No. 7,024, 235, which is a continuation in part of application Ser. No. 10/176,310, filed Jun. 20, 2002, now U.S. Pat. No. 6,909,912 and International Application No. PCT/US03/19294, filed Jun. 19, 2003, and claims benefits under 35 U.S.C. §§ 120 for all above-noted applications. These patent applications are hereby incorporated by reference into this application in their entireties.

FIELD OF THE INVENTION

The present invention relates to the field of non-invasive measurement of signals indicating arterial blood oxygen saturation by means of pulse oximetry, and of photoplethysmographic signals indicating pressure and flow characteristics, and in particular, configurations of a pulse oximeter probe that sample across the cheek or the lip of a living subject. Such probes optionally include provision of a supply of oxygen or oxygen-enriched gas to a patient whose blood oxygen saturation is being measured, and/or a sampler of exhaled breath for capnography.

BACKGROUND OF THE INVENTION

Diseases, acute injuries, and other conditions can adversely affect blood flow to and in the limbs. In a general sense, agents and factors that may affect and lower circulation to the limbs, also known as peripheral circulation, include certain drugs, especially vasoconstrictors, poor perfusion per se due to shock, such as results from low blood volume, or septic or cardiogenic shock, certain traumas, external pressure (as from burns), hypothermia, and other mechanical abnormalities or injuries. In particular, decreased peripheral circulation may be caused by a number of disorders within the body including, but not limited to, atherosclerosis, Raynaud's disease, Buerger's disease, chronic obstructive pulmonary diseases (COPD), and embolic occlusive disease.

Poor blood flow reduces the amount of oxygen that is carried in the blood stream to cells. Emergency rooms, intensive care units, burn units, operating rooms, and ambulances treat a variety of critically ill patients in need of continuous monitoring of real time hemoglobin saturation and/or blood pressure readings. If oxygen levels in the blood become very low at peripheral sites, a variety of problems may occur which include inadequate resuscitation, cell death or necrosis that can lead to non-healing lesions, gangrene and amputation of limbs. Also, in progressive diabetes and other conditions that may result in atherosclerosis that affect peripheral circulation and perfusion, non-invasive measurement of circulation and/or resistance status is useful to monitor the progression of the disease and the effectiveness of treatments.

Also, many patients, especially among the elderly, are on chronic oxygen therapy; they are in need of supplemental oxygen on a routine basis. Such patients may have impaired and/or diminished cardiopulmonary capacity. When such patients are ambulatory, their supply of oxygen (usually a tank of compressed oxygen or liquid oxygen) must be transported with them wherever they travel. Oxygen from such supply passes through a regulator and thence, typically, via a tube to the nose where it is inhaled (e.g., via a nasal cannula or the like). Alternatively, the oxygen may be delivered by a cannula directly into the trachea (transtracheal supplemental oxygen). Embodiments of the present invention combine the supply of oxygen or oxygen-rich air with a pulse oximeter that adjusts the release of the supply to better match the actual bodily requirement based on the measured blood oxygen saturation. A pulse oximeter that receives the signal from the pulse oximeter probe is located a distance from the probe itself, and provides a blood oxygen saturation measurement to the user (and/or to a remote monitor), and/or, in certain embodiments acts to adjust the inflow rate or quality of the oxygen or oxygen-rich gas being supplied. This, depending on each particular user and his/her baseline settings, can either extend the life of a given supply of compressed oxygen or oxygen-rich gas, or provide oxygen or oxygen-rich gas on a more accurate, as-needed basis, in the latter case improving the health and/or performance of the user.

As to the latter benefit of this aspect of the present invention, provision of an accurate, as-needed supply of oxygen reduces the risk of and/or alleviates problems of hypoxia that are associated with improper adjustment of supplemental oxygen to patients in need thereof. Hypoxia, low oxygen delivery, or hypoxemia, low oxygen tension in the blood, cause a number of maladies including polycythemia (increased hematocrit) which leads to abnormal clotting. Polycythemia is a compensatory mechanism to chronic hypoxemia that typically builds up over weeks to months. It is typical in persons with chronic lung disease (and also persons living at high altitudes).

A more immediate, primary physiologic compensatory response to oxygen deficit is increased cardiac output. This is normal, such as during increased physical exertion. However, in persons who have impaired cardiocirculatory reserve, increased cardiac output in response to low arterial oxygen level can, under certain circumstances, eventually lead to death. The second immediate physiologic compensatory response to oxygen deficit is the extraction of more oxygen from hemoglobin within the capillaries of the body's organs. This normally happens either during an increase in oxygen demand (i.e., exercise, fever, shivering, etc.), or during normal demand but decreased oxygen delivery (i.e., due to inadequate blood flow, anemia, hypoxia). In such instances, metabolically active cells draw additional oxygen from the red blood cells which ultimately resulting in a decrease in the mixed venous blood's oxygen saturation falling from a typical 65% to 80% level to levels as low as 32% (see Hemodynamic Monitoring—Invasive and Noninvasive Clinical Application, by Gloria Oblouk Darovic, $3^{rd}$ Ed., 2002, Chapter 12). Chronic hypoxemia can lead to a switch by metabolically active cells to anaerobic metabolism, which, especially in patients with limited cardiopulmonary reserve, can lead to lactic acidosis and eventually death.

Hypoxemia also causes cognitive dysfunction either acutely or chronically which can lead to early dementia and death. Generally, based on the compensatory mechanisms and effects on body tissues, chronic hypoxemia may affect all organs in the body leading to failure of any or all organs.

In general, blood oxygen levels are currently measured by pulse oximetry, which can be divided into transmittance and reflectance types. Transmittance, or transillumination oximetry, involves the process whereby a sensor measures light extinction as light passes through a portion of blood-perfused tissue. Light is transmitted from one side of a portion of blood-perfused tissue, and is recorded by a sensor situated across the portion of tissue. Reflectance oximetry, on the other hand, has both the light source and the sensor on one side of the tissue, and measures reflectance back from the tissue. For both types of oximetry, multiple signals from the light sensor, or detector, are used to estimate the oxygen saturation and pulse rate from changes in absorption of the light detected throughout blood pulse cycles. The technology is based on the differential absorbence of different wavelengths of light by different species of hemoglobin.

Conventional pulse oximetry measurement in certain classes of patients, for instance severely burned patients, can be a significant challenge, yet this monitoring data is vital in operating room and intensive care settings. Most current pulse oximetric approaches depend upon available peripheral sites permitting transillumination oximetry which is sufficient for most surgical conditions and procedures. However, in one example, patients with severe burns often have only a few sites suitable for the effective placement of the transmitting pulse oximeter sensor. These patients often have severe circulatory compromise rendering the current peripheral pulse oximeters less effective.

The technology of pulse oximeters is well known (See "Pulse Oximetry: Principles and Limitations," J. E. Sinex, Am. J. Emerg. Med., 1999, 17:59-66). Pulse oximetry includes a sensor, or probe, with light source(s) generating at least two different wavelengths of light, and a detector placed across a section of vascularized tissue such as on a finger, toe, or ear lobe. Pulse oximetry relies on the differential absorbance of the electromagnetic spectrum by different species of hemoglobin. In a typical system, two distinct wavelength bands, for instance 650-670 nm and 880-940 nm, are used to detect the relative concentrations of oxygenated hemoglobin (oxyhemoglobin) and non-oxygenated reduced hemoglobin, respectively. The background absorbance of tissues and venous blood absorbs, scatters and otherwise interferes with the absorbance directly attributable to the arterial blood. However, due to the enlargement of the cross-sectional area of the arterial vessels during the surge of blood from ventricular contraction, a relatively larger signal can be attributed to the absorbance of arterial hemoglobin during the systole.

By averaging multiple readings and determining the ratio peaks of specific wavelengths, a software program can estimate the relative absorbance due to the arterial blood flow. First, by calculating the differences in absorption signals over short periods of time during which the systole and diastole are detected, the peak net absorbance by oxygenated hemoglobin is established. The signals typically are in the hundreds per second. The software subtracts the major "noise" components (from non-arterial sources) from the peak signals to arrive at the relative contribution from the arterial pulse. As appropriate, an algorithm system may average readings, remove outliers, and/or increase or decrease the light intensity to obtain a result. The results from one site provide a measurement of arterial oxygen saturation at that site, and also allows calculation of the shape of the pulse at the placement site of the probe, which can be developed into a plethysymograph. Among the various sources of signal interference and modification, it is noted that the shape of red blood cells changes during passage through arterial and venous vessels. This change in shape affects scattering of the light used in pulse oximetry. Algorithms are designed to correct for such scattering.

More sophisticated pulse oximetry systems detect at more than merely two bands, such as the 650-670 nm and 880-940 nm wavelength bands. For instance, the pulse oximetry article from a uni-erlangen web site stated that four LEDs, at 630, 680, 730 and 780 nm, each with 10 nm bandwidths, can determine the four common species of hemoglobin. The article further calculated that the detection of nine wavelengths in the range of 600 to 850 nm would provide greater accuracy in assessing these four forms of hemoglobin, oxyhemoglobin ($O_2Hb$), reduced hemoglobin (HHb), methemoglobin (MetHb), and carboxyhemoglobin (COHb). As used in the present invention, the term "pulse oximeter" or "oximeter" is meant to include all designs and types of pulse oximeters, including current and later developed models that transmit and detect at more than two wavelengths associated with absorption differences of these hemoglobin species.

At present, peripheral vascular resistance can only be measured invasively, or non-invasively by skilled technicians using Doppler flow devices. The use of Doppler and Doppler waveform analysis is now a standard investigation technique for obtaining measurements in blood flow resistance patients with possible circulatory disorders. For example, Dougherty and Lowry (J. Med. Eng. Technol., 1992: 16:123-128) combined a reflectance oximeter and a laser Doppler flowmeter to continuously measure both blood oxygen saturation and perfusion.

A number of patents have been issued directed to monitors, sensors and probes for use in pulse oximetry procedures. For instance, U.S. Pat. No. 6,334,065, issued on Dec. 25, 2001 to Al-Ali, et al., discloses a stereo pulse oximeter that provides for simultaneous, non-invasive oxygen status and photoplethysmograph measurements at both single and multiple sites. The invention is directed to the detection of neonatal heart abnormalities, particularly related to defects of heart-associated vessels, and specifically directed to Persistent Pulmonary Hypertension in Neonates (PHHN), Patent Ductus Arteriosis (PDA), and Aortic Coarctation. All of these conditions result in a flow of differentially oxygenated blood to different peripheral extremities. For instance, in PHHN and PDA, the blood that flows to the right hand is unaffected by the abnormal shunt that results in less oxygenated blood flowing to other areas. Thus, comparison of oxygen saturation values between a pulse oximeter sensor at the right hand and at, for instance, a foot site, is stated to detect or confirm the diagnosis of such neonatal heart abnormalities. Continuous monitoring with such pulse oximetry also is proposed, to provide feedback on the effectiveness of treatments or surgery to deal with these neonatal cardio/cardiopulmonary conditions. U.S. Pat. No. 6,334,065 does not address the use of two probes for detection, confirmation, or monitoring of perfusion- and resistance-related conditions in the patient. Such conditions would not be expected in a neonatal patient, and are instead more likely found in aging patients and in patients with certain accident conditions unrelated to neonatal heart and heart-associated vessel anomalies.

U.S. Pat. No. 6,263,223 was issued on Jul. 17, 2001 to Shepard et al., and teaches a method for taking reflectance oximeter readings within the nasal cavity and oral cavity and down through the posterior pharynx. Whereas the conventional transillumination pulse oximeter probe detects the light not absorbed or scattered as it crosses a vascularized tissue covered by skin (i.e., the LEDs and photodetector are separated by the tissue), a reflectance oximeter probe detects light by backscattering of light that traverses vascularized tissue not bounded by skin and is reflected back to a detector positioned on the same side of the tissue as the LEDs (e.g., on tissue in the mouth). The method includes inserting a reflectance pulse oximeter sensor into a cavity within a subject's skull and contacting a capillary bed disposed in the cavity with the reflectance pulse oximeter sensor. The method uses standard pulse oximeter sensor probes placed over capillary beds close to a buccal surface, posterior soft palate, hard palate or proximal posterior pharynx, including the tongue, nares or cheek. Reflectance pulse oximetry at these sites determines arterial oxygen saturation. One major problem with this device is that it does not permit cross-site comparisons of oxygen saturation values between several tissue sites. In addition, the pulse oximeter device used in this invention is an elongated tube that is inserted far into the nasal or oral cavity down into the pharynx, which is a highly invasive procedure.

U.S. Pat. No. 4,928,691, issued on May 29, 1990 to Nicolson et al., and currently withdrawn, discloses a non-invasive, electro-optical sensor probe and a method for its use. The sensor is enabled to measure light extinction during transillumination of a portion of blood-perfused tissue and to calculate the oxygen saturation and pulse rate from changes in absorption of the light detected. The sensor probe is placed at a central site such as the tongue, cheek, gum or lip of the patient and provides continuous assessment of arterial oxygen saturation and pulse rate. The sensor is malleable and extremely flexible, and is stated to conform to the structure of the skin and underlying tissue. U.S. Pat. No. 4,928,691 states that measurement at the preferred central sites provide accurate oxygen saturation and pulse readings for "patients with lowered or inconsistent peripheral perfusion." Critically, the probes according to U.S. Pat. No. 4,928,691 are highly flexible, leading to a high likelihood that upon typical movement of the patient there would be mal-alignment between the light source(s) and sensor, resulting in skewed, non-usable, or unreliable signals and results. Also, there is no teaching or suggestion to compare oxygen saturation values between several tissue sites to identify, characterize, or monitor peripheral perfusion conditions in such patients.

U.S. Pat. No. 5,218,962 was issued on Jun. 15, 1993 to Mannheimer et al., teaches a pulse oximetry system which monitors oxygen saturation and pulse rates by sensing the blood characteristics at two or more peripheral sites. The device includes one or more pulse oximetry probes which passes light through unique regions of tissue and a sensor which detects the amount of light passing through the tissue, and an instrument that independently calculates oxygen saturation level within each region. The difference in values represents how much the oxygen saturation of the first region of tissue differs from the oxygen saturation of the second region of tissue. When the difference between the two values is below a set threshold, the '962 patent attributes this to a sufficiently high probability that the value is true, and displays an oxygen saturation value that is a function of the two independent values. Where there is a difference greater than a set threshold, no oxygen saturation value is displayed. Thus, the '962 patent attributes substantial differences between two sites to be due to error, rather than to an indication of a problem with peripheral perfusion and/or resistance.

U.S. Pat. No. 5,335,659, issued on Aug. 9, 1994 to Pologe, teaches a nasal septum probe for photoplethysmographic measurements that clips onto a patient's nasal septum. Pulse oximetry is one of the stated applications for the apparatus. Structurally, the apparatus disclosed and claimed in the '659 patent has a body, or housing, from which two probe arms extend, these arms being sized to enter the nostrils of a nose. One arm bears at least two light sources, and the other arm bears at least one light detector. The probe apparatus securely grasps the nasal septum in such a way that there is contact on both sides of the nasal septum at the same time with both the light sources and the light detector. In all embodiments, the light sources and the light detector actually protrude from the main body of the respective probe arm, and are positioned to exert pressure upon and indent the tissue of the nasal septum. In some embodiments and all claims, a supply of gas is also provided from a source through a support means and to the nasal septum. However, the '659 patent does not disclose a nasal pulse oximeter probe that does not need to press into the tissue of the nasal septum in order to obtain reliable pulse oximetry data, nor a probe that includes an angle, or bend, to reach a desired highly vascular plexus on the septum.

U.S. Pat. No. 6,144,867, issued on Nov. 7, 2000 to Walker, teaches a flexible pulse oximeter sensor assembly capable of doubling over to surround a body part, such as an ear lobe, and comprised of a flexible base having a hole passing through it, a post preferably having a sharp tip, and a grommet. In use the sensor assembly wraps around a body part, and the post, or pin, passes through the body part to secure the probe to the body part. The grommet frames the hole and engages and holds the post. The patent discloses that body parts other than the ear lobe that may be pierced by the post (and, presumably, therefore suitable as a site for use of the sensor) include the webbing between the fingers and toes, the tongue, the nose, eyebrows, cheek/lip, breast nipples, and the foreskin.

WIPO Application No. WO0021435A1, to Barnett et al., was published Apr. 20, 2000. This publication teaches a non-invasive spectrophotometric examination and monitoring of blood metabolites in multiple tissue regions on an ongoing and instantaneous basis. The method includes attaching multiple sensors to a patient and coupling each sensor to a control and processing station enabled to analyze signals conveyed thereto. The control and processing station visually displays the data from multiple sites for direct mutual comparison of oxygen saturation values from multiple sites. A key aspect of the invention is the use of a "near" and a "far" (or "deep") detector at each detection site. Based on the positioning of the light-generating devices and the near and far sensors, the far sensor receives absorption signals from deeper inside the brain tissue. In a basic configuration, the "near" sensor, or detector, principally receives light from the source whose mean path length is primarily confined to the layers of skin, tissue, and skull, while the "far" detector which receives light sprectra that have followed a longer mean path length and traversed a substantial amount of brain tissue in addition to the bone and tissue traversed by the "near" detector. Other configurations indicate receptors receive signals from sources across the entire brain cross-section. This is stated to provide information about, by calculation differences, the condition of the deeper tissue, in particular the brain. The method is directed to compare oxygen saturation values for cerebral tissue, such as comparing the two hemispheres during surgery. The WO0021435A1 invention distinguishes itself from standard pulse oximetry of arteries close to the surface of the body, and focuses primarily on analysis of deeper tissues and organs. The application does not teach a method to measure "surface" peripheral or central tissue sites for development of information regarding perfusion status.

WIPO Application No. WO0154575A1, to Chen et al., was published on Aug. 2, 2001. This publication teaches a non-invasive apparatus and method for monitoring the blood pressure of a subject. A monitor is used for continuous, non-invasive blood pressure monitoring. The method includes using sensors to detect a first blood pressure pulse signal at a first location on patient and detecting a second blood pressure pulse signal at a second location on the patient; measuring a time difference between corresponding points on the first and second blood pressure pulse signals; and, computing an estimated blood pressure from the time difference. The first and second sensors are placed at locations such as a finger, toe, wrist, earlobe, ankle, nose, lip, or any other part of the body where blood vessels are close to the surface of the skin of a patient where a blood pressure pulse wave can be readily detected by the sensors, and/or where a pressure pulse wave from the patient's heart takes a different amount of time to propagate to the first location than to the second location.

In one regard, a superior monitor system would be able to provide real-time continuous measurements of signals that would be analyzed to provide arterial oxygen saturation, blood pressure, and pulse rate. A superior monitor system would utilize at least two pulse oximeter probes, one of which is placed at a highly perfused central tissue, such as the lip, tongue, nares, cheek, and a second probe placed at a typically less perfused areas such as a finger or toe. Also, in some situations, a peripheral probe may be placed at sites in or distal from areas that may be or are affected by disease- or accident-related diminished blood perfusion to tissues.

An additional aspect of a superior oximeter system provides both an inflow means of oxygen or oxygen-rich gas to a patient in need thereof, and an integral or adjoining pulse oximeter probe. This aspect is in conjunction with the above-described two pulse oximeter probe system, or in a system that only has one oximeter probe. In either case, one pulse oximeter probe, positioned at the nose or mouth, detects the levels of oxygenation saturation of blood in the patient, and detection of low or lowering oxygenation saturation levels results in one or more of: setting off a local or remote alarm or message; increasing the flow of oxygen or oxygen-rich gas to said patient. Likewise, detection of higher or increasing oxygenation levels results in one or more of: setting off a local or remote alarm or message; decreasing the flow of oxygen or oxygen-rich gas to said patient. Preferably, the pulse oximeter probe at the nose or mouth is integral with the delivery means of the oxygen or oxygen-rich gas. Preferably, the control of oxygenation levels is by signaling to (manually or automatically) adjust a valving mechanism that controls output flow from a source of auxiliary of oxygen or oxygen-rich gas. By such feedback mechanism the quantity of oxygen or oxygen-rich gas is conserved, and the needs of such patient are more closely attuned to the fluctuations in oxygen demand during activities at varying levels of exertion during a period of time.

As to references that pertain to the combining of a pulse oximeter with a system to control the inflow of oxygen or other oxygen-rich gas to a patient in need thereof, the following U.S. patents, and references contained therein, are considered to reflect the state of the current art: U.S. Pat. Nos. 4,889,116; 5,315,990; 5,365,922; 5,388,575; 6,371,114; and 6,512,938. None of these references are specifically directed to a combined, preferably integral combined pulse oximeter sensor/nasal cannula, which, when combined with an oximeter, or with an oximeter that controls the inflow of such oxygen or other oxygen-rich gas to the patient, provide the advantages disclosed and claimed herein.

All patents, patent applications and publications (scientific, lay or otherwise) discussed or cited herein are incorporated by reference to the same extent as if each individual patent, patent application or publication was specifically and individually set forth in its entirety.

SUMMARY OF THE INVENTION

One aspect of the present invention relates to a novel non-invasive vascular perfusion/resistance monitor system having at least two pulse oximeter probes positioned at locations on the body of a patient, the signals from which may be capable of indicating a problem with peripheral perfusion and/or resistance. In practice each probe emits at least two different light frequencies, such as by light-generating diodes (LEDs), and such emitted light is detected by at least one light detector, such as a photodiode detector. A general-purpose computer or a special purpose computer is employed to perform complex mathematical computations based, typically, on the signal intensity and timing from the at least two pulse oximeter probes, and on signals from the light detectors of each of the probes. Proper analysis by software programming in such general-purpose computer or special purpose computer outputs results to a display, printer, etc. that suggests or indicates (depending on relative differences in the signals at different locations, and upon other conditions) whether a condition of diminished or abnormal vascular perfusion/resistance may exist in a selected body area. The system also monitors changes in such conditions during treatment interventions.

In a preferred embodiment, software programming provides for a signal to a user of the device to alert the user when signals from a central or a non-central probe are of such low pulse amplitude that either the probe needs repositioning or that the patient is experiencing extremely low pulse at the probe site (and is therefore in need of acute intervention). The software program also converts the signals from the light detectors to calculate various oxygen saturation values and various blood pressure values (either simultaneously or separately). These values are used for evaluating the vascular perfusion/resistance and/or blood pressure of a patient based on the locations of the two or more probes.

Each probe is designed for monitoring blood oxygen saturation and/or blood pressure at different vascular bed sites on a patient. Critically, one of the at least two sites on a patient is at what is designated a "central source" site ("CSS"). The inventors have discovered that flow directed through the carotid artery and detected at CSS sites, such as the lip, tongue, nasal nares, and facial cheek, are typically strong and unaffected by perfusion-lowering conditions. In patients who do not have perfusion-lowering conditions, a second or third probe site at "non-central" site (NCS), such as an extremity (i.e., fingers, toes, etc.), provides oxygen saturation and pulse values fairly comparable to values from the CSS. However, when a patient has a perfusion-lowering condition, the probe site at an affected extremity provides noticeably different oxygen saturation and pulse values compared to the CSS values. The difference in saturation values between the CSS and one or more sites is then used to assess peripheral vascular resistance, perfusion and/or peripheral vascular disease.

As used in this disclosure, when a particular wavelength or band of wavelength is stated at which an LED or other light-generating source emits light, it is understood that such light-generating source may and probably does emit light across a broader range. However, what is meant by such statement is that such light-generating source is designed to emit at a frequency curve which has a peak at or near such stated wavelength or band. It is further understood that any known means of limiting non-desired light energy, such as by selective filtration, may be used in conjunction with such light-generating sources to improve the accuracy and/or precision of the emissions of such light-generating sources.

As used in this disclosure, a "pad" is meant to indicate a housing, or an enclosure, over a light-generating or a light-sensing device on the probe, which provides a barrier to fluids, and permits transmission of light of the relevant wavelengths to the present invention. A typical pad has a composition of clear plastic.

As used in this disclosure, a "conductor" is meant to indicate any physical pathway or any system that communicates a signal or electricity from a first to a second location. Signals and electricity can be conducted by conventional means, such as by sending electrical impulses along a continuous copper wire, by more sophisticated means, such as by converting the signals into radio waves and transmitting these waves such that a receiver receives the signals and thereafter sends them to the controller, or by any other way now known or later developed.

As used in this disclosure, whether or not so stated in a particular sentence, the term "oxygen" may be taken to mean "oxygen or any oxygen-rich air or other gas mixture that contains oxygen" which is used for provision of oxygen to a patient or to a person in need thereof. The context of a particular usage in this disclosure indicates whether this broader definition is to be used, or whether a particular example is referring instead to the use of pure oxygen exclusively.

While some researchers have attempted to gauge accuracy by comparing the results from two different pulse oximeter probe sites (see U.S. Pat. No. 5,218,962), and other researchers generally recognized that "central" sites are generally more reliable and responsive than "peripheral" sites (see U.S. Pat. Nos. 6,263,223, and 4,928,691), the present invention recognizes the reasons for the inconsistently different results between CSS and non-CSS sites. Specifically, patients having compromised peripheral circulation and/or resistance will tend to have lower peripheral values than patients without such compromised conditions. By such recognition, detection and monitoring impaired peripheral circulation is possible through the present disclosure. The monitoring system of the present invention, in certain embodiments, additionally provides an indication of vascular resistance through continuous monitoring of the transit time difference of the blood oxygen saturation values and the blood pressure values between the two sites.

It is an object of the present invention to provide a monitoring system which includes two pulse oximeter sensors, or probes, connected to a monitor system as a non-invasive means for continuously measuring blood oxygen saturation values and/or blood pressure and/or pulse values, wherein the system detects and monitors changes in vascular perfusion and resistance in a patient. The overall system particularly assesses differences in peripheral blood flow which may be impaired in certain illnesses and accident conditions.

Another object of the present invention is to provide probes functionally constructed to provide more reliable signal reception and transmission for patients, such as those in ICU, surgery, post-operative care, and patients with respiratory, circulatory problems, or under anesthetics. In particular, pulse oximeter probes are configured to be placed, respectively, across the lip or cheek, in the nostrils of the nose, and on the tongue.

Thus, one object of the invention is to provide a novel configuration of an oximeter probe that is well-suited for placement across the lip of the mouth of a patient, or the cheek of a patient, in which one side of the probe is situated outside the oral cavity and a second side is positioned inside the mouth cavity, and the tissue between the two sides is assessed by transillumination pulse oximetry. Another object of the invention is to combine the probe for placement across the lip or cheek of the present invention with sampling devices for capnography sampling, either with or without a structure or assembly for the supply of oxygen, as from a cannula. Another object of the invention is to combine with the probe for placement across the lip or cheek a disposable cover to slip over the probe.

Still another object of the present invention is to utilize the photoplethysmographic data obtained from the probes of the present invention for diagnosis and monitoring of clinical conditions.

Another object of the invention is to provide a novel configuration of an oximeter probe that is well-suited for placement at the nasal cavity of a patient, in which one side of the probe is situated to the left side of the nasal septum, and a second side is positioned to the right side of the nasal septum, and the tissue between the two sides is assessed by transillumination pulse oximetry. This design, in a preferred embodiment, also functions to provide oxygen to the patient through channels provided in the structure of the probe. The embodiments of the nasal probe of the present invention advance the art by obtaining reliable and repeatable pulse oximetry and plethysmography data from the interior nasal septum with the extensions going into the nose being designed and spaced so as to not press into the tissue of the septum. Further, the extensions of the probe, where the light-generating and the light-detecting components are positioned, do not simultaneously contact the respective areas of mucosal tissue of the nasal septum. This provides a more comfortable probe than the prior art that, advantageously, does not impair blood flow in the vascular tissue being evaluated, and does not harm that tissue as may occur from a probe that exerts simultaneous pressure from both sides.

Another object of the invention is to combine the nasal probe of the present invention with sampling devices for capnography sampling, either with or without a structure or assembly for the supply of oxygen, as from a cannula. Another object of the invention is to provide a novel configuration of an oximeter probe that is well-suited for placement on both sides of either the right or the left nasal alar (i.e., the alar nari). One side of the probe is situated to the outside of the nasal nari, and a second side is positioned to the inside of the nasal nari, and the tissue between the two sides is assessed by transillumination pulse oximetry.

Another object of the invention is to provide a novel configuration of an oximeter probe that is well-suited for placement on the tongue of a patient, in which one part of the probe is situated along one surface of the tongue, and an opposing part is positioned in such a manner as to capture a section of the tongue such that a transilluminable cross-section of tongue tissue is held between the two probe parts, and the tongue tissue between the two probe parts is assessed by transillumination pulse oximetry.

It is another object of the present invention to provide pulse oximeter probes dimensioned and configured to be expandable, spring-loaded, and flat surfaced for utilizing measurements on extremities and earlobes; buccal mucosal-buccal surface or dorsal ventral portion of the tongue; and properly sized configurations for the nasal alars (i.e., alar nares) and cheek and/or tongue for critically ill, burned, or traumatized patients. A related object is to provide a configuration for an oximeter probe that utilizes two opposed, substantially flat probe surfaces that tend toward each other, such as by spring tensioning.

It is a further object of the present invention to provide a monitoring system that measures vascular resistance and/or perfusion continuously to improve volume resuscitation and/or drug therapy.

It is still a further object of the present invention to provide a monitoring system that can be used as a multi-probe pulse oximeter to monitor blood oxygen saturation differences, pulse transit time differences, or blood pressure, or any combination thereof.

It is still another further object of the present invention to provide specifically constructed probes used to transmit and receive the light to vascular bed sites that are not normally available for use due to burns, trauma, and surgery on the extremity.

It is still another further object of the present invention to provide a monitoring system that is easily fabricated from low cost material and is adaptable for use in an operating room, intensive care unit, emergency room or other areas to treat patients in need of hemodynamic monitoring.

Still another object of the present invention is to provide a pulse oximeter probe and a supply of oxygen or oxygen-rich air, in combination, and functioning in concert with each other and with oximetry circuitry, such that the level and trend in blood oxygen saturation are determined by the pulse oximeter and changes in blood oxygen saturation direct a change (i.e., an increase or a decrease) in the release of oxygen or oxygen-rich air to the patient whose blood oxygen saturation is being measured. In one type of control of the flow of oxygen or oxygen-rich air, an electronic regulator is controlled by signals from a processor that receives data from the pulse oximeter.

Thus, one particular object of the present invention is to integrate a novel nasal pulse oximeter probe of the present invention with a nasal cannula. Another particular object of the present invention is to integrate a pulse oximeter probe with either a self-container breath apparatus (SCBA) or with the regulator of a self-contained underwater breathing apparatus (SCUBA). Blood oxygen measurements obtained by the so integrated pulse oximeter probe then are used to regulate the percentage oxygen in the supply of gas to the user, and/or to regulate the flow rate to the user upon inhalation. In the case of a SCBA apparatus that is combined with a pulse oximeter probe and oximeter, where that mask is worn in environments with toxic or noxious atmospheres, a critical role of the sensor is to indicate to the user when they are becoming hypoxemic, i.e. when there are potentially dangerous gases leaking into the mask. In the case of a SCUBA apparatus that is combined with a pulse oximeter probe and oximeter, for any dive the oximeter can provide information related to the formation of an air embolus. For deep dives, where specialty mixed gases are used and oxygen concentration in such mixtures are actually reduced from its concentration in air, the oximeter data on blood oxygen saturation provides a warning of current or pending hypoxemia. When further combined with a control to adjust the relative concentration of oxygen to other gases, this device serves to increase the relative oxygen concentration delivered to the diver when the oximeter data trend so indicates the need.

Still another object of the present invention is to provide a pulse oximeter probe and a supply of oxygen or oxygen-rich air, in combination, and functioning in concert with each other and with oximetry circuitry, such that the level and trend in blood oxygen saturation are determined by the pulse oximeter and changes in blood oxygen saturation that indicate a sufficient downtrend in the blood oxygenation status results in a local or remote alarm to alert the patient and/or others to the problem.

Still another object of the present invention is to utilize the photoplethysmographic data obtained from the probes of the present invention for diagnosis and monitoring of clinical conditions.

The foregoing has outlined some of the more pertinent objectives of the present invention. These objectives should be construed to be merely illustrative of some of the more prominent features and applications of the invention. Many other beneficial results can be attained by applying the disclosed invention in a different manner of modifying the invention as will be described.

It is to be understood that the foregoing general description and the following detailed description are exemplary and explanatory only and are not to be viewed as being restrictive of the present, as claimed. These and other objects, features and advantages of the present invention will become apparent after a review of the following detailed description of the disclosed embodiments and the appended claims.

BRIEF DESCRIPTION OF THE DRAWINGS

FIGS. 2A-C provide top, front, and cross-sectional views, respectively, of a pulse oximeter probe for positioning in the nares of a nose of a patient. Connecting wires are shown in schematic format, not to scale. FIG. 2D provides an enlarged view of one area of FIG. 2A. FIG. 2E provides a perspective view of a protective sheath used to cover the pulse oximeter probe of this figure.

FIGS. 8A and 8B provide front and side views, respectively of a novel combined nasal pulse oximeter probe/oxygen cannula.

FIG. 9A provides a side view of a typical self-contained underwater breathing ("SCUBA") apparatus typical of the prior art apparatuses. FIG. 9B provides a side view of a SCUBA apparatus of the same configuration, with a cross-lip pulse oximeter sensor added to this apparatus.

DETAILED DESCRIPTIONS OF EMBODIMENTS

The present invention discloses pulse oximeter probes for use with pulse oximeter systems in general. The present invention also discloses a novel non-invasive vascular perfusion and/or resistance status monitor apparatus and methods of using same.

Figure 1:
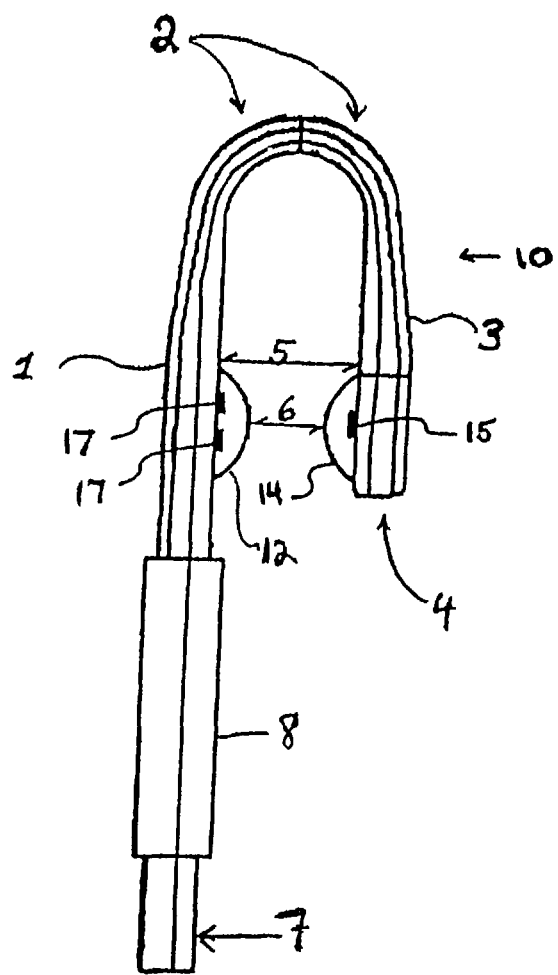
FIG. 1 illustrates a side view of a hook-shaped pulse oximeter probe showing a preferred positioning of a LED pad having two LED's and at least one photodiode detector according to the present invention. This probe is configured for positioning across the lip or cheek of a patient.

FIG. 1 illustrates a pulse oximeter probe, 10, of the invention, that is configured for placement with a section of the probe placed inside the mouth for measurement across the vascularized tissue of the lip or cheek. The probe, 10, as depicted in FIG. 1, is comprised of a frame that is generally hook-shaped, having a longer proximal arm, 1, a curved bridging section, 2, and a shorter distal arm, 3, the latter arm having a free end, 4, that enters the mouth when in use. At least one portion of the proximal arm, 1, is positioned at a specified distance, 5, from an opposing portion of the distal arm, 2, to provide a distance between the closest points of the two opposing arms, 6, that accommodates the thicknesses of the lips and/or cheeks of a desired range of patients. As shown in FIG. 1, the opposing portions of the proximal arm, 1, and the distal arm, 2, that are the specified distance, 5, represents most of the lengths of these arms. In other embodiments of this probe, a smaller percentage of the total span of opposing arm sections may be set to such specified distance.

The probe may be used once and disposed, or may be repeatedly used on different patients. Preferably, the probe frame is constructed of metals, plastics, and other materials subjectable to repeated cleaning with standard antiseptic solutions, or sterilizable by other means. A cable, 7, houses conductors (not shown), such as but not limited to insulated electrical wires, that connect operative components further in the probe, 10, with an oximeter monitor (not shown). A boot, 8, connects the cable, 7, to the proximal arm, 1, of the hook-shaped frame of the probe 10. Preferably the cable, 7, is flexible. The boot, 8, primarily serves to connect the cable, 7, with the frame, and secondarily to provide a handle with which the patient or attendant grip the probe. In other designs of the lip/cheek probe, a boot is not required where a direct connection is made between the cable and the frame of the probe.

In the embodiment depicted in FIG. 1, the probe 10 comprises two LEDs 17 within an LED pad, 12, and one photodiode detector 15 within a photodetector pad, 14. These are the operative components of the probe, 10, and are connected to a monitor system (not shown) by conductors (not shown) to transmit electrical signals. It is noted that although the two LEDs, 17, are shown as two physically separate components in FIG. 1, when present on a circuit board, typical LEDs are very small (about the size of a pencil point), yet discrete components. Thus, the two LEDs alternately can be represented as both being present on a single structure in other figures.

Each probe 10 is sized appropriately to be placed with the open end, 4, inside a patient's mouth, so that the distance, 6, between the LED pad, 12, and the photodetector pad, 14, conforms to the thickness of the lip or cheek vascular bed of the patient. It is noted that FIG. 1 is not accurately drawn to scale, and given the true small size of the pads 12 and 14, the actual difference between the distances 5 and 6 is less than about 0.5 inches. In practice, one probe 10P (not shown) is sized for the average pediatric patient, age 6-12, and another probe 10A (not shown) is sized for the average adult patient.

The embodiment depicted in FIG. 1 has the light-sensing device, such as the photodiode detector, 15, positioned in the mouth, on the side with the open end, 4, as shown in FIG. 1. Having the light-sensing device on the inside side of the cheek or lip minimizes erroneous readings due to interference from ambient light sources. Such light sources are much more likely to affect a light-sensing source that is positioned on the outside side of the cheek or lip. However, having the light-sensing source positioned on the outside side of the cheek or lip is within the scope of the invention.

Individual conductors provide electrical signals that power the LEDs 17. Other conductors carry signals from the photodetector, 15. Optionally, other sensors, such as for temperature, may be added to the probe, 10, and have individual conductors for them also passing in the cable, 4, to the frame of the probe, 10. The probe, 10, is used to generate data used to calculate oxygen saturation, pulse shape, blood pressure measurement (by measurement of pulse transit time to a second site), and any combination of these.

The bridging section, 2, flexes to permit conformance to a range of tissue thicknesses greater than the nominal unflexed spans, as depicted by distances 5 and 6. The probe in FIG. 1 preferably is constructed of materials, such as nylon plastic, that impart a resiliency such that after bending, the probe returns substantially to its original shape. This resiliency allows the angular and dimensional relationships between the light-generating sources and the opposingly placed light detector to remain substantially consistent. Thus, the material for one embodiment of the probe has a degree of flexibility, and the material has sufficient memory to substantially return to its original shape after a normal flexion. This allows for standard use that may involve placement across lip and cheek tissue sections having different thicknesses, and movement across a thicker tissue section to ultimate placement at a thinner section.

For instance, in one embodiment of this configuration, the body of the probe, 10, is made of nylon plastic. The flexibility of the bridging section, 2, the proximal arm, 1, and the distal arm, 3, is such that less than 5 grams of force deflects the open end, 4, in one direction or the other (toward or away from the opposing section) by about 1/16 inch. The force required increases logarithmically, such that to move the open end, 4, outwardly 0.25 inch required between about 1,250 to 1,550 grams of force, and the force required to move the open end, 4, inwardly (toward the opposing section) required between about 2,200 to 2,700 grams of force. After such forces the nylon material demonstrated memory, returning to within 1/16 inch of the original position, thus demonstrating a resilient quality to the structure of the probe.

In addition, the material of each of the LED pad, 12, and the photodetector pad, 14, deflects upon application of pressure from adjacent tissue by up to about 0.050 inch. Thus, the overall flexibility is sufficient to accommodate a wide range of sizes of cheek and lip sections, which the axis of light transmission from the LEDs is reliably aligned to the photodiode or other light sensor. While not being bound to a particular theory, it is believed that maintaining appropriately narrow alignment of these elements improves the reliability, precision and accuracy of the signals from the probe.

More flexible probes are alternate embodiments of the present invention. For instance, the structural material and thickness is adjustable such that only between about 150 to 1,250 grams of force moves the open end, 4, outwardly 0.25 inch, and between about 200 to 2,200 grams of force the force moves the open end, 4, inwardly (toward the opposing section).

Less flexible probes also are alternate embodiments of the present invention. For instance, the structural material and thickness is adjustable such that between about 1,550 to 3,500 grams of force moves the open end, 4, outwardly 0.25 inch, and between about 2,700 to 5,000 grams of force the force moves the open end, 4, inwardly (toward the opposing section). Alternately, in a more rigid probe, the structural material and thickness is adjustable such that between about 3,500 to 5,500 grams of force moves the open end, 4, outwardly 0.25 inch, and between about 5,000 to 8,000 grams of force the force moves the open end, 4, inwardly (toward the opposing section). Such probes are made of metals or polymer composite materials. The resiliency is expected to vary inversely, roughly, with the flexibility of probes of such alternative embodiments.

Although in FIG. 1 the bridging section, 2, is curved, other embodiments of this lip/cheek probe may have a bridging section of any shape and angle, so long as it spans a distance and connects the opposing sides upon which the operative components of the probe are placed. Further, as to all lip/cheek probes of the present invention, it is noted that the dimensions, materials and structures of such probes provide for maintaining a desired position on the lip or cheek of a patient, such that the insertion of a post, or pin, through the lip or cheek, so as to retain such desired position of the respective probe, is not required.

FIG. 2A-D illustrates a second pulse oximeter probe, 50, of the invention, that is configured for placement inside the nostrils of the nose for measurement across the vascularized tissue of the nasal septum. The nasal septum generally is defined as the bone and cartilage partition between the nasal cavities, or the dividing wall that runs down the middle of the nose so that there are normally two sides to the nose, each ending in a nostril. As used herein, the term nasal septum is comprised of at least two parts. A columella nasi ("exterior septum" or "columella") is defined as the fleshy lower margin (termination) of the nasal septum at the opening of the nose (i.e., the nostrils or nares). A more interior part, broadly termed herein the "interior septum," extends interiorly from the columella and is comprised of the cartilaginous and bony part of the septum. Along this interior part of the nasal septum is found the vascularized tissue of the nasal septum, including certain highly vascularized areas. In most noses, the columella, or exterior septum, is the widest part of the nasal septum.

Figure 2G:
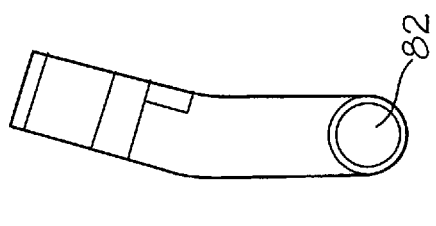
FIG. 2G provides a cross-sectional view of the alternative embodiment of FIG. 2F.
Figure 2F:
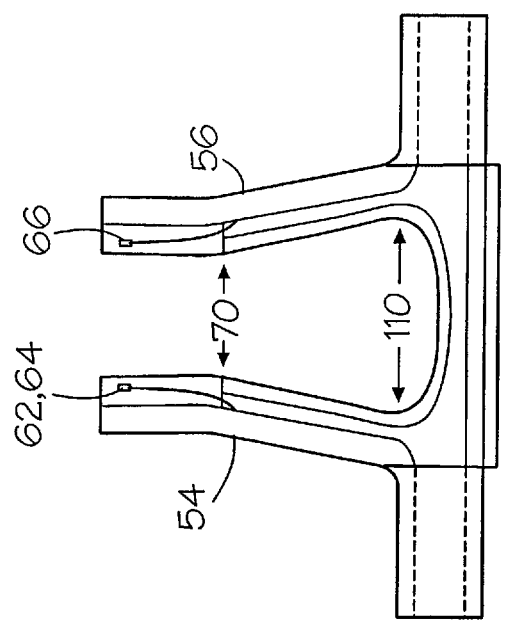
FIG. 2F provides a front view of an alternative embodiment of a nasal probe with a widened area to accommodate the size of the nasal columella.
Figure 2B:
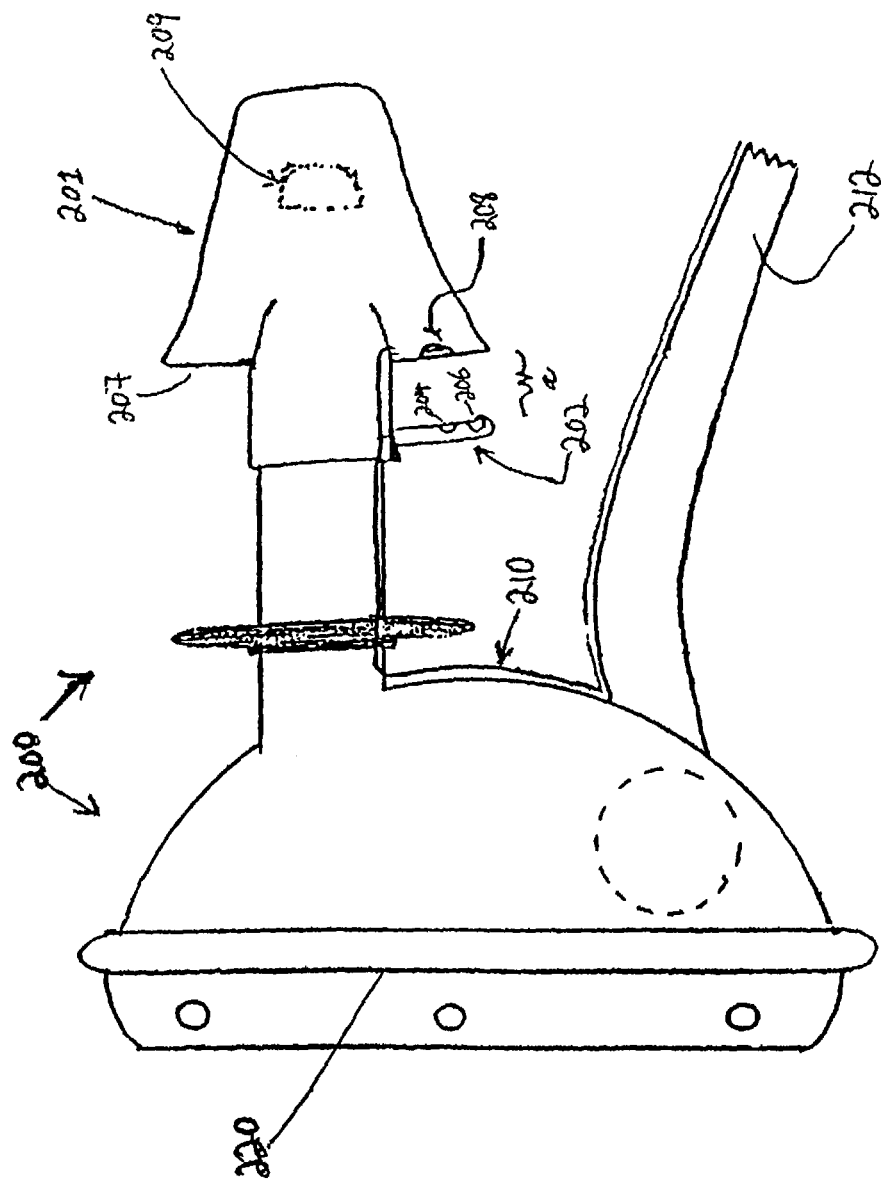

FIG. 2A is a top view, FIG. 2B is a side view, and FIG. 2C shows two cut-away views from a single mid-section line viewing opposite ends of the probe. From a main section, 52, of a resilient plastic housing, extend two extensions, 54 and 56, that are sized to enter the nares of the nose in similar fashion to a nasal cannula oxygen supply. These extensions, 54 and 56, are flattened in one dimension, as depicted in FIGS. 2A and 2B, and are shown angled at about 60 degrees in a second dimension, as viewed in FIG. 2C. This angle of inflection, 70, is properly drawn from a line drawn from one edge of the main section, 52. As discussed in greater detail below, the 60 degrees as depicted is not within the preferred range.

In specific embodiments depicted herein, two general approaches are used to protect the components of the pulse oximeter probe, 50, from moisture and contamination. Other approaches, as known in the art of medical device construction, also may be used. First, a clear plastic covering, shown as 61 in FIGS. 2A and 2B, and better viewed in FIGS. 2C and 2D, is placed over, to cover, each distal half of the two extensions, 54 and 56. It is noted that in the embodiment shown, the molded outer shell, 69, that forms and covers the main section, 52, also covers the approximately proximal half of the two extensions, 54 and 56, and the outer side of the upper, or distal halves of these extensions, but does not cover the front and rear sides, nor the inner sides, 65, of these extensions. To cover these exposed sides, a clear plastic covering, 61, is constructed, fitted over, and adhered to the existing components to form an integral protective exterior surface with the molded outer shell, 69. This is viewable in FIGS. 2C and 2D. Such plastic covering, 61, typically is manufactured by heat sealing pre-cut and/or pre-formed pieces, such as a cylinder or tube of heat-shrink plastic, to form a fitted covering over the distal halves of extensions 54 and 56. Then this is shrink-wrapped over the components of the distal half of the two extensions, 54 and 56. In the present embodiment, as depicted in FIG. 2A-D, after heat-shrinking a cylinder of heat-shrink plastic, 61, over each of the two extensions, 54 and 56, the distal end of this plastic is glued together to forms an end, 61E, over the distal end of each of the two extensions, 54 and 56. These ends, 61E, are viewed in FIG. 2C.

Also, typically these pieces of heat-shrink wrap plastic, 61, are sized and positioned to extend onto the approximate bottom half of two extensions, 54 and 56, by about $\frac{1}{16}$ inch, to form an integral seal against moisture (this overlap is shown at arrow X in FIGS. 2C and 2D). (It is noted that neither these nor other figures are drawn to scale, nor do they provide consistent proportions from figure to figure). In particular, FIGS. 2C and 2D show that a plastic cover, 61, is fitted over each of the circuit boards, 63, that contain the LEDs 62 and 64, located on extension 54, and the photodetector, 66, located on extension 56 (see FIG. 2C for details of LEDs 62 and 64, and photodetector 66). The plastic covers, 61, preferably do not interfere with light transmission in the critical wavelength ranges of the LEDs 62 and 64. Apart from heat-shrink sealing, other means of attaching the plastic covers, 61, to the extensions 54 and 56, include, but are not limited to, sonic welding, spot gluing, hot gluing, press fitting, and other such methods of attachment, as are employed in the art, that are used to attach components of a medical device for entry into an orifice of a living subject. Also, other means of providing a protective covering, such as are known to those skilled in the art, may be used instead of the above-described approach.

The above-described first protective approach is sufficient to prevent moisture and contamination of the components within the distal halves of the two extensions, 54 and 56. A second approach, which is an optional and not required for the operation of the pulse oximeter probe, 50, provides additional protection to this and other parts of the pulse oximeter probe, 50. This is shown in FIG. 2E. A protective sheath, 75, of clear plastic, is dimensioned to slip over the entire two extensions, 54 and 56, and then has flaps, 76, that loosely cover the main section, 52. The protective sheets are manufactured and priced so as to be disposable, so that after each use by a patient the protective sheath, 75, is slipped off the pulse oximeter probe, 50, and disposed of. Then the exterior surfaces of the pulse oximeter probe, 50, are wiped with alcohol or other suitable disinfectant. Then, prior to the next use, a new protective sheath, 75, is slipped over the indicated parts of the pulse oximeter probe, 50. Alternatively, the protective sheath, 75, is made of a material that will withstand repeated rigorous disinfection procedures (such as steam autoclaving) without deformation or degradation, such as is known in the art, and such protective sheaths are used on numerous patients, with a disinfection process conducted between each use.

In certain embodiments, the two extensions, 54 and 56, are spaced apart from one another so that, upon insertion into the nostrils of a patient, the inner sides, 65 of the extensions, 54 and 56, fit snugly against the tissue of each side of the septum, to avoid interference from ambient lighting.

Moreover, in certain embodiments, the relationship between the inner sides, 65, and the adjacent tissue of the interior septum is described as A non-contiguous fit as to the interior septum wall, such that, even considering irregularities of the nasal interior septum surface and patient movement, the inner sides, 65, do not make contact with the nasal interior septum mucosal tissue for most, or for all, depending on the patient, of the length of the respective extension's insertion into the nasal passage.

More particularly, a non-contiguously-fitting probe (such as 50, and its extensions, 54 and 56) is sized and constructed so that when placed into a nose size for which it designed (i.e., adult size, etc.), there is not a pressing or a continuous contact against the mucosal tissue of the interior nasal septum by both extensions where are positioned the light-generating components (such as LEDs 62 and 64) and the light detecting component(s) (such as photodetector 66). This contrasts with prior art that is disclosed to provide a continuous, even if light, pressure upon both sides of the interior nasal septum mucosal tissue, and/or that clips the probe against the mucosal tissue of the interior septum. Also, as to construction compared with the latter prior art example, the dimensions, materials and assembly of the present invention are such that there is not imparted to the two extensions, 54 and 56, an inward-flexing compressive force that causes attachment (as contrasted with incidental and/or partial contact) of the two extensions, 54 and 56, to the mucosal tissue of the nasal interior septum. Even more particularly, in part to avoid the possibility of irritation of the mucosal tissue of the interior septum walls, further, in certain embodiments, the entire surface of the inner sides, 65, from the inner faces, 67 (of the molded outer shell, 69) to the distal end of each extension, is planar and without any protruding areas, sections or components.

As to an example of the relative sizing between the thickness of the nasal interior septum and the span, 70, between the inner sides, 65, of opposing extensions, 54 and 56, FIG. 2D provides a diagrammatic representation. For an adult-sized nasal probe of this configuration, the span, 70, is 0.360 inches (9.1 mm) between the inner faces of extensions, 54 and 56. This is uniform inward, to and including where the LEDs 62 and 64 of extension 54, lie opposite the photodetector 66, of extension 56. Measurements of the interior septa of a number of adults with a caliper provides an average of about 0.250 inches septum thickness. The difference between 0.360 and 0.250 inches provides a sufficient gap to allow for the presence of deviated septa. Also, it has been found that this gap of 0.360 inches is sufficiently narrow so as to not allow ambient light, under normal circumstances, to impair the overall functioning of the pulse oximeter probe. Thus, for a typical adult-sized nasal probe of the present invention, a space of about 0.065 inches on each side, between the surface of the inner face, 67, and the mucosal tissue of the nasal interior septum has been found to provide a "non-contiguous fit."

Further, in certain embodiments of the present invention, the space between inner sides, 65, of opposing extensions 54 and 56, where the light-generating and the light-detecting components are positioned, for adult-sized probes, is between about 0.300 and 0.420 inches. In other embodiments, for such adult-sized probes, the space is between about 0.330 and 0.390 inches. In other embodiments, for such adult-sized probes, the space is between about 0.350 and 0.370 inches. Corresponding size ranges are within the skill of the art to determine for pediatric-sized nasal pulse oximeter probes comprising a non-contiguous fit, based on the measured thickness of the nasal interior septum for such pediatric patients, and the range of spacing given factors of comfort and probable incidence of ambient light interference (recognizing, for instance, that neonates have greater light transmission through their tissues).

In certain embodiments support for the distal ends of the inner sides, 65, generally is through contact with columella. This fleshy tissue extends laterally, to various extents in different individuals, from a plane generally defined by the surface of the more interior mucosal lining of the interior septum. The columella is less sensitive and less subject to damage by direct contact than that more interior mucosal lining of the interior septum. Thus, in embodiments such as that depicted in FIG. 2A-D, having substantially parallel inner sides, 65, when opposing parts of the respective inner sides, 65, fit snugly against the columella (i.e., the inner faces, 67, of the molded outer shell, 69), this helps position the more distal sections of the extensions to minimize or prevent continuous contact between these more distal sections and the interior septum mucosal lining. Also, when a particular patient's columella is being compressed by both inner faces, 67, this results in less pressure by any incidental contact by a more distal section of one or the other extension against the interior nasal septum mucosal lining. Without being bound to a theory, it is believed this is because the more outward section of that extension is in contact with and is being partially supported by the columella. Based on such analysis, contact of the nasal probe extensions, on one or both of the columellae, is less damaging to the patient than prior art devices that actually clamp to the more interior mucosal lining of the nasal interior septum.

Thus, when the extensions 154 and 156 fit snugly against the columella, and are not found uncomfortable over time by the user, this comprises one example of a good fit. Further, such bracing contact with tissue of the columella is not mutually exclusive with the fit described as non-contiguous. That is, in many uses, the same embodiment both contacts the columella with its extensions and, more interiorly, there is not a pressing or a continuous contact against the mucosal tissue of the interior nasal septum by both extensions where are positioned the light-generating components (such as LEDs 62 and 64) and the light detecting component(s) (such as photodetector 66). More broadly speaking, the same embodiment may both 1) provide a beneficial fit against the columella and 2) provide a non-contiguous fit more interiorly.

However, it has been observed that certain larger columellae, in certain patients, deviate outward the extensions of the nasal probe such that the distal ends of the two extensions, respectively bearing the light-generating and the light-detecting components, are positioned an undesirably long distance from each other. To deal with this, in other certain embodiments, each of the inner faces of the extensions comprise a deviation in the shape of the extension to allow for a relatively larger-sized columella. This is advantageous for persons having large columellae, so that their columellae do not force the extensions to spread outwardly to an undesirable distance from the interior nasal septum. In such embodiments, depending on the sizing of the nasal probe (see below) and the size of the patient's nose and columella, there might be no contact with the columella, in which case the support for the weight of the extensions is on the part(s) of the probe main section that is in contact with the upper lip. Where, given the respective sizes of probe and columella, there is contact, with such accommodation for the columella the spreading of the ends of the extensions is less than it would be otherwise.

FIG. 2F provides a side view, comparable with the view of FIG. 2B, of one embodiment of the nasal probes of the present invention that comprises a deviation in the shape of the extensions to allow for a relatively larger-sized columella. For an adult-sized nasal probe of this configuration, the maximum span, 110, is 0.500 inches (12.7 mm) between the inner faces of extensions 54 and 56. This is where the nasal probe main section, 52, and the two extensions, 54 and 56, meet, and the wider span is generally aligned to accommodate the width of the columella upon insertion of the nasal probe to its operational position. Further distal on the two extensions, 54 and 56, where the inner sides, 65, are shown in substantially parallel orientation, are found the LEDs 62 and 64 of extension 54 positioned opposite the photodetector 66, of extension 56. Along this substantially parallel length the span between the inner sides, 65, is 0.360 inches. This is shown as gap 70. Although this columella-widened embodiment in FIG. 2F is shown without a cannula, and without means for sampling exhaled gas for capnography, embodiments of nasal probes with such capabilities and features (discussed, infra) also may have a columella-widened aspect such as depicted in FIG. 2F.

FIG. 2G provides a cut-away view of FIG. 2F, showing a conduit, 82, within which are electrically conductive wires (or other types of signal transmission means, such as fiberoptic cable) to pass electrical signals to and from the two light-emitting diodes, 62 and 64, and the opposing photodetector, 166. Also apparent is the angle, or inward inflection, of the substantially parallel lengths of the two extensions, 54 and 56. A bend such as this, as discussed herein, achieves placement of the two light-emitting diodes, 62 and 64, and the opposing photodetector, 166, adjacent to a vascularized region of the nasal septum that advantageously provides superior pulse oximetry data.

Further, it is recognized that the flexibility of the nasal probe main section, 52, and the two extensions, 54 and 56, are important in achieving the operational performance of the nasal probes of the present invention. One nasal probe has been constructed with TPE plastic and had a measured flexibility of 60 durometer units. Another nasal probe, also made with TPE plastic, was manufactured and had a measured flexibility of 87 durometer units. In general, with regard to the plastic used for nasal probe main section, 52, and the two extensions, 54 and 56, the preferred range for plastic flexibility is between about 60 and about 90 durometer units.

Per the above, the distance between the probe extensions in relation to the average dimensions of the septa of the target patient group is one factor that provides for a suitable non-contiguous fit to obtain good pulse oximetry data without undesirable patient discomfort and/or tissue damage that results from a direct clipping of the probe extensions (arms) to the mucosal tissue of the nasal septum. Critical to this approach is not designing nor operating the nasal probe to applying pressure to, attach to, or clamp on to, the nasal mucosal tissue where the pulse oximeter readings are being taken. It has been noted that practitioners in the field have expressed the need to, and have practiced, applying pressure to a probe in order to stabilize the probe. While this may be required in finger or other extremity probes, this is contraindicated when considering the delicate mucosal tissue that lines the septum. Thus, in the present invention, the nasal probes, in their sizing, material selection, and overall design, are such that they perform to obtain pulse oximetry data by passing light through the nasal septum, and the probes do this without applying pressure to the nasal septum from both sides at the same time. That is, if any incidental contact is made to the actual nasal mucosal tissue from one extension, where either the light-generating or the light-detecting component is positioned, the other such area (where the light-generating or the light-detecting component is positioned) on the other extension is not then in contact with the opposing side of the nasal septum mucosal tissue.

In summary, the nasal pulse oximeter probes of the present invention are designed, sized and constructed to direct light against sensitive and highly vascularized mucosal tissue of the nasal septum without pressing against such tissue from both sides simultaneously, and to provide for long-term use with minimal irritation or tissue necrosis.

Another aspect of certain embodiments of the present invention is that the light-generating and the light-detecting components do not protrude from the respective planes of the inner faces of their respective extensions. This is consistent with the teaching of the present invention that there is neither a need nor a desire to press into the mucosal tissue of the nasal septum at the site adjacent to these components. In most embodiments, these components are positioned on respective diode pads. These pads are placed within the respective extensions, and as a result, in certain embodiments, are recessed within the respective extensions.

Further as to the specific construction of the embodiment depicted in FIG. 2A-D, using the shrink-wrapping construction described above to cover the distal halves of the extensions 54 and 56, and dimensioning the spacing between the extensions 54 and 56, so as to fit snugly against the tissue of each side of the septum, these are found to fit without irritation, as from a rough or uneven surface. For example, without being limiting, when using heat sealing plastic as the covering, 61, the thickness of this material, and any finish on the adjoining edge, will affect the extent of a sensible ridge at the junction of the covering, 61, and the molded outer shell, 69.

As to the specific area of the nasal septum that is preferred for use of a nasal pulse oximeter probe such as the one depicted in FIGS. 2A-D, it has been learned that the area of the nasal interior septum closest to the face (e.g., the proximal area of the middle alar), is more consistently vascularized and thereby provides more consistent and reliable signals than the areas more distal, i.e., the interior septum closer to the point of the nose. In particular, and more specifically, a highly vascularized region of the septum known alternately as Kiesselbach's plexus and Little's area, is a preferred target area for detection of blood oxygen saturation levels by a nasal pulse oximeter probe of the present invention. In the particular device shown in FIGS. 2A-D, an angle of inflection, 70, is shown between plastic housing, 52, and the two extensions, 54 and 56. This angle properly is measured as an interior (proximal) deviation from a straight line extended from the plastic housing, 52. In preferred embodiments, the angle of inflection, 70, is between about 0 and about 33 degrees, in more preferred embodiments, the angle of inflection, 70, is between about 10 and about 27 degrees, and in even more preferred embodiments, the angle of inflection, 70, is between about 10 and about 20 degrees. In FIG. 8B, the angle, 70, is about 15 degrees. This angle has been found to provide superior results in testing. Therefore, the angle shown in FIG. 2C, namely 60 degrees, is not a preferred angle of inflection.

Thus, in general, the two extensions, 54 and 56, are angled so that upon insertion and proper placement into position in the nostrils, the LEDs 62 and 64, located on extension 54, emit light directed through a region that includes the preferred, proximal area of the nasal septum. Most preferably, the LEDs 62 and 64, located on extension 54, directed light exclusively through the highly vascularized region of the septum known alternately as Kiesselbach's plexus and Little's area.

In addition, a stabilizer, 58, embodied in FIG. 1 as a flat plate flush with and extending downward from the inside edge of the lower plane of the extensions 54 and 56 (before the extensions angle inward, see FIG. 2C), is designed to press against the area between the upper lip and nose to hold the desired position of the probe, 50, and in particular the LEDs 62 and 64, in relation to preferred, proximal area of the nasal septum. The stabilizer, 58, alternately previously considered part of a preferred embodiment but not a necessary component, and, on later testing, to irritate many users, is now considered to be valuable when properly oriented in relation to other components of the probe, 50. Additional means of stabilizing the probe, 50, such as elastic straps from any part of the device that span the head of the patient, may be employed with or separately from the stabilizer, 58. Thus, in preferred embodiments, no stabilizer, 58, is used, and the design of the device, as shown in other figures provided herein, with or without additional stabilizing means, are adequate to stabilize the probe, 50, during normal wear.

As for the probe described above in FIG. 1, timed electrical impulses from a pulse oximeter monitor system pass through two wires (not shown) in cables 61R and/or 61L to produce the light from LEDs 62 and 64. At least one photodetector, 66, is positioned on extension 56 to face and oppose LEDs 62 and 64 of extension 54. The photodetector 66, which typically is a light-sensing photodiode, detects changes in the light emitted by the LEDs 62 and 64 as that light is differentially absorbed between and during pulses across the capillaries of the septum tissue between the two extensions, 54 and 56. In one embodiment, LED 62 emits light around 650-670 nm, and LED 64 emits light around 880-940 nm. The electrical impulses are timed to be offset from one another. The photodetector, 66, detects the light passing through the septum of the nose, which is situated between extensions 54 and 56 when the probe 50 is in use. As discussed above, loss of signal through vascularized tissue such as the nasal septum is due both to background tissue absorption and the absorption by the blood in the arteries, which expands during a pulse. The signals from photodetector 66 pass through conductors (not shown) to the processor of the monitor system (not shown). The "signal" as used here, is meant to indicate the signal from a photodetector receiving light from one or more light sources of the pulse oximeter probe, which provides information about differential absorption of the light during different parts of the pulse. These signals are to be distinguished in this disclosure from signals (electrical impulses) that are sent to the light sources to emit light, and from control signals that are sent, in certain embodiments, to control a valve to supply more or less gas to a system.

Cables 61R and 61L preferably form a loop that may lie above the ears of the patient, and join to form a single cable (not shown). This single cable preferably terminates in an electrical plug suited for insertion into a matching socket in the pulse oximeter monitor system (not shown). In another preferred embodiment, the single cable terminates by connecting to an adapter cable, which in turn connects to a socket in the pulse oximeter monitor system (not shown). In a typical application, the signals from the light-sensing photodetector, 66, are ultimately received and processed by a general purpose computer or special purpose computer of the monitor system (not shown). As used herein, the terms "monitor system" and "monitoring system," may refer to the component that receives data signals from one or more probes, that is, the component that comprises the general or specific-purpose computer that analyzes those data signals (i.e., the processor). This may be a stand-alone unit (i.e., a console or, simply, pulse oximeter), or a module that transmits data to a central system, such as a nurse's station. However, depending on the context, the terms "monitor system" and "monitoring system" also may encompass the entire assemblage of components, including such component and the one or more probes and the conductors (i.e., connecting wiring) that transmit data and control signals.

Also, it has been learned that a nasal probe, such as 50 in FIG. 2A-D, fits better and is found more comfortable by a patient when the cables are glued to the main section, 52, of the body of the probe, 50, in the following way. This method takes advantage of the natural bend in cable (and tubing) that comes from the rolled storage of such material on a spool. That is, wire, cable, tubing and the like that are rolled onto spools have a natural bend imparted thereby. It has been learned that if this bend is disregarded when assembling the cable sections to the main section, 52, then, for many nasal probes assembled with cables that go over the ears when in use, the probe, 50, and particularly its extensions, 54 and 56, will have a tendency to rotate axially (in relation to the cable crossing the lip laterally) outward or inward. This leads to discomfort, effort to readjust, and, at times, poor data acquisition. To solve this problem, a section of cable long enough for both sides of the probe is cut and placed unobstructed on a flat surface. The natural bend from the spool configures this section in a curvilinear shape, typically nearly forming a circle. The two ends of this section of cable are inserted into the respective holes for these in the molded flexible plastic that comprises the main section, 52, of the probe, 50 (an arrow in FIG. 2E points to a hole filled by a cable). The contiguous extensions 54 and 56 (typically part of the same molded piece as the main body, 52), are positioned flatly against the flat surface, so the desired inward inflection (i.e., of 15 degrees) is directed toward that flat surface, and preferably so the most inward points of the extensions 54 and 56 (i.e., those that will be farthest in the nose when in operational position) contact the flat surface. In this position, the cables are adhered or otherwise secured to the main section, 52, of the probe, 50. Typically, this is done by application of a liquid adhesive to the holes where the cable ends enter the main section, 52 (i.e., see arrow in FIG. 2E). The cable then is cut to provide two lengths, each one attached to one side of the main section, 52.

When this method is practiced, due to the natural bend of the rolled cable (or tubing), the resultant cables 61R and 61L, when placed over the ears, tend to gently orient the probe extensions, 52 and 54, axially inward, toward a desired vascularized part of the nasal septum. As such, comfortable nasal probes are produced, and the probes are more easily adjusted to desired positions. Also, it has been observed that probes made this way more generally maintain their desired positions, and this is believed due to there being no undesirable countervailing force (i.e., the rotational force of some cables not assembled per this method) against whatever means are used to keep the probes in place.

Further with regard to embodiments of the nasal probe that provide a non-contiguous fit when inserted into a nose of a patient, use of such probes thusly to obtain photoplethysmographic data unexpectedly provides superior results in comparison to prior art methods that simultaneously press (albeit lightly) both sides of the interior nasal septum, or, more severely, that grasp the nasal septum in such a way that there is contact on both sides of the nasal septum at the same time with both the light sources and the light detector. That is, an improved method for obtaining pulse oximetry and other photoplethysmographic data is described as follows:

a) Through size estimation of the nasal septum to be used for data collection, providing a nasal probe for insertion around the septum such that said probe non-contiguously fits said septum;

b) Inserting one extension of the nasal probe into each of the two nostrils of a patient, wherein one extension comprises at least two light-generating components that emit light at at least two different wavelength bands, and the other extension comprises at least one light-detecting component that detects light transmitted from said at least two light-generating components; and c) Measuring, selectively, pulse oximetry and/or other photoplethysmographic properties of the blood flow in vascularized interior septum tissue positioned between said at least two light-generating components and said at least one light-detecting component;

d) Wherein said blood flow is not dampened by a simultaneous pressing of said tissue from both sides at the point of measurement of said data.

Among other benefits, the data taken from the less dampened (compared to finger probes) vascularized tissue of the interior nasal septum provides more distinct signals having clearer information about cardiovascular parameters.

Further, it is noted that such method optionally additionally includes locating a desired highly vascularized arterial plexus, such as Kiesselbach's plexus, for the point of measurement, such as by using perfusion index locating means, detection by lower LED power requirement, or other means known in the art.

Further with regard to embodiments of the lip/cheek probes, use of such probes to obtain photoplethysmographic data provides superior results. That is, an improved method for obtaining pulse oximetry and other photoplethysmographic data is described as follows:

a) Through size estimation of the thickness of the lip or cheek to be used for data collection, providing a lip/cheek probe dimensioned for insertion around the lip or cheek so as to not squeeze the tissue, to avoid constriction of blood vessels therein (such constriction measurable by comparative data with probes having different distances between the pads);

b) Placing the distal arm of said probe into the mouth to a desired position; and c) Measuring, selectively, pulse oximetry and/or other photoplethysmographic properties of the blood flow in vascularized tissue positioned between said at least two light-generating components and said at least one light-detecting component.

In particular, it is noted that the probe, after initial placement to a desired position, is adjusted to a more desired position providing a good signal. This is done such as by comparing signals from the different possible positions. Thereafter the cable leading from the probe (which typically is placed over the top of one ear) is taped to the outside cheek to stabilize and maintain this selected position. It has been found that a desired positioning often is with the bridging section, 2, of the probe positioned in or near one corner of the mouth, with the cable leading over one ear. In such positioning the light-generating and the light-detecting components are positioned around an area of the cheek a distance from the corner of the mouth. It is noted that the lip/cheek probe has been found to function consistently, without interference from movement of the mouth, in patients who are under anesthesia or on sedating medications. This is not meant to be limiting, as other uses are considered appropriate, taking into account, as needed, a possible effect of mouth movement and resultant interference of signals during periods of such movement.

In a variation of the nasal probe, such as is exemplified in one embodiment in FIG. 2A-D, oxygen is delivered with the same device that also measures trans-septum arterial oxygen saturation (see FIG. 8A,B). In another variation, the pulse oximeter sensor is independent of an oxygen cannula, and is a single-use unit. In yet another variation, the pulse oximeter sensor is independent of an oxygen cannula, and is re-usable and readily cleanable with appropriate antiseptic cleaning agents. Other variations within the scope of the invention described and pictured can be developed by those of ordinary skill in the art.

Figure 3:
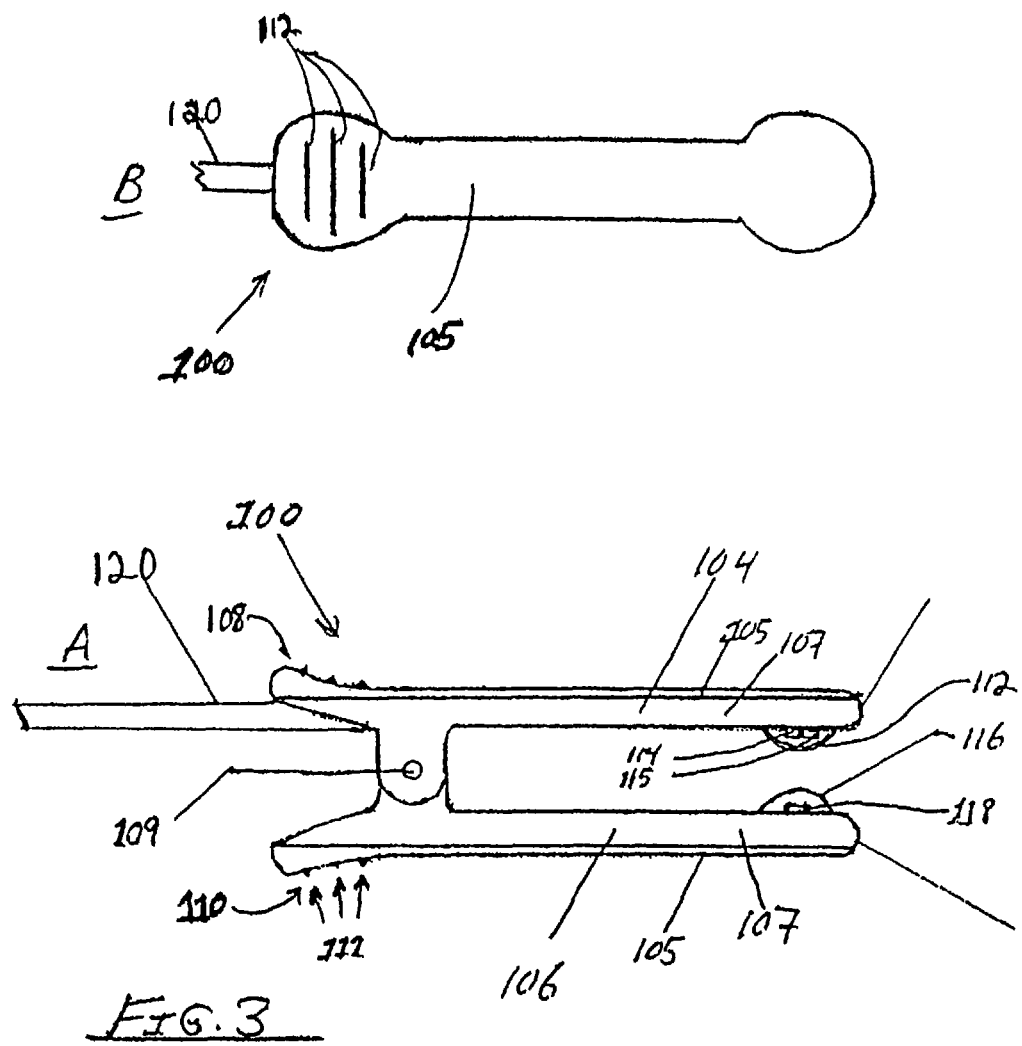
FIG. 3A,B depicts a side view and a top view of a pulse oximeter probe for positioning on the tongue of a patient.

FIG. 3 illustrates a third pulse oximeter probe, 100, of the invention, that is configured for placement on the tongue of a patient for measurement across the vascularized tissue of the tongue. The probe, 100, has two substantially flat opposing arms, 104 and 106. A housing cover, 105, is joined with a housing base, 107, to form each of the two arms, 104 and 106. At one end of each of the two arms, 104 and 106, are finger pads, 108 and 110, which in the embodiment shown in FIG. 3 are on the housing covers, 105, and possess ridges, 111, to improve the grip.

The arms, 104 and 106, are tensioned to close against one another by a spring (not shown) which has a fulcrum at or near an axle, 109, that hingedly connects the two arms, 104 and 106, near one end. At or near the other end is an LED pad, 112, on one arm, 104. Within this pad, 112, are two light generating sources, here shown as LEDs 114 and 115. Opposite this housing, 112, on arm 106, is a photodetector pad, 116. Within this pad, 116, is at least one photodetector, 118. Electrical wire conductors (not shown) connect the LEDs, 114 and 115, and the photodetector, 118, to a pulse oximeter monitor system (not shown), via a cable, 120, passing from one end of the arm, 104. The inner surfaces of the arms, 104 and 106, in some variations of this probe are knobby or otherwise textured, especially around the LED pad, 112, and the photodetector pad, 116. This texturing is designed to better maintain a stable position of the probe, 100, on the tongue without use of excessive pressure of the spring.

The photodetector 118, which typically is a light-sensing photodiode, detects changes in the light emitted by the LEDs 114 and 115 as that light is differentially absorbed between and during pulses across the capillaries of the tongue tissue between the two arms, 104 and 106. In one embodiment, LED 114 emits light around 650-670 nm, and LED 115 emits light around 880-940 nm. The electrical impulses are timed to be offset from one another. The photodetector, 118, detects the light passing through the tongue which is situated between the first housing, 112, and the second housing, 116 of arms 104 and 106 when the probe 100 is in use. As discussed above, loss of signal through vascularized tissue such as the tongue is due both to background tissue absorption and the absorption by the blood in the arteries, which expands during a pulse. The signals from photodetector 118 pass through conductors (not shown) housed in cable 120 to the processor of the monitor system (not shown). Cable 120 preferably terminates in an electrical plug suited for insertion into a matching socket in the pulse oximeter monitor system (not shown). In another preferred embodiment, cable 120 terminates by connecting to an adapter cable, which in turn connects to a socket in the pulse oximeter monitor system (not shown). In a typical application, the signals from the light-sensing photodetector, 118, are ultimately received and processed by a general purpose computer or special purpose computer of the monitor system (not shown).

There are numerous means for hingedly joining the first arm and the second arm other than by an axle passing through the extensions of each arm (e.g., by axle 109). Other means include hinges of various materials and designs as known in the art, co-fabrication of the arms with a thinner section of flexible plastic between the two arms at one end, and pins, screws, and other fasteners as are known to those skilled in the art.

Similarly, means for tensioning the first arm and the second arm, so as to properly maintain tension on a section of the tongue of a patient, can be effectuated by means other than the spring described above. Separate elastic bands may be attached or may surround the arms, such as by attaching to protrusions spaced appropriately along the arms. Also, the natural flexibility and resilience of a co-fabricated structure comprising both arms connected by a section of resilient plastic can provide both the means for hinging and the means for tensioning. Such fabrications may be deemed suitable for disposable units.

It is noted that for this and other probes disclosed herein, a single source generating at least two different light frequencies may be utilized instead of LEDs. Alternately, more than two LEDs may be used, such as to generate light at more than two frequency bands, for instance to increase accuracy and/or detect other forms of hemoglobin. Also, light receiving sensors, or photodetectors, other than photodiodes may be used, and more than one such sensor may be used in a single probe.

The pulse oximeter probes, such as 10, 50, and 100 as depicted and as used with the monitoring systems in the present invention, take measurements by transillumination as opposed to reflectance. This is the preferred configuration. However, for any of these probes, both the light-generating devices, and the photodetector devices, can be configured adjacent to one another, on one arm or extension, to measure reflectance of the tissue on the interior of the mouth (e.g., the cheek), the lip, the nasal septum, or the tongue.

Figure 4:
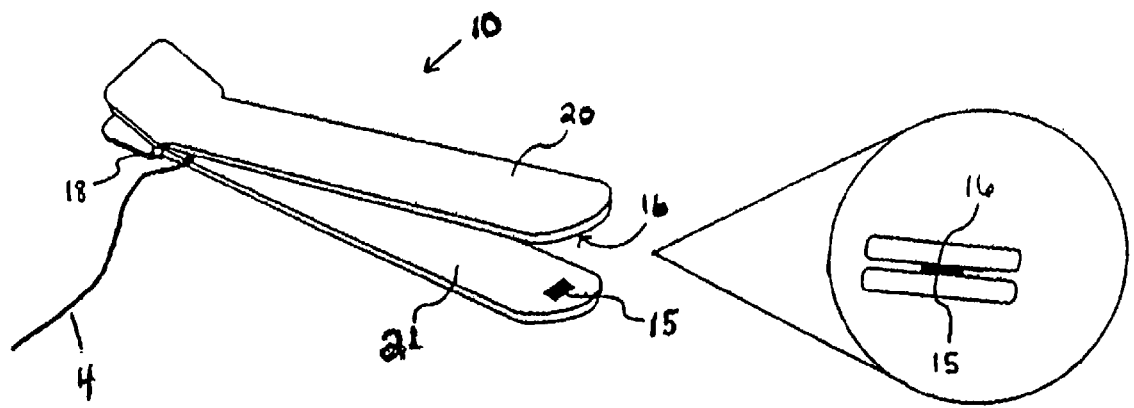
FIG. 4 illustrates a perspective angled side view and an exploded frontal cross-sectional side view of a flat surfaced, elongated spring-loaded pulse oximeter probe showing the configuration of the LED's and the photodiode detector according to the present invention.

FIG. 4 depicts another general configuration of an oximeter probe of the present invention. This probe 10 can be dimensioned and configured to be expandable and tensioned to close by a spring, 18. Near the distal, operative end of one substantially flattened side, 20, is an LED array, 16, and opposing it near the distal, operative end of the opposing substantially flattened side, 21, is a light detecting sensor, preferably a photodiode, 15. A cable, 4, connects the LED array, 16, and light detecting sensor to a pulse oximeter monitor system (shown in the magnified end view)). This pulse oximetry probe can be used to measure pulse-based differences in light absorbence across vascularized tissue of a patient in a number of locations, including but not limited to the cheek, the lip, the nasal alars (alar nari), the nasal septum, fingers, and toes.

By "substantially flattened" is meant that the height of the structure of a side is small relative to the greater of the length or width of that side. Preferably the ratio of the height to the greater of the length or width of a "substantially flattened" side is between about 0.2:1 and 0.001:1, more preferably this ratio is between about 0.02:1 and 0.005:1, and yet more preferably this ratio is between about 0.01:1 and 0.005:1. For greater applicability to typical physical requirements in use, each side also is substantially longer than wide. By "substantially longer than wide" is meant that the width of the structure of a side is small relative to the length of that side. Preferably the ratio of the width to the length of a side described as "substantially longer than wide" is between about 0.7:1 and 0.02:1, more preferably this ratio is between about 0.025:1 and 0.05:1, and yet more preferably this ratio is between about 0.025:1 and 0.1:1. At a minimum, with regard to nasal pulse oximeter probes of the present invention, the key functional attributes of extensions that are substantially flattened and/or substantially wide, as used herein, is that the width of such extensions is sufficient to house the components (i.e., circuit boards bearing LEDs and photodetectors, or the LEDs and photodetectors themselves), and the length of such extension is sufficiently long to provide the LEDs and photodetectors on opposite sides of a desired region of vascularized tissue. The same functional logic applies to other sensors disclosed and claimed herein.

Also, it is noted that in place of the spring, 18, any hinging means as known in the art can be used. Such hinging means may include a raised section along or separate from the sides, such that a fixed space is created at the point of the hinging means. This would obviate the need for a bend in the sides at the spring, 18, as shown in FIG. 4 (which is required in FIG. 4 to lever open the operative ends). These substantially flattened probes are configured such that the inner faces of both sides substantially oppose each other and, based on the spacing and configuration of the hinging means, are sufficiently separable to widen to encompass a desired tissue to be monitored for blood oxygen saturation between the light emitting structure and the light detecting structure at the operative end. It is noted that these structure may each be enclosed in a pad, or may not be so enclosed. As for other probes disclosed herein, a monitoring system connected to the probe modulates light signal production and receives signals of light detected by at least one light-detecting structure positioned at the operative end of one of the sides, such as 20 or 21 in FIG. 4. Typically a pulse oximeter or photoplethysmography monitoring system console includes, or can be connected to, a video monitor that provides graphical and numerical output from the signals received from the photodetector, which are algorithmically processed by a special-purpose (or general-purpose) computing component in the monitoring system console.

Figure 6:
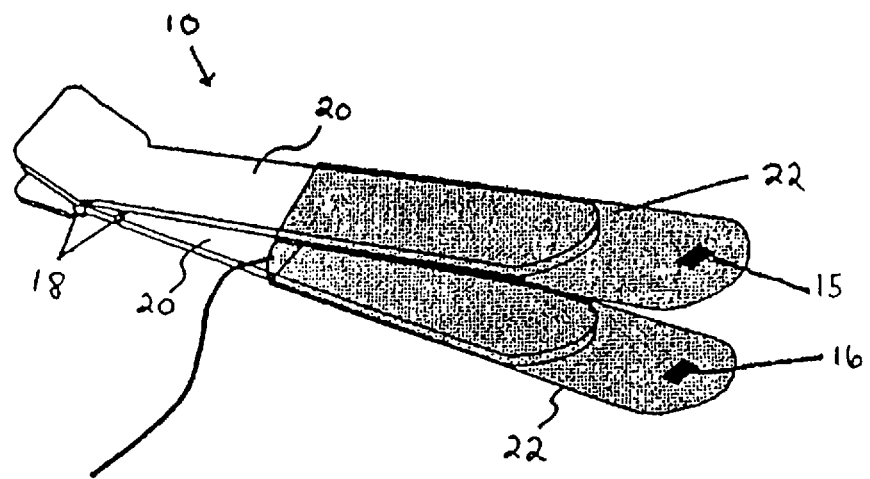
FIG. 6 illustrates a perspective angled side view of a flat surfaced, elongated spring-loaded pulse oximeter probe showing the features of the pulse oximeter sheath according to the present invention.

Also, the above substantially flattened sides with hinging means may be produced without light-emitting and light-detecting structures, and sleeves, such as described below, bearing such structures, would then be slipped over the sides to yield an operable oximeter probe. For instance, as shown in FIGS. 4 and 6, a probe 10 with a flat surface 20 is suitable for to receive a flexible sleeve, 22, that bears an LED array, 16, and light detecting sensor, preferably a photodiode, 15. This slips over the flat-surfaced structure, as shown about halfway on in FIG. 6. As for the probe in FIG. 4, a cable, 4, connects the LED array, 16, and light detecting sensor to a pulse oximeter monitor system (not shown).

Figure 5:
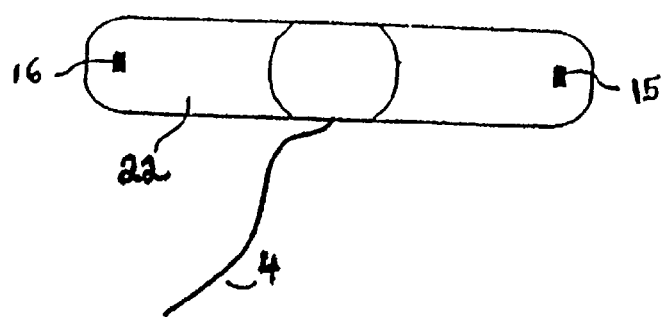
FIG. 5 illustrates an internal view of the pulse oximeter sheath according to the present invention.

In operation, the devices depicted in FIGS. 4-6 are placed around a finger, earlobe, or other extremity in order to obtain data.

Thus, another aspect of the present invention is a disposable sleeve that fits over any of the pulse oximeter probes disclosed and claimed herein, and over conventional probes. A sleeve is constructed of a flexible material, and is relatively thin, in the general range of 0.005 to 0.050 inches thick, more preferably in the range of 0.010 to 0.025 inches thick, and most preferably in the range of 0.010 to 0.015 inches thick. The sleeve is manufactured to slide over the major structural features of the probe to provide a barrier to reduce the chance of contamination from one patient to a second patient using the same probe. An example of such sleeve is shown in FIG. 5, and its implementation over a probe is shown in FIG. 6. In this case the sleeve is constructed to include the light generating and the light sensing features, and associated conductors. However, in other embodiments of the sleeve, such features are on the major structural features, whether frames, arms, etc., and the sleeve slides over such features, and at least in the areas of such light producing and light sensing features the sleeve is highly transparent to the critical wavelengths used by the pulse oximeter. The sleeves cover both arms, or extensions, of probes having two distinct arms. Preferably a continuously integral section of the sleeve joins the sleeve sections that cover both arms or extensions of the probe, in order to, inter alia, protect the intervening parts of the probe. For a probe such as the probe of FIG. 1, the sleeve is configured to the shape of the probe and slides over starting at the end, 4, of the arm, 3, and covers up to, and preferably including, the boot, 8.

In some sleeve embodiments, a stretchable aspect of one or more parts, or of the entire sleeve, stretches over a protuberance or other prominence at one or more parts of the major structural features over which the sleeve is sliding, and improves the fit of the sleeve. This also better assures that the sleeve does not slide off the probe during normal uses. Alternate means to secure the sleeve onto the probe such as are known to those of skill in the art may be used. The sleeves themselves can be disposable; however, the sleeves also can be made of easily sterilizable materials and be sterilized between uses.

The probes and the sleeve covers of the present invention are supplied as clean or as sterile, depending on the needs of the end user and the budgetary constraints of the end user. Clean but not sterile probes and sleeves will be less expensive, and may be suitable for many applications. Where there is an elevated risk of major harm from an infection, for instance in immunocompromised patients undergoing transplants with immunosuppressive drugs or undergoing chemotherapy, sterile probes would be more appropriate than merely clean probes. Many configurations of the probes are cleanable using alcohol and/or detergent/disinfectant solutions, and other configurations are disposable.

All of the above disclosed probes operate in a typical manner of a pulse oximeter, as described herein and in articles and patents cited and incorporated by reference. Each LED emits its specific frequency hundreds of times per second, and the absorption (or transmittance) readings by a sensor, such as a photodiode, are transmitted to a computer. There a software system performs averaging (optionally deleting outliers), and by differences in wavelengths' absorption or transmittance at the pulse peaks, determines arterial oxygen saturation. In a standard two-LED system, this is done by an algorithm that calculates the ratio of the peak absorbence at 650-670 nm divided by the base absorbence at this wavelength range, and compares this ratio to the peak absorbence at 880-940 nm to the base absorbence at the 880-940 nm range. The base absorbence reflects the non-pulse background absorbence by tissues other than the artery at maximum width during the pulse. This calculation provides an estimate of arterial oxygen saturation. A graph of the pulse surge, or shape, over time, also can be obtained.

All of the above-disclosed probes are expected to have significant use in the intensive care units, operating rooms, post-surgery recovery rooms, and in ambulance related situations where a patient in need of monitoring has few suitable monitoring sites. The size and shape of each probe will depend on whether the patient is an adult or child.

When two or more probes are used together, data from multiple probes is processed to provide continuous and simultaneous cross-site comparisons of the arterial blood oxygen saturation status at and comparisons between two or more tissue sites (and, as desired, blood pressure estimates based on transit time differences and/or other related parameters). The monitoring system receiving these signals includes at least one program containing computer software (not shown) comprising instructions which causes the computer processor to receive and calculate various oxygen saturation values. Optionally, the monitoring system may receive signals from separate probes or sensors to assess blood pressure values, which optionally may be compared (either simultaneously or separately) with blood pressure estimates based on signals received from each of the probes determining arterial blood oxygen saturation and vascular perfusion/resistance of a patient. Depending upon the software used, and the addition of separate blood pressure probes or sensors, the monitor may be used as a dual pulse oximeter, a saturation difference monitor, a transit time monitor, a periodic blood pressure monitor, or a noninvasive continuous blood pressure monitor. Specific examples are provided below that demonstrate a non-exclusive range of applications for the monitoring system which compares signals from a central source site (CSS) with signals from at least one advantageously positioned peripheral site (PS), as those terms are defined herein.

Figure 7:
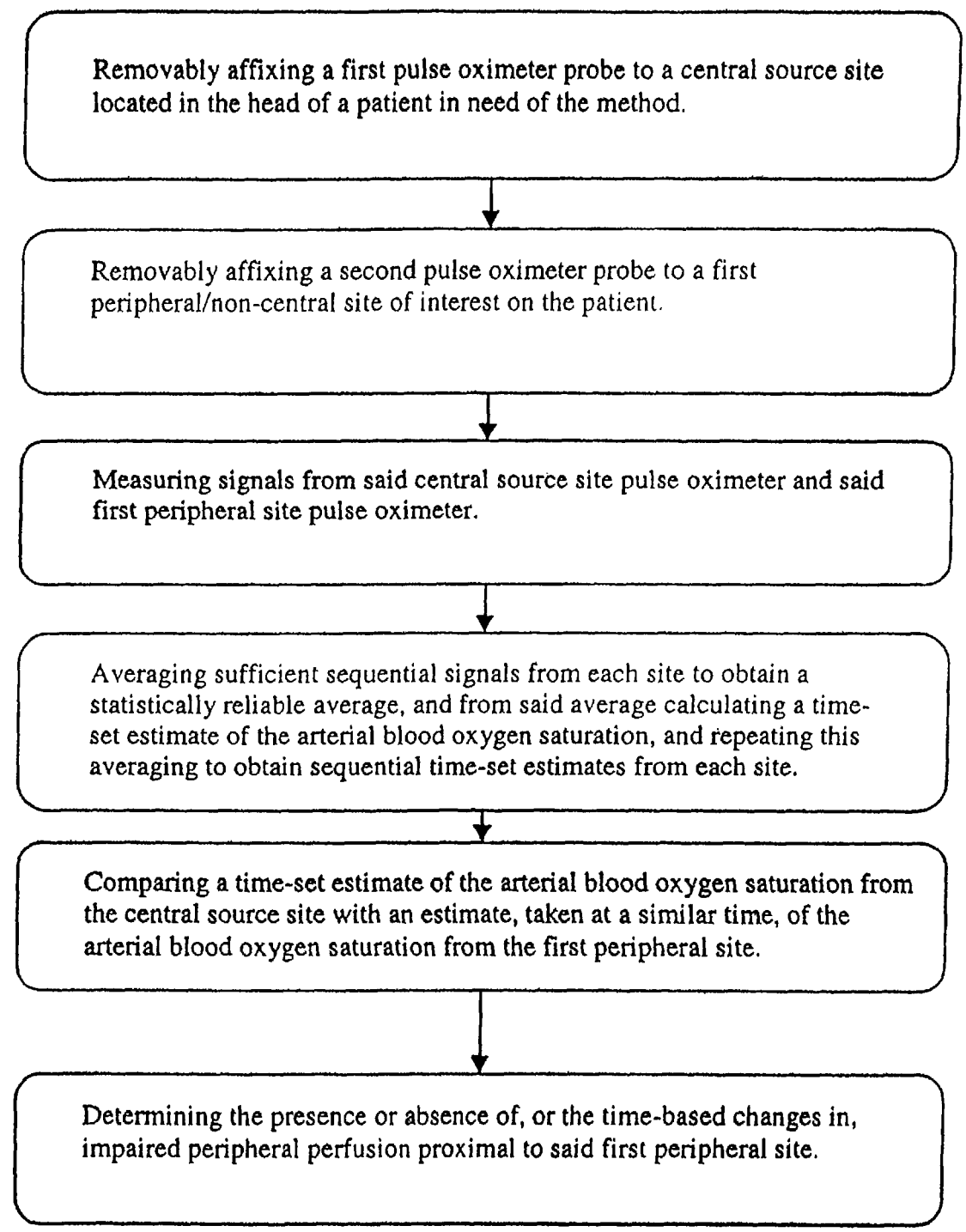
FIG. 7 is a flow chart showing one method utilized by the non-invasive vascular perfusion/resistance monitoring system to measure oxygen saturation values according to the present invention.

FIG. 7 depicts the steps of a basic method using the monitor system that includes one probe positioned in a CSS, and one probe in a PS. A first pulse oximeter probe is removably affixed to a CSS in the head of the patient. This is most preferably any of the specially configured probes, or could be a conventional probe. A second pulse oximeter probe is removably affixed to a PS such as a finger or a toe. This can be any of the specially configured probes, or a conventional probe. The monitoring system is started, the LEDs or other light generating sources in the probes emit designated light at designated frequencies and periodicities, and signals from the CSS and from the PS are measured and transmitted to the monitoring system computer. Here, adjacent signals of the same type (wavelength and probe) are averaged to obtain a statistically reliable average. As appropriate based on the software program, certain outliers as may be caused by movement of the patient, light contamination from an outside source, etc., are eliminated from consideration. The averaging is repeated and the averaged values are compared based on the time sequencing of the respective averages. That is, average values from a specific time from the CSS probe are compared to average values from the same time span from the PS probe. The software calculates arterial blood oxygen saturation percentages based on the differential absorption of the different species of hemoglobin, and percent oxygen saturation at the CSS and the PS are compared. Based on criteria input into the monitoring system and reflected in the software's calculations, the presence or absence of impaired peripheral perfusion are shown as an output reading of the monitoring system. Alternatively, if impaired perfusion has already been established, the tracking of time-based changes in the saturation differences between the CSS and the PS are read out or charted.

The method shown in FIG. 7 is conducted with an apparatus having the stated functional capabilities. Also, an oximeter monitoring system has the basic physical components that perform the required centralized functions, and which is attached to at least two oximeter probes to perform the above-described method.

Further, a variation of the method of FIG. 7 is to have an additional PS probe, and compare not only the first PS probe to the CSS probe, but to also compare the first and second PS probes' signals to one another. This can, for instance, demonstrate impaired peripheral perfusion in one body area, but not in another body area or extremity.

The apparatuses, methods and systems of the present invention can be applied to both humans and animals, i.e., to living vertebrate organisms. Its application in human medicine (adult & pediatrics) would significantly improve the estimation of vascular perfusion or resistance by pulse oximetry; however, veterinary medicine also would greatly benefit from its use. This superior monitoring system would utilize at least two pulse oximeter probes, one of which is designed for use with a highly perfused central tissue, such as a lip, tongue, nares, cheek; and the other probe is designed for use to less perfused areas such as peripheral tissues, or any combination thereof.

The following specific examples are meant to be demonstrative, but not limiting, of the possible applications of the present invention.

EXAMPLE 1

Data from a small number of volunteer subjects was obtained. This data provided preliminary support for the hypothesis that differences in CSS and PS estimates of arterial blood oxygen saturation levels can provide diagnostic information about the status of peripheral blood circulation. These data are summarized below.

All sets of data were taken three times, except that data for subjects 1 and 9 were only taken two times (duplicate data sets). Subjects 1-3 had no history of chronic obstructive pulmonary disease or other conditions that would be expected to cause lowered peripheral circulation. Except for one reading of 93% for subject 1, all estimates of arterial oxygen saturation were 95% or higher, and the PS (a finger, using a standard commercial probe) readings were within two percentage points of either CSS sites (lip and cheek). For the data set in which subject 1's cheek probe reading was 93%, the lip reading was 98% and the finger reading was 96%. Overall, the data of subjects 1-3 suggest that in a healthy subject the CSS and PS readings taken at or near the same time will be relatively close, within about 5 percentage points or less, and all of the readings will be high.

Subject 4 had average readings at the PS finger site of 89%, and at the CSS cheek site, 88.7%, so these sites has essentially identical estimates. No signal was recorded at the lip CSS. Although there was no difference between the CSS cheek and the PS readings, the oxygen estimate was low and indicated a generalized problem.

Subject 5 had a PS average of 85%; the lip CSS average was 88.3%, and the cheek CSS average was 91.3%. The absolute levels are low, and the difference between CSS and PS values ranges from about 3 for the lip to about 6 for the cheek. This appears to suggest a peripheral circulation problem, and the low absolute levels indicate a generalized problem with oxygenation. This subject was known to have COPD.

Subjects 6-8 were known to have COPD. The average values for finger, lip and cheek were 85, 90, and 89, respectively for Subject 6. The 4-5% less percent saturation for the peripheral site supports the present hypothesis. Subject 7's finger data varied between 77-80% during the readings, and is considered unreliable. One of subject 8's data points for the finger was 79%, whereas the other two were 85%. This suggests that the 79% reading is erroneous. Disregarding this data point, Subject 8 had 85%, 87.3%, and 85.6% averages for the finger, lip and cheek sites, respectively. Here, all readings are fairly close, and the absolute values are alarmingly low. The data from this subject do not support the hypothesis; however the circulation for this subject may not be impaired peripherally. Further investigation can resolve this and other points.

Regarding the latter, subject 11's data was anomalous in that the finger site averaged 93.3%, whereas the lip and cheek sites averaged 90.7% and 86.7%, respectively. The reason for this is unknown; the data could be spurious or could indicate unusual circulation in a small percentage of the population. Individual differences in circulatory systems (based in part on genetics, and in part on non-genetically based embryological development, and on physical conditioning) may form the basis for such anomalies in a percentage of the population. Highly variable and incomplete data for Subjects 9 and 10 were considered to render the value of their data questionable, and those data were not analyzed.

Thus, this preliminary data provided some indication of differences between CSS and PS and differences between normal and circulation-compromised subjects. The data also supported the need to investigate broader populations with known circulatory conditions to develop more predictive guidelines for the probe data differences. Even with the limited data of this example, it is apparent that the comparison of CSS and PS sites can provide a useful assessment of the state of the circulatory system even where there is no major difference, and there is not a disease state presenting itself. That is, such results of roughly equivalent CSS and PS data at a high oxygen saturation level would support a conclusion that the peripheral circulation is not impaired.

EXAMPLE 2

An elderly patient with relatively advanced diabetes comes in for monitoring of the status of perfusion in the right leg, which is diagnosed with severe atherosclerosis and related impaired vascular perfusion. A monitor of the present invention is utilized, with one CSS probe measuring signals across the nasal septum, and a PS probe on the large toe of the right foot. A new medication is started, and ongoing weekly data from the monitor tracks the changes in perfusion in the right leg by comparing oxygen saturation values of the CSS probe with the values of the PS probe. Such data indicates the degree of effectiveness of the new medication.

EXAMPLE 3

A critically burned patient is brought into an emergency room. As vital signs and assessment is taking place, a pulse oximeter probe as shown in FIG. 1 is placed into the patient's mouth to read cheek tissue as a central site source, and a pulse oximeter probe as shown in FIG. 4 is placed at each of the patient's large toes. Within less than one minute, the monitor of the present invention indicates below normal blood perfusion in the right leg, based on the signals from the probe placed on the right toe, compared to the central source site and the left toe probe. A probe is placed on a right finger, and this provides comparable data to the left toe. The attending physician is able to surmise that an injury or disease condition is adversely affecting perfusion in the right leg, orders more detailed testing, and increases the percent oxygen on the respirator to counter the low oxygen in the affected leg. The monitoring system tracks changes in the oxygen saturation values of blood in the right toe as this initial treatment has an effect.

EXAMPLE 4

A patient suspected of having Chronic Pulmonary Obstructive Disease is admitted to an emergency room with breathing difficulties. The patient also reports pain in both legs after involved in a minor traffic accident, which is the immediate cause of admission. Minor bruising is apparent on the front of the left leg. Along with other tests and monitoring, a pulse oximeter monitor of the present invention is utilized, with on CSS probe on the nares of the nose, and a PS probe on the large toe of each of both feet. Alarmingly, the CSS probe estimates that the arterial oxygen saturation at the CSS site is below about 85 percent, indicating hypoxia. The pulse oximeter monitor in both PS sites estimates even lower oxygen saturation, by about 5 percent, compared to the CSS site. There is no response to bronchodilator therapy, and the chest x-ray shows moderate fibrosis, and no attenuated vessels or hyperinflation. The initial diagnosis, aided by the pulse oximetry data, is bronchial COPD. Oxygen therapy is provided, and the pulse oximetry data is utilized to monitor increases in blood oxygen saturation both at the CSS and PS sites.

It is noted that the following paragraphs, through and including Example 5, describe embodiments of the present invention which combine, preferably integrally, a pulse oximeter probe with a nasal cannula through which is delivered a supply of oxygen or oxygen-rich air. In some of these embodiments, the combined pulse oximeter sensor/nasal cannula with oximeter is used to monitor and provide information regarding the oxygen saturation status, using data obtained from the sensor through the tissue of the nasal septum, to the user of the device, to caretakers of that user, and/or to a remote station that utilizes the information. For instance, the user can view current and/or historical trend data and manually adjust the flow rate of the oxygen or oxygen-rich air accordingly. Alternately, a user of said combined pulse oximeter sensor/nasal cannula with oximeter, in advance of a period of expected increased exertion, may increase the flow rate of his/her auxiliary oxygen supply. Then, during such exertion, such user refers to the oximeter data output and further adjusts the flow rate as needed to attain or remain within a desired range of blood oxygen saturation as indicated by the data output from the oximeter.

In other embodiments, the combined pulse oximeter sensor/nasal cannula is used in further combination with a central processing unit that sends signals to automatically adjust the flow rate of the oxygen or oxygen-rich air to the use. For instance, and not to be limiting, during more strenuous exertion, arterial blood oxygen saturation of a person needing oxygen supplementation therapy is expected to decline appreciably. In such circumstance, this drop in oxygen saturation is detected by the pulse oximeter probe, the trend data is analyzed by a program in the central processing unit, and a signal is sent to a valving mechanism that results in a greater oxygen flow directed through the user's cannula. A feedback loop, the data from the nasal pulse oximeter going to the central processing unit monitoring system, subsequently decreases the flow when the data indicates arterial blood oxygen saturation has exceeded a designated percentage. By such feedback loop approach, the oxygen delivered via the nasal cannula is better optimized for actual physical exertion and/or changing metabolic requirements.

In other embodiments, which are preferred in certain applications, the use of data from the nasal pulse oximeter to regulate oxygen flow to the nasal cannula is combined with other approaches to conserve oxygen, which include, but are not limited to:

1. detection of the inhalation phase of the respiration cycle to provide the oxygen (or oxygen-enriched gas) only during inhalation (or a key segment of the inhalation, i.e., the initial ⅔ of the inhalation);
2. providing oxygen every other breath; and
3. providing greater volume and/or flow rate at key part(s) of inhalation cycle (i.e., increased "shot size").

In yet other embodiments, which are preferred in certain applications, the data from the nasal pulse oximeter is combined with data collection of other parameters. For instance, in studying sleep disorders, a number of parameters are measured, for instance, pattern or dynamics of respiration (flow rate, inhale/exhale over time cycles), pulse rate, etc. In embodiments of the present invention, the use of the combined nasal pulse oximeter probe is combined with other monitoring sensors at the nose that detect, for instance, but not to be limiting, air flow and air pressure, such as during sleep, to analyze an individual's sleep disorder, such as sleep apnea.

Thus, when blood saturation information from the so-combined pulse oximeter probe is processed over time, and when trends are detected in the oximeter probe data processor that indicate a need for more or for less oxygen to the patient, based on, respectively, lower or higher blood oxygen saturation readings than a desired range, one or more outcomes result. As noted above, one outcome is to automatically adjust the supply of oxygen or oxygen-rich air to provide a needed increase (if readings were trending lower) or a decrease (if readings were trending higher, above a desired range, and conservation of the supply were desired) of that supply. Another outcome is to provide an alarm signal (audible, flashing, etc.) locally, for recognition by the patient or a nearby attendant. Yet another possible outcome is to provide a remote alarm, such as by cellular telephone transmission, to a physician's office, an ambulance service or hospital, etc.

Further, it is noted that there exist in presently used devices other approaches to conserving the supply of oxygen or oxygen-rich air. One commonly used approach, often referred to a the "pulse-dose" system, delivers oxygen to the patient by detecting the patient's inspiratory effort and providing gas flow during the initial portion of inspiration. This method is reported to reduce the amount of oxygen needed by 50 to 85% (compared to continuous flow) and significantly reduces the cost, the supplies needed, and the limitations on mobility caused by a limited oxygen supply.

For example, as the patient initiates a breath, the cannula tip senses the flow, a solenoid valve opens, and a burst of oxygen is rapidly delivered to the patient. The size of the burst or flow varies among different manufacturers. Commonly, the pulsed-dose system takes the place of a flow meter during oxygen therapy and is attached to a 50 PSIG gas source. In most devices the patient or operator can choose the gas flow rate and the mode of operation (either pulse or continuous flow). Typically, a battery-powered fluidic valve is attached to a gaseous or liquid oxygen supply to operate the system.

In addition, other approaches are used to further reduce oxygen usage when using the pulse-demand system. One such approach is to reduce the dose of oxygen delivered to the patient during each pulsation. Another approach, in combination or independently of the last one, is to deliver a burst only on the second or third breath instead of every breath. In addition, the size of the oxygen pulse dose will change with the flow setting with increases in flow delivering larger doses of oxygen and vice versa.

It is noted that potential problems encountered when using the pulse-demand system include: no oxygen flow from the device; and decreased oxygen saturations in the patient. If no oxygen flow is detected, then possible causes include a depletion of the gas supply, an obstruction or disconnection of the connecting tubing, or, critically for a pulse-demand system, an inability of the device to detect the patient's effort to breath. If the device cannot detect the patient's inspiratory effort, the sensitivity will need to be increased or the nasal cannula will need to be repositioned in the nares.

A decrease in the patient's oxygen saturation should always be a cause for alarm and may indicate a change in the patient's medical status, tachypnea, or a failure in the device. In any case, a backup system should be available in order to verify whether the problem is with the device or with the patient.

Thus, although in common use, the limitations of many pulse-dose systems are: relatively high cost of the system; technical problems may be associated with such a complicated device (including disconnections, improper placement of the device, and a possible device failure); lack of accommodation for an increased need during exercise, stress, illness, etc. and variable operation of the device if not properly set up.

Variations on the pulse-dose system include delivering oxygen to the patient at the leading edge of inspiration. This allows oxygen to be supplied exactly when needed. Thus, when the patient inhales, a relatively higher quantity of oxygen is delivered for travel deep into the lungs, increasing the probability of greater utilization and uptake in the red blood cells in the person's bloodstream. Other variations on the pulse-dose system are known in the art.

The present invention is used independently of the pulse-dose system, or, alternatively, in conjunction with such system, to conserve the supply of oxygen or oxygen-rich gas, and to better adjust the supply to the actual demands of the patient/user as that person's physical activities and demands vary over time. In particularly preferred embodiments, the pulse oximeter probe that is in combination with an outlet (e.g., the end of a cannula) of the supply of oxygen or oxygen-rich gas is fashioned to be integral with, or securely fastened to, that outlet. This provides greater surety of signals and proper insertion of the outlet. For instance, when the pulse oximeter probe is integral with the nasal cannula, if the probe and device are accidentally moved from their proper location (e.g., entrance of nose, or mouth), then the oximeter readings (including pulse) will deviate sharply from normal. In such instance an alarm can be quickly sounded and the problem rapidly corrected. Thus, this provides a distinct advantage in comparison to peripheral probes, such as finger or toe probes.

Another aspect of the present invention is adding as an additional sensor a capnography sensor (such as an infrared sensor) to estimate the concentration of carbon dioxide in the exhaled breath. This may be useful to detect more rapidly than pulse oximetry the failure of ventilation means (such as the wrong gas being provided to the patent), or carbon dioxide poisoning. Regarding the latter, the article entitled "Management of carbon monoxide poisoning using oxygen therapy" by T W L Mak, C W Kam, J P S Lai and C M C Tang, in Hong Kong Medicine Journal, Vol. 6, No. 1, March 2000 is instructive.

Also, as to the detection of a failure of ventilation means, when the present invention's combined nasal pulse oximeter sensor/cannula is attached to a pulse oximeter that is programmed to distinguish normal from abnormal pulse ranges, and when the combined nasal pulse oximeter sensor/cannula falls away from the user's nose (e.g., by accident during sleep or sedation, etc.), an alarm can be quickly provided based on the lack of pulse in the proper range. In this way the combined nasal pulse oximeter sensor/cannula more rapidly detects a loss of supplemental oxygen more rapidly than typical capnography detectors as to this reason for loss of ventilation.

Thus, the following examples are to be understood to be usable independently or in combination with the above described other approaches to conserving the supply of oxygen or oxygen-rich gas, and/or with other approaches known in the art but not described above, including those referred to in references cited herein.

EXAMPLE 5

FIG. 8 depicts one embodiment of a nasal oximeter probe, such as depicted in FIGS. 2A-D, in which the oximeter function and hardware are combined and integral with a cannula to supply oxygen (or oxygen-rich air or other gas mixture) to via the nostrils of the patient. The device, 150, shown in FIGS. 8A, B is but one specific embodiment of a range of designs and combinations that include a pulse oximeter probe in combination with an outlet for oxygen or oxygen-rich gas to a person in need thereof. For instance, while in the present example a cannula (defined as "a tube for insertion into body cavities and ducts, as for drainage") is used within the nasal oximeter probe to conduct oxygen-rich air or other gas mixture into the nostrils of a patient, any of a range of different conduits can serve this purpose. As one example, not meant to be limiting, a passage can be formed by molding such passages within the structure of the nasal oximeter. Such passages themselves can serve to conduct oxygen-rich air or other gas mixture into the nostrils of a patient. Alternately, these passages can be sized and configured to allow cannula tubing to be inserted through such passages, to provide for relatively easy assembly with standard cannula tubing which is common with standard regulators and tanks. Thus, the term "passage" is taken to mean any physical structure, now or later known to those of skill in the art, that provides for the physical containment of a gas that is being directed through such structure. Common forms of passages include cannula tubing, standard plastic tubing, and the continuous voids in a molded nasal pulse oximeter through which a gas may pass without loss from seams, etc. in the voids.

FIG. 8A is a front view, and FIG. 8B is a side view of the combined, or integral, nasal probe/cannula, 150. From a resilient plastic housing, here depicted as comprised of a main section, 152, protrude two extensions, 154 and 156, that are sized to enter the nares of the nose. Preferably, the lateral cross-sectional surface area of each of these extensions, 154 and 156, is not greater than 50 percent of the opening cross-section area of a nares at its widest opening, more preferably the device's inserted cross-sectional surface area is not greater than 35 percent of such opening area of a nares, and even more preferably, the device's inserted cross-sectional surface area is between about 20 and about 35 percent of such opening area of a nares. At the end of these extensions, 154 and 156, which preferably are of molded plastic and integral with the major portion, the plastic housing, 152, are inserted two circuit boards, 163, one containing two light-emitting diodes, 162 and 164 (shown here on extension 156) and the other containing a photodetector, 166 (shown here on extension 154).

As discussed for FIGS. 2A-G, in certain embodiments, the two extensions, 154 and 156, are spaced apart from one another so as to fit snugly against the tissue of each side of the septum to avoid interference from ambient lighting. Moreover, in certain embodiments as described above, the two extensions, 154 and 156 are constructed and spaced apart so as to fit non-contiguously with the mucosal cell lining of the interior septum walls.

Also, as discussed for FIGS. 2A-G, it is noted that clear plastic covers, 161, are placed over the molded plastic frame, 169, that forms the extensions 154 and 156 in FIGS. 8A-B. These plastic covers typically are heat-sealed over the LEDs 162 and 164 and photodetector 166. In various embodiments, the sides, 165, of the clear plastic covers, 161, that are facing or contacting the nasal septum (not shown) are aligned with the inside faces, 167, of the extensions 154 and 156, so as to fit, respectively, near or against the tissue of each side of the septum, without irritation, as from a rough or uneven surface. As noted in more detail elsewhere, the covers, 161, preferably have inner faces co-planar with the inner faces of the two extensions, 154 and 156. This is to ensure a comfortable fit, good data since ambient light is lessened, and no necrosis of the tissue being contacted. In all such embodiments, it is preferred that the two extensions, 154 and 156, deflect from the septum wall due to flexibility of the structures themselves, 154 and 156. This is particularly helpful when a patient has an interior septum wall wider than the spacing between the inner sides, 165 (so that there is substantial contacting), when a patient has septum wall irregularities (i.e., a deviated septum wall), or when a patient has a columella substantially wider than the inner faces, 167. Also, depending on relative sizing of nasal probe to a septum, embodiments as described herein are designed and sized to fit providing a space between the inner sides, 165, and the mucosal lining of the interior septum. Other embodiments are designed and sized to provide such space, and also to be separated from, or apply less pressure against, the columella.

Further as to the plastic covers, 161, one is fitted over each of the structures, 163, that contain the LEDs 162 and 164, located on extension 156, and the photodetector 166, located on extension 154. The plastic covers, 161, preferably do not interfere with light transmission. Apart from heat-shrink sealing, other means of attaching the plastic covers, 161, to the extensions 154 and 156, include, but are not limited to, sonic welding, spot gluing, hot gluing, press fitting, and other such methods of attachment, as are employed in the art, that are used to attach components of a medical device for entry into an orifice of a living subject. In general, the combined nasal pulse oximeter probe/cannula devices of the present invention are designed to be disposable, due to problems associated with cleaning between uses. However, it is within the scope of the invention that appropriate plastics, components and construction are employed so as to allow an appropriate level of sterilization of such devices between uses.

As for the nasal pulse oximeter probe depicted in FIGS. 2A-D, two extensions, 154 and 156, extend from a main section, 152, of a resilient housing, typically of plastic, that positions and spaces the extensions 154 and 156. These two extensions, 154 and 156, are sized to enter the nares of the nose in similar fashion to a nasal cannula oxygen supply. These extensions, 154 and 156, are flattened in one dimension, as depicted in FIGS. 8A and 8B, and are shown angled at about 15 degrees in a second dimension, as viewed in FIG. 8B. This angle of inflection, 170, is properly drawn from a line drawn from one edge of the main section, 152. 168The first approach described above for the nasal oximeter probe in FIGS. 2A-D is used to protect the components of the combined nasal pulse oximeter probe, 150, from moisture and contamination. A clear plastic covering, shown as 161 in FIGS. 8A, is placed over, to cover, each distal half of the two extensions, 154 and 156. It is noted that in the embodiment shown, the molded shell, 169, that forms and covers the main section, 152, also covers the approximately proximal half of the two extensions, 154 and 156. Either this, or a separate resilient insert, provides a support for the upper, or distal halves of these extensions, but does not cover the front and rear sides, nor the inner sides, 165, of these extensions. To cover these exposed sides, a clear plastic covering, 161, is constructed, fitted over, and adhered to the existing components to form an integral protective exterior surface with the molded outer shell, 169. Such plastic covering, 161, typically is manufactured by heat sealing pre-cut and/or pre-formed pieces to form a fitted covering over the distal halves of extensions 154 and 156. Then this is shrink-wrapped over the components of the distal half of the two extensions, 154 and 156. The plastic covers, 161, preferably do not interfere with light transmission in the critical wavelength ranges of the LEDs 162 and 164. Apart from heat-shrink sealing, other means of attaching the plastic covers, 161, to the extensions 154 and 156, include, but are not limited to, sonic welding, spot gluing, hot gluing, press fitting, and other such methods of attachment, as are employed in the art, that are used to attach components of a medical device for entry into an orifice of a living subject. Also, other means of providing a protective covering, such as are known to those skilled in the art, may be used instead of the above-described approach.

Further, using the shrink-wrapping construction described above to cover the distal halves of the extensions 154 and 156, and dimensioning the spacing between the extensions 154 and 156 as indicated above for a non-contiguous fit, the extensions 154 and 156 are found to fit without irritation to the mucosal cells lining each side of the interior septum, as from a rough or uneven surface. For example, without being limiting, when using heat sealing plastic as the covering, 161, the thickness of this material, and any finish on the adjoining edge, will affect the extent of a sensible ridge at the junction of the covering, 161, and the molded outer shell, 169, but nonetheless provide a comfortable fit.

The nasal septum extends in the midline from the tip of the nose anteriorly to the posterior border of the hard palate posteriorly. It is bordered inferiorly by the roof of the mouth (the hard palate) and superiorly by the floor of the cranium. As to a specific area of the nasal septum that is preferred for use of a nasal pulse oximeter probe such as the one depicted in FIGS. 8A,B, at least one highly vascularized, and thus more suitable, area of the nasal septum is located approximately 0.5-1.0 cm. from the posterior border of the nostril and approximately 2.0-2.5 cm. superior to the floor of the nasal cavity in the midline. Being more highly vascularized, such thereby provides more consistent and reliable signals than less vascularized areas that are, relative to this, more proximal (the tip of the nose) or more distal (further posterior towards the back of the nasal cavity). In particular, and more specifically, the highly vascularized area of the septum, known alternately as Kiesselbach's plexus and Little's area, is a preferred target area for detection of blood oxygen saturation levels by a nasal pulse oximeter probe of the present invention.

The pulse oximeter nasal probe of the present invention is designed so that, when properly positioned, it passes its light through such highly vascularized areas. In the particular device shown in FIGS. 8A,B, an angle of inflection, 170, is shown between plastic housing, 152, and the two extensions, 154 and 156. This angle properly is measured as an interior deviation from a straight line extended from the plastic housing, 152. In preferred embodiments, the angle of inflection, 170, is between about 0 and about 33 degrees, in more preferred embodiments, the angle of inflection, 170, is between about 10 and about 27 degrees, and in even more preferred embodiments, the angle of inflection, 170, is between about 10 and about 20 degrees. In FIG. 8B, the angle of inflection, 170, is about 15 degrees. This angle has been found to provide superior results in testing.

Further, it is noted that in typical use contact by an inner face of one extension with nasal mucosal tissue interior to the columella precludes contact by the inner face of the other extension with the nasal mucosal tissue interior to the columella. Further, in many if not most instances, where there is a snug fit against the columella, there is little or no contact by the more distal, inward sections of the respective extensions against the nasal mucosal tissue interior to the columella. Where a patient has a substantially deviated septum, there may be contact by one extension on one side, but this is believed, in most cases, to preclude contact by the other side once interior of any contact with the columella.

Thus, for the embodiments depicted in FIGS. 2 and 8, a most common fit with a nasal septum, when the respective device is in use, is that certain areas of the inner faces of the extensions only occasionally or lightly contact a portion of the tissue of the interior septum wall. Such portion is typically a protruding portion. It has been learned that this orientation, where the extensions bearing the light-generating and the light-detecting structures, does not and need not press against both sides of the nasal septum. Surprisingly, relative to prior art teachings, pressing against the tissue of the septum wall is not needed in order to obtain good pulse oximetry data.

As noted above, in certain embodiments contact with the nasal interior septum mucosal tissue is avoided or minimized by one or more of: sizing of the probe (particularly spacing between opposing inner faces), flexibility of the material used, other design features, and lack of design and/or structure to compress or clip any part of the probe to the tissue of the nasal septum. Thus, in various more preferred embodiments, the inner sides (i.e., 65 or 165), of the two extensions, (i.e., 54 and 56 or 154 and 156), if they ever contact the tissue (mucosal nasal lining) of the interior septum, do so lightly, resting without excessive pressure, so as to avoid the development of necrosis of the mucosal tissue. This applies even when the nasal probe is used over extended periods of time. Also, it is noted that a snugly fitting probe, as described in certain embodiments and within its broader context, comprises probes that contact comfortably the columella, whilst remaining spaced from (i.e., facing, adjacent to), the tissue of the nasal interior septum.

Further, referring to FIG. 8A, in general, the two extensions, 154 and 156, are angled so that upon insertion and proper placement into position in the nostrils, the LEDs 162 and 164, located on extension 156, emit light directed through a region that includes a preferred area of the nasal septum. Most preferably, the LEDs 162 and 164, located on extension 156, direct light exclusively through the highly vascularized region of the septum known alternately as Kiesselbach's plexus and Little's area (or, in The Principles and Practice of Rhinology, Joseph L. Goldman, Ed., John Wiley & Sons, New York, 1987, Kiesselbach's plexus is "in" Little's area). Empirically, in certain evaluations, this highly vascularized region, referred to herein as Kiesselbach's plexus, is measured to be located approximately 2.0 cm upward and approximately 1.0 cm inward (toward the back of the head) from the tip of the anterior nasal spine. Kiesselbach's plexus is the region of the nasal septum where the terminal branches of at least two arteries meet and supply the tissue. These major terminal branches in Kiesselbach's plexus are those of the nasal septal branch of the superior labial branch of the facial artery and the anterior septal branch of the anterior ethmoidal artery (see, for example, plate 39 of Atlas of Human Anatomy, $2^{nd}$ Ed., Frank H. Netter, M.D., Novartis, 1997). Some terminal branches of the posterior septal branch of the sphenopalatine artery may also be found in more posterior regions of Kiesselbach's plexus.

Also, because Kiesselbach's plexus actually is comprised of a region of highly vascularized tissue, rather than a discrete point, and given anatomical variation among persons, a range of approximately +/−0.25 cm from the above indicated measured point also is acceptable as a target area to obtain unexpected superior results with a nasal pulse oximeter probe. It also is recognized, based on the approximate size of the Kiesselbach's plexus, that placing the probe so it measures saturation within a range as large as approximately +/−0.75 cm from the measured point may also provide these unexpected superior results (by having the light pass through this highly vascularized region). However, given the variations noted above, this is less preferred than the range of approximately +/−0.25 cm. from the measured point. Under certain circumstances, a range of approximately +/−0.50 cm. from the measured point is considered acceptable. Given the basic morphology and sizing of the nares, design and placement of nasal pulse oximeter probes such that they pass light through nasal septum tissue within these larger ranges, but not within the smaller approximately +/−0.25 cm. range, frequently requires probes of the present invention that are designed to have smaller (i.e., thinner, narrower) profiles than the profile depicted in FIGS. 8A and 8B. This allows these probes to come closer to the outward or inward structures of the nares and maintain patient comfort.

Figure 11:
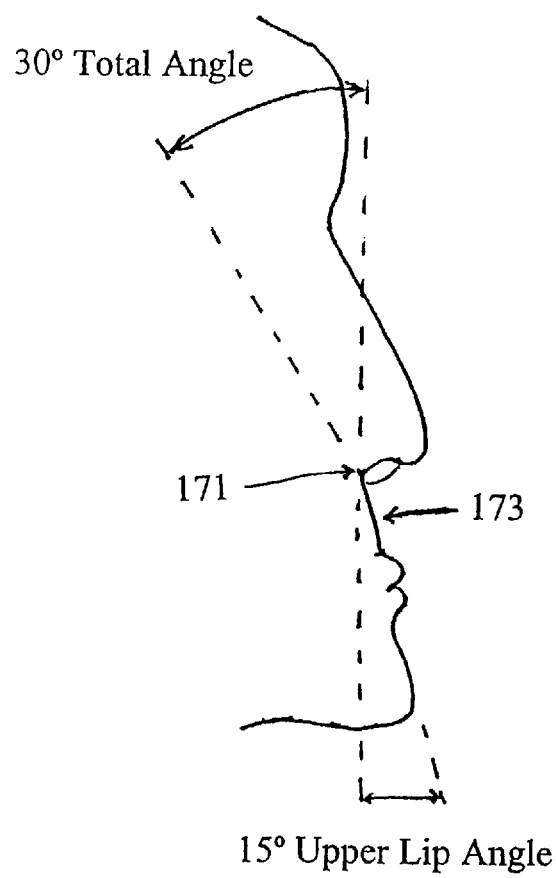
FIG. 11 provides a diagrammatic profile of a human subject indicating the angle of the upper lip, and how this affects the positioning of a nasal probe of the present invention.
Figure 12A:
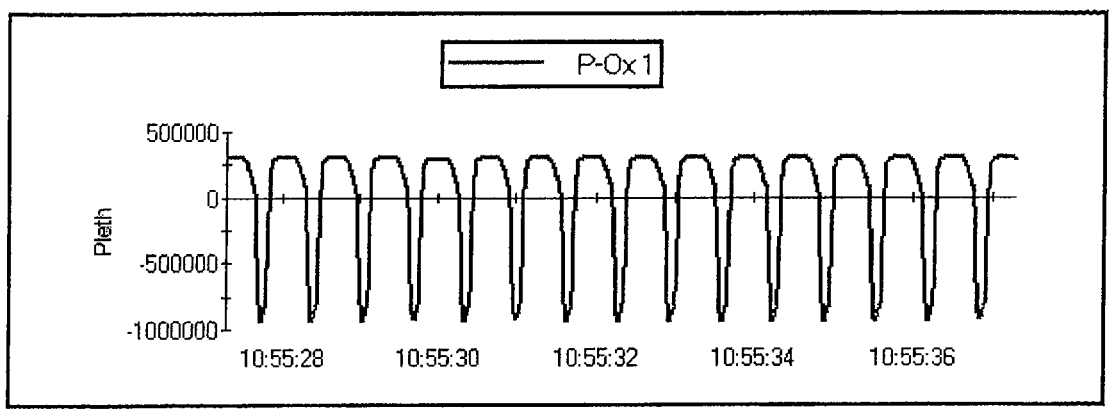
FIGS. 12A-15B display data from a comparison of positions on the nasal interior septum of one volunteer subject, indicating the difference in signal strength and quality when the nasal probe is positioned to obtain data through a vascularized plexus identified as Kiesselbach's plexus.
Figure 12B:
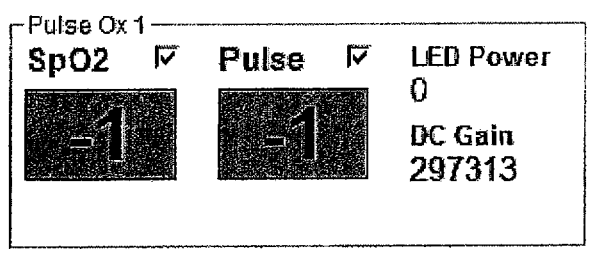
Figure 13A:
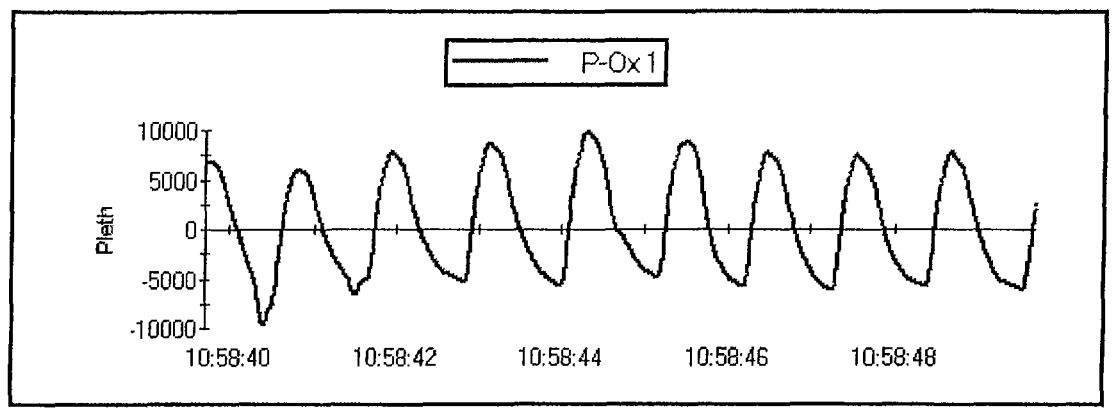
Figure 13B:
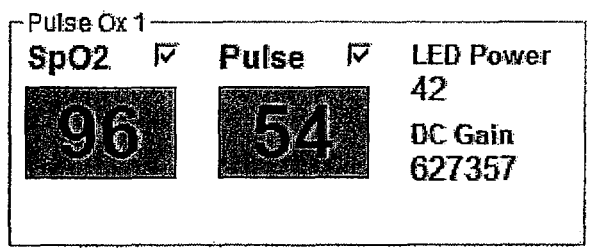
Figure 14A:
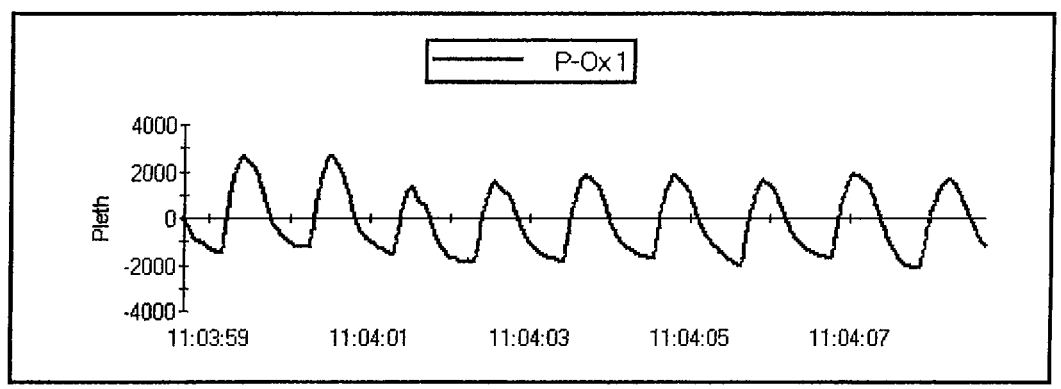
Figure 14B:
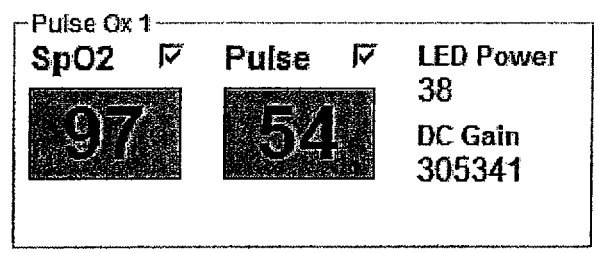
Figure 15A:
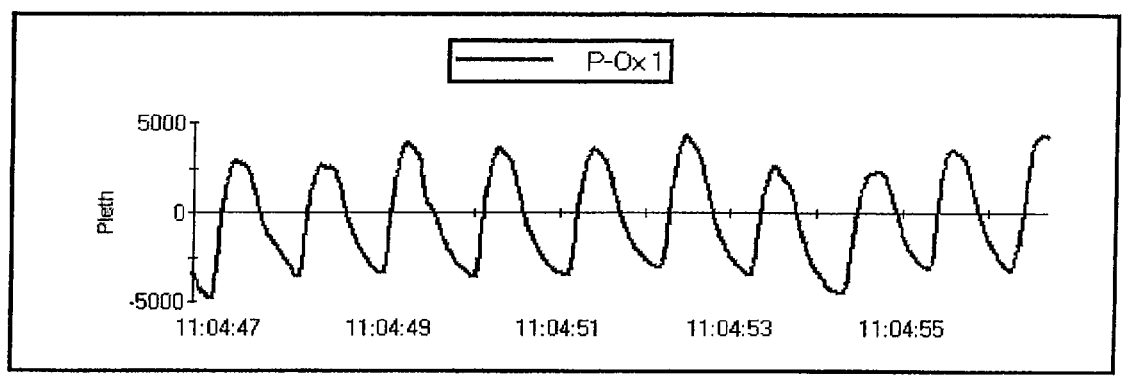
Figure 15B:
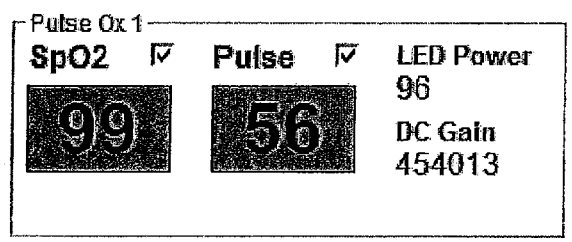

Also, for any of these ranges to target Kiesselbach's plexus, it is appreciated that the angle of a particular individual's lip in relation to the nose, and the placement of the nasal probe sensor on the upper lip, affect the exact location of the probe's light producing and light sensing components on the plexus. As noted, it has been learned that a nasal pulse oximeter, such as is depicted by 150 (with or without the oxygen cannula element), that has an angle of inflection, 170, of about 15 degrees, has been found to provide superior results in testing. This 15 degree angle to reach Kiesselbach's plexus with the light-generating and the light-detecting components, in order to obtain superior sensing data, takes into account that for many patients, there is an angle of the upper lip, tilting about 15 degrees. This is represented in FIG. 11, a facial profile. FIG. 11 also shows an angle, from a true vertical, starting from the opening of the nostril at the medial end, 171, of about 30 degrees that generally leads toward the desired area for obtaining pulse oximeter data, Kiesselbach's plexus. This 30 degree angle includes the benefit of the approximately 15 degree angle of the upper lip, 173, upon which the nasal probe of the present invention is placed. Thus, with this angle of the upper lip, in combination with a 15 degree angle of the nasal probe, the light generating and light detecting components of the nasal probe are positioned at the desired vascularized area, generally located along the 30 degree angle inward and upward from the opening of the nostril at the medial end, 171. One example of a nasal probe with a 15 degree angle, or bend, is shown in FIG. 8B. It is noted, however, that a nasal probe with such angle may be with or without a cannula.

However, it is appreciated that the shape and angle of person's upper lip, and orientation to the nasal cavity, do vary. Thus, in certain embodiments, it is desirable to adjust the exact angle of the nasal probe in relation to the upper lip (such as by gently twisting it as it is being secured to the upper lip) to obtain the most preferred area for data. Also, optionally, the pulse oximeter is comprised of circuitry and data output that provides a "perfusion index" to assist in improved placement of the probe so that the light-generating and light-detecting components are placed in or near to the desired Kiesselbach's plexus. As known in the art, the perfusion index is the ratio between the pulsatile and the non-pulsatile components of the light that reaches the light-detecting component. This provides a means to find which position has a greater pulsatile component, and can assist, when needed, in orienting a nasal probe to obtain a superior or the preferred site. It is noted, however, that in trials, the probe having a bend of 15 degrees, as shown in FIG. 8B, has been found to provide reliable data for 30 patients tested to date without a need for subtle or time-consuming adjustment of position on the upper lip.

Also shown in FIG. 8B is a conduit for oxygen (or oxygen-rich air or other gas mixture), 180, and a conduit, 182, within which are electrically conductive wires (or other types of signal transmission means, such as fiberoptic cable) to pass electrical signals to and from the two light-emitting diodes, 162 and 164, and the opposing photodetector, 166. 180Means of stabilizing the probe, 150, such as elastic straps (not shown) from any part of the device that span the head of the patient, typically are employed, and depend on the type of application and the comfort requirements of the user. More particularly, in order to stabilize the desired position of the nasal probe of the present invention (whether it is with or without a cannula), several specific approaches are useful. One approach to reversible attachment of the nasal probe to the patient is to apply tape to all or part of the patient's upper lip, where the side of the tape to the patient's upper lip has an adhesive suited for the purpose and desired contact period, and the other, exposed side has one or more sections of either the hook or the loop of hook-and-loop type fabric. The side of the nasal probe to rest on the upper lip ("back side") is comprised of one or more sections of the hook-and-loop type fabric to complement the sections on the tape's exposed side, and by virtue of alignment and pressing together of the sections on the nasal probe and the upper lip, the nasal probe is positioned on the upper lip. This type of reversible attachment can be modified as needed, particularly when the strength of the adhesion of the hook-and-loop type fabric is lessened just to the strength needed to maintain the probe in position in view of the typical range of forces acting to dislodge it. A variation is to apply tape to the back side of the nasal probe, where the tape has adhesive on the side toward the probe, and hook-and-loop type fabric on the opposite side, facing and attachable to the hook-and-loop type fabric on the tape of the upper lip.

Another approach to reversible attachment of the nasal probe to the patient is to apply double-sided adhesive tape to all or part of the patient's upper lip. Then the back side of the nasal probe is pressed against the adhesive on the upward-facing side of the double-side adhesive tape. A variation is to apply the double-sided adhesive tape first to the back side of the nasal probe, then orient the probe into its position against the upper lip with the extensions in the nares, and then press against the upper lip to obtain adhesion thereto. When using such approaches, it is advantageous to have a stabilizer (such as 58, in FIG. 1, there shown simply as a flat plate flush with and extending downward from the inside edge of the lower plane of the extensions 54). This provides additional surface area for contact with the tape, and improves the stability of the reversible bonding with the upper lip, and thereby helps maintain a proper orientation to the desired vascularized areas for detection of the condition of the arterial blood and its flow.

Yet another approach to reversible attachment of the nasal probe to the patient is to apply single-sided adhesive tape over the top of the nasal probe. This is done before or after the nasal probe has been positioned with the extensions in the nares and the back side against the upper lip, and the tape is pressed into the skin of the face adjoining the nasal probe, to secure the probe in place.

As for the probes depicted in FIGS. 1 and 2A-D and described above, timed electrical impulses from a pulse oximeter monitor system pass through two wires or other signal transmission means (not shown) in cables held within conduit passing within 182 to produce the light from LEDs 162 and 164. At least one photodetector, 166, is positioned within extension 154 to face and oppose LEDs 162 and 164 on extension 156. The photodetector 166, which typically is a light-sensing photodiode, detects changes in the light emitted by the LEDs 162 and 164 as that light is differentially absorbed between and during pulses across the capillaries of the septum tissue between the two extensions, 156 and 154. In one embodiment, LED 162 emits light around 650-670 nm, and LED 164 emits light around 880-940 nm. The electrical impulses are timed to be offset from one another, so that the light from each of the two LEDs, 162 and 164, is emitted at different times. The photodetector, 166, detects the light passing through the septum of the nose, which is situated between extensions 156 and 154 when the probe 150 is in use. As discussed above, loss of signal through vascularized tissue such as the nasal septum is due both to background tissue absorption and the absorption by the blood in the arteries, which expands during a pulse. The signals from photodetector 166 pass through conductors (not shown) to the processor of the monitor system (not shown). As examples, not meant to be limiting, a single cable passing from one side of the device, 150, or two cables that may form a loop that may lie above the ears of the patient, or join to form a single cable (not shown), pass signals to the two LEDs, 162 and 164, and from the photodetector 166. In one preferred embodiment, a single cable, formed from the joining of two cables leading from the device, 150, terminates in an electrical plug suited for insertion into a matching socket in the pulse oximeter monitor system (not shown). In another preferred embodiment, the single cable terminates by connecting to an adapter cable, which in turn connects to a socket in the pulse oximeter monitor system (not shown). In a typical application, the signals from the light-sensing photodetector, 166, are ultimately received and processed by a general purpose computer or special purpose computer of the monitor system (not shown).

Per the disclosure preceding this example, this combination nasal pulse oximeter is used either in combination with the needed computer processing to interpret and provide a viewable (or audible in the case of an alarm) data output of arterial blood oxygen saturation for the user or health care worker, or, in alternative embodiments, this function is further combined with the means to regulate and adjust the flow of oxygen or oxygen-rich gas that is being delivered by adjustment of a valve controlling such flow.

EXAMPLE 6

Figure 10:
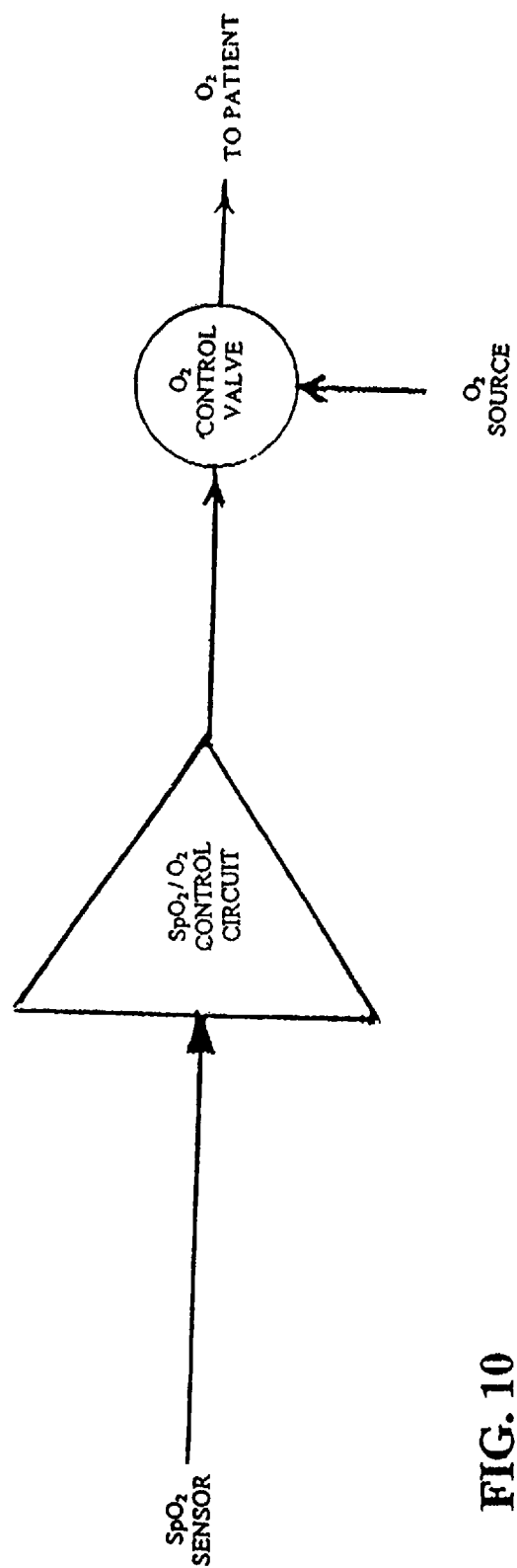
FIG. 10 provides a schematic flow diagram for control signal transmission from a pulse oximeter sensor to a control circuit to an oxygen control valve being controlled by data output from the sensor, where the control valve regulates oxygen to a patient wearing the sensor.

The present invention also is adapted for embodiments which utilize, in combination, pulse oximeter detection of arterial blood oxygen saturation, in combination with a supply of oxygen, air, or a gas mixture providing a variably supply of oxygen, where the flow rate and/or amount of oxygen provided in the gas mixture is controlled based at least in part by the changes and levels of arterial blood oxygen saturation, as detected by the pulse oximeter. Applications for such combination devices (pulse oximeter/oxygen supply directed by controller with pulse oximeter data as an input) include, but are not limited to: self-contained breathing apparatuses (SCBA); self-contained underwater breathing apparatuses (SCUBA); high altitude breathing systems, and medical gas delivery systems. The following figures and related disclosure provides only one, non-limiting embodiment to present the basic concepts of the present invention as applied to a SCUBA regulator. FIG. 10 is used to depict a general control approach for this and other systems described in this application.

FIG. 9A presents a diagram of a basic SCUBA regulator, 200, with key features described. The housing, 220, contains a diaphragm that senses ambient water pressure which is linked physically to adjust the delivery pressure to the user via regulation of the second stage regulator, also within the housing, 220. A supply hose, 212, carries compressed air, or other gas mixtures, typically from a supply tank (not shown), to the second stage regulator (not shown) within the housing, 220. Upon demand from the user, whose mouth is fitted around the rubber mouthpiece, 201, the air or other gas from the hose, 212, passes through the second stage regulator, and through the mouthpiece, 201, to provide the user with a supply of air or other gas based on the flow pattern of the second stage regulator. Having the rate of this flow upon demand being variable, based in part on the type of regulator and its operating conditions and maintenance, can result in waste of precious air supply. Also, when the percent of oxygen or other gas in the air supply can be altered based on data from a pulse oximeter, the body's physiological requirements can be better met, resulting in a safer and healthier dive experience.

FIG. 9B presents a diagram of the basic SCUBA regulator FIG. 9A, however also comprising additional features of the present invention. In particular, a flexible arm 202 bearing two light-emitting sources, 204 and 206, (typically LED's) is disposed in a place exterior to the position of the lip of the diver using the regulator. The approximate thickness of the lip is represented in FIG. 9B by the distance, a. Flexibility of the arm 202, is by the nature of the material such as rubber and/or by spring loading. By such design, the arm 202 moves easily away during fitting of the mouthpiece (i.e., the placement of the lip around the flange, 207, of the mouthpiece, and the teeth over the nubs, 209 (one is shown as a dashed rectangle to indicate position on the inside surface of the flange). Then the arm, 202, presses against the lip or against the skin just below the lower lip, in such an orientation so that light emitted by the two light-emitting sources, 204 and 206, is directed toward a photosensor, 208, inset into the outer surface of the rubber mouthpiece 201. This receives signals through the lower lip/flesh below the lip, which is sufficiently well-vascularized to provide a representative reading of the body's oxygen status expressed as of arterial blood oxygen saturation. Wiring 210 passes data signals between this pulse oximeter probe and the oximeter controller (not shown, end of wiring in figure coincides with end of supply hose, 212). This interprets the data signals from the pulse oximeter probe and, based on the information received, directs a separate valve (not shown) to adjust upward or downward the level and/or pressure of oxygen supplied through the supply hose 212 to increase or decrease the absolute or relative oxygen flowing to the regulator at the mouthpiece shown in FIG. 9B.

For SCUBA systems using HE/Ox mixtures, additional oxygen can be provided when indicated by the data from the oximeter, and/or by a manual control (such as the diver pressing a button to increase, with a second button to decrease oxygen flow incrementally). The same approaches apply to more complex dive gas mixtures, such as Triox (oxygen enriched air with helium) and Trimix (hypoxic oxygen, helium and nitrogen). By appropriate control mechanisms and algorithms (adjusted to compensate for physiological differences at different depths), a diver using such embodiments of the present invention extends the dive time on a particular quantity of oxygen, and/or has more oxygen when more oxygen is needed, and less oxygen when less oxygen is sufficient. This results in a safer, healthier dive experience.

The above disclosed improvements in the monitoring of blood oxygen saturation and adjustment of gases supplied to a SCUBA diver also apply to users of self-contained breathing apparatuses (SCBA) that are not used for underwater diving. For example, firemen and other emergency workers use SCBA in environments in which they may exert considerable energy and have transient very high oxygen demands. The above-disclosed embodiments, and variations of these known to those of skill in the relevant arts, provide benefits to such users.

FIG. 10 provides a flow diagram of the general information and control generation of the "pulse flow oxygen sensor" that controls the level or pressure of oxygen provided to a user wearing a nasal or mouth pulse oximeter sensor of the present invention in combination with the gas supply controlled by a controller receiving data input from that pulse oximeter sensor. Fundamentally, data signals from the pulse oximeter sensor go to an arterial blood oxygen saturation/oxygen supply Control Circuit. Based on analysis of these data signals using an appropriate algorithm, the arterial blood oxygen saturation/oxygen supply Control Circuit sends signals to a servodevice that adjusts an Oxygen Control Valve which receives oxygen under pressure from an oxygen source. From the $O_2$ Control Valve, oxygen is directed to a patient in need of oxygen, where that patient is wearing the combined nasal or mouth pulse oximeter sensor of the present invention in combination with the gas supply cannula or mouthpiece.

EXAMPLE 7

As described above, Kiesselbach's Plexus is a vascularized area in the anteroinferior part of the interior nasal septum, and is supplied by sphenopalatine, greater palatine, superior labia and anterior ethmoid arteries. These vessels originate from both the internal and external carotids and are the most frequent cause of epistaxis (nose bleed).

To demonstrate the utility of Kiesselbach's Plexus as a site for pulse oximetry, data was recorded from a more vascularized region of the nasal septum (i.e., Kiesselbach's plexus) using a probe of the present invention in its intended positioning. This data was compared to data from two adjacent sampling sites, one inferior and posterior, and one anterior and superior to Kiesselbach's plexus. Since all three sampling sites are capable of giving a signal for pulse oximetry with a standard pulse oximeter monitor, relative LED power provided a marker of utility. A lower LED power required to obtain a measurement indicates a stronger source signal. Such lower power requirement is apparent when the probe is placed so as to transmit light through the vascularized area identified as Kiesselbach's plexus. Also, as further discussed herein, a stronger signal source in the nasal or cheek/lip areas generally provide improved signals for use in plethysmography.

Figure 18A:
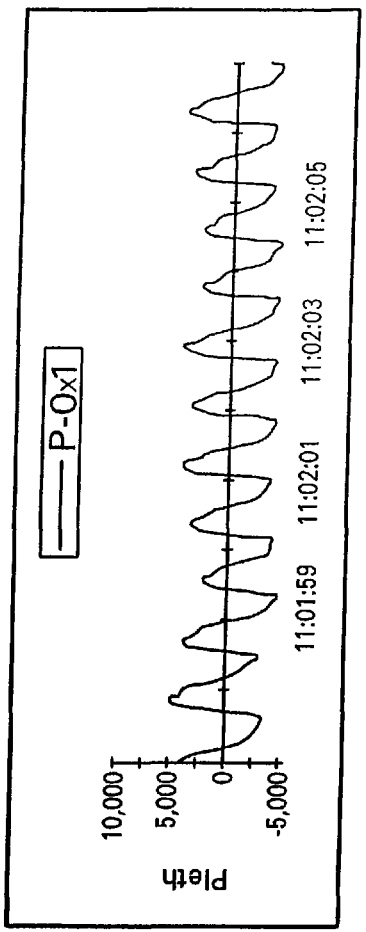
FIG. 18A-C displays data from a nasal probe on one volunteer subject, where the position of the probe was adjusted to three different positions.
Figure 18B:
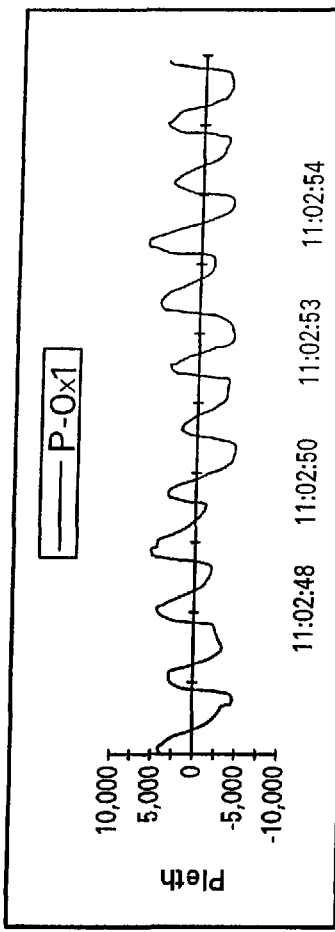
Figure 18C:
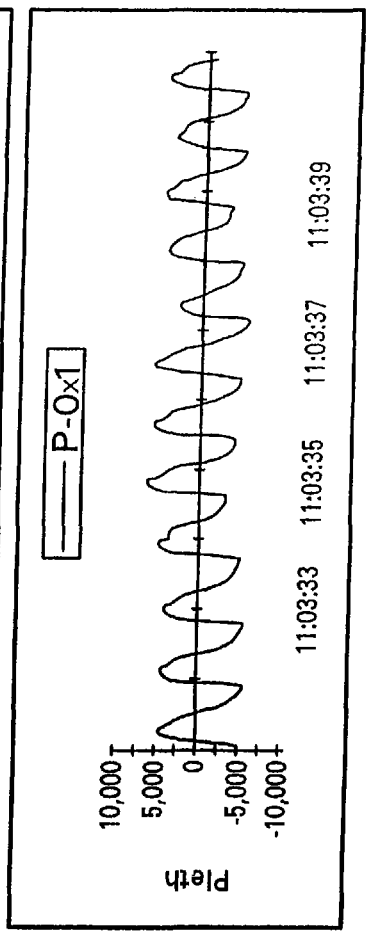

A nasal probe of the present invention, having a 15 degree inward angle, or inflection along its extensions, was utilized for the comparison. This probe has a side view similar to the probe in FIG. 8B. To obtain what is identified in FIG. 18A as "Approx. 0 Degrees," the probe was angled outward from its normal, desired position to approximate a position for the light-generating and the light detecting components over the nasal septum that simulates a probe having straight extensions (i.e., not having the 15 degree inward inflection). FIG. 18B, identified as "Approx. 15 Degrees," is the probe in its normal, desired position (see FIG. 11 and related discussion), with the 15 degree inflection positioning the light-generating and the light detecting components over the nasal septum at a desired position that, in subjects tested to date, provides superior results. To obtain what is identified in FIG. 18C as "Approx. 30 Degrees," the probe was angled inward from its normal, desired position to approximate a position for the light-generating and the light detecting components over the nasal septum that simulates a probe having such components further inward (anterior and superior) than the position obtained with the 15 degree-inflected probe seated on the upper lip. That is, based on the upper lip angle of 15 degrees, the probe position for the data shown in FIG. 18C is approximately 45 degrees inward of vertical (see FIG. 11 and related discussion).

Figure 18D:
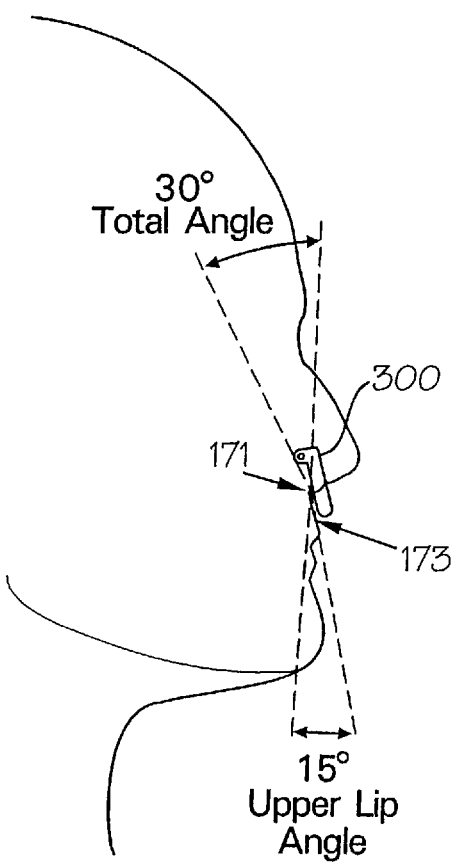
FIG. 18D depicts a side view sketch of a profile of a subject with an alternative nasal probe design that reaches to a desired location for obtaining data.

The data indicates that the probe in its intended position, with the back of the probe's main section against the upper lip, provides superior data. This is indicated by virtue of FIG. 18B's LED Power reading of 66, compared to the LED Power readings of 108 and 102 for FIGS. 18A and 18C, respectively. Without being bound to a particular theory, when the probe is in its intended position, it passes light through the more vascularized section of the nasal septum (i.e., Kiesselbach's plexus), and the standard algorithm of the pulse monitor obtains the desired data signals with a lower power to the LEDs. The data provided in this example is consistent with earlier testing which demonstrated, unexpectedly and advantageously, that superior pulse oximetry and plethysmography data is obtained when the distal end of the pulse oximeter probe extensions are designed so as to locate the light-generating and the light detecting components to a desired more vascularized locus, i.e., Kiesselbach's plexus. Thus, it is further appreciated that various designs that have the end result of locating the light-generating and the light detecting components to the desired more vascularized loci as obtained by the probes of the present invention, such designs are within the scope of the present invention. For example, and without being limiting, FIG. 18D provides an alternative design of an acutely angled nasal probe, 300, that achieves the same positioning as a probe having a profile of the probe in FIG. 8B.

Further, it is noted that in some subjects, a nasal probe of the present invention, when placed in the position as indicated above for FIG. 18B, provides data that, effectively, goes "off the scale." Without being bound to a particular theory, this is believed to be due to peculiarities of the algorithms used in the processor of a standard pulse oximeter, and/or the fundamental system logic of a finger pulse oximetry system. For example, the algorithm and processor of a standard finger pulse oximeter system are designed to adjust light intensity for a probe positioned on a finger, where there is a relatively higher percentage of less vascularized tissue compared to the nose, lip and cheek. In such circumstances, if a greater than expected amount of light is received at the photodetector, this may indicate the probe has slipped from the finger, or from the proper position on the finger. For such algorithm, a strong signal may be considered erroneous.

To address problems of "off scale" readouts for nasal probe data collected from some subjects, it has been further learned that various types of "filters" can be implemented to eliminate this problem. Two general approaches to "filtering" are electrical and light approaches. An example of the electrical approach is to place a resistor in series to both of the light producing LEDs. This proportionally decreases the amount of light emitted at both wavelengths. As to the light approach, a filter, such as a white material, a translucent or an opaque cover, can be physically placed over all or part of the light-producing LEDs, over the photodetector, or both, to reduce the light input into the photodetector, such that a readable signal can be generated in such subjects. This reduces the amount of both wavelengths of light received at the photodetector without dramatically altering the ratios of such wavelengths. Without being limited, yet another way to compensate for the more vascularized, higher light output areas of the nose, lip and cheek is simply to use smaller light-detecting photodiodes. If the response curve for the smaller photodiode remains the same compared to its larger counterpart, just it active area reduced, this would keep the light level ratios of the respective wavelengths proportional. For instance, a 0.4 mm size active area may be used instead of a 0.8 mm size active area. Other methods as known to those of ordinary skill in the art can likewise be employed to deal with the higher signal, particularly for probes that are used in pulse monitor equipment with algorithms designed for signals from finger probes. By adjusting the amount of light by any of the above means, and upon consequent adjustment of the output parameters of the oximeter, as many occur in certain units, the sensor output achieves a more acceptable range for monitoring.

In conclusion, the area of Kiesselbach's plexus across the nasal septum is the area in the nose of strongest signal for pulse oximetry as demonstrated by this simple experiment. It is noted that even using a filtered probe and placing it anteriorly of Kiesselbach's plexus a power level 2.5 times lower than what is required by the finger provides a good signal. As discussed above, one approach to locating this desired site is to use the probes having the desired bend, or angle of inflection. Another approach, which may only be needed in a small number of instances, is to use the perfusion index feature on a pulse oximeter device, and position where the index is highest.

EXAMPLE 8

Several specific profiles of data are provided from patients who underwent various procedures in a teaching hospital and who wore the pulse oximeter probes of the present invention. This data is illustrative of the value of the nasal probes of the present invention. For all figures below, the data designated as "PULSE OX 1" or "P-OX 1" is from a nasal probe measuring data across the interior nasal septum, the data designated as "PULSE OX 2" or "P-OX 2" is from a cheek/lip probe measuring data across the cheek (below the lip), and the data designated as "PULSE OX 3" or "P-OX 3" is from a conventional finger probe.

Figure 16A:
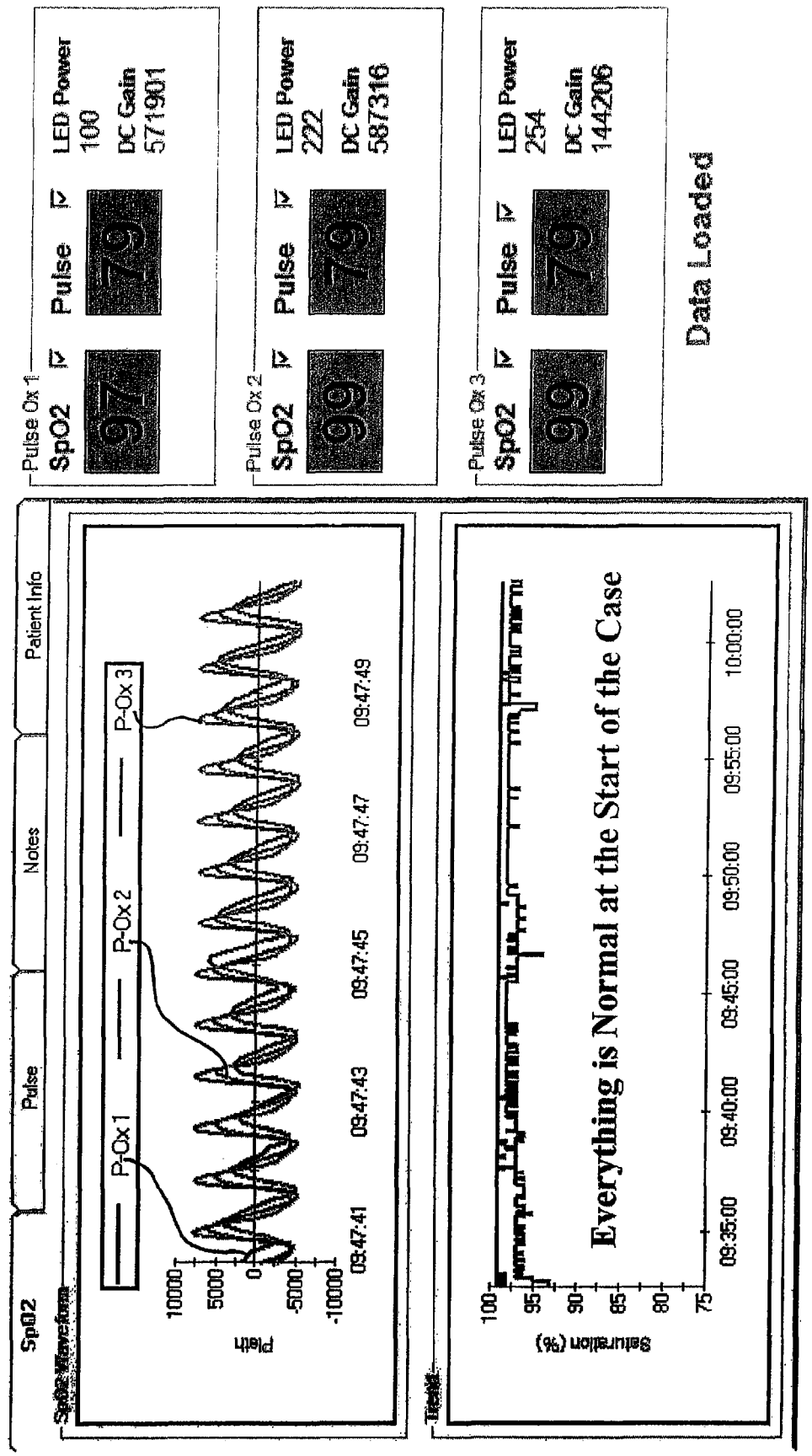
FIGS. 16A-C display data from a volunteer subject in which three pulse oximeter probes were evaluated and compared—one at the nasal interior septum, one at the cheek/lip, and one at the finger.
Figure 16B:
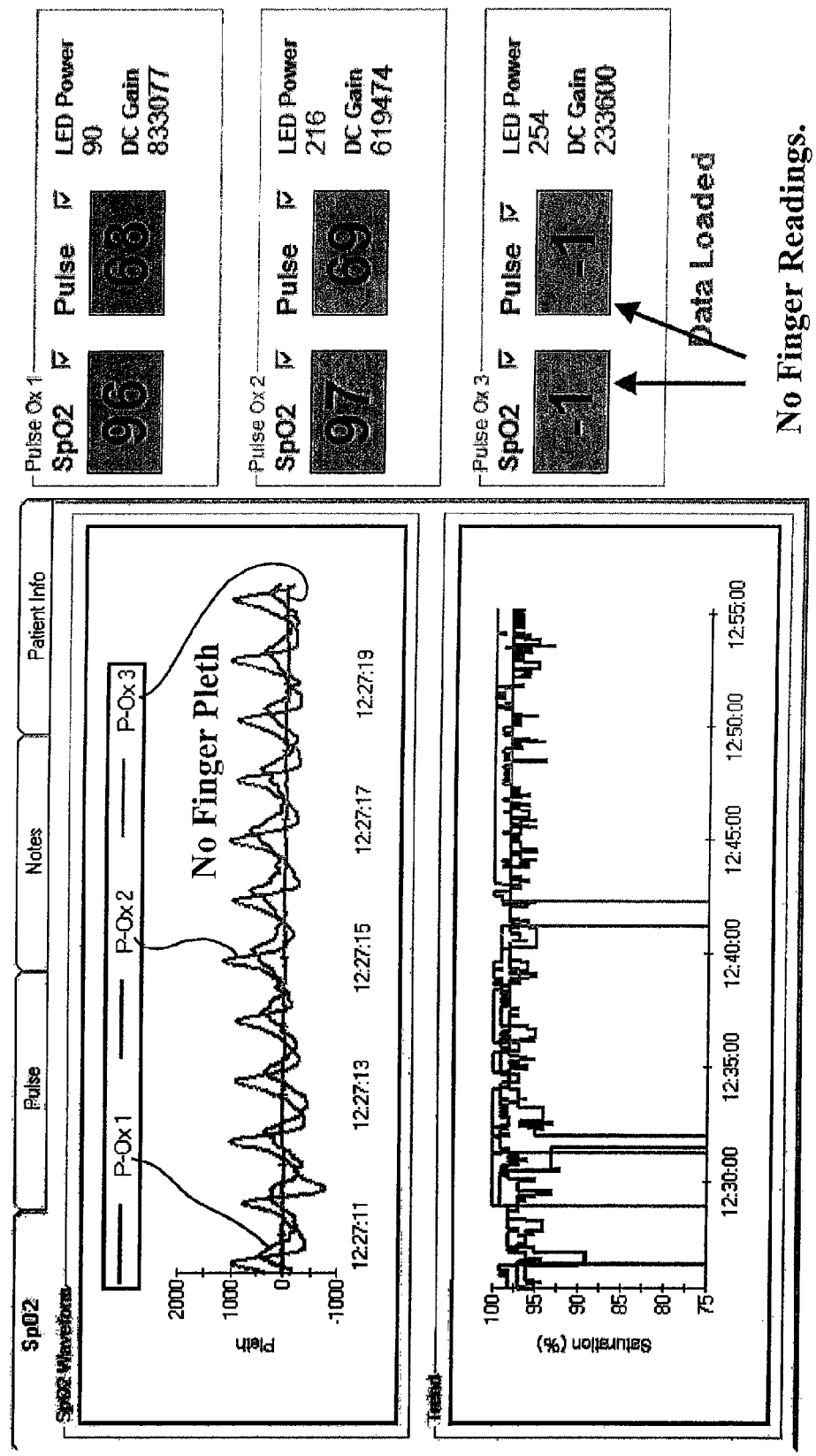
Figure 16C:
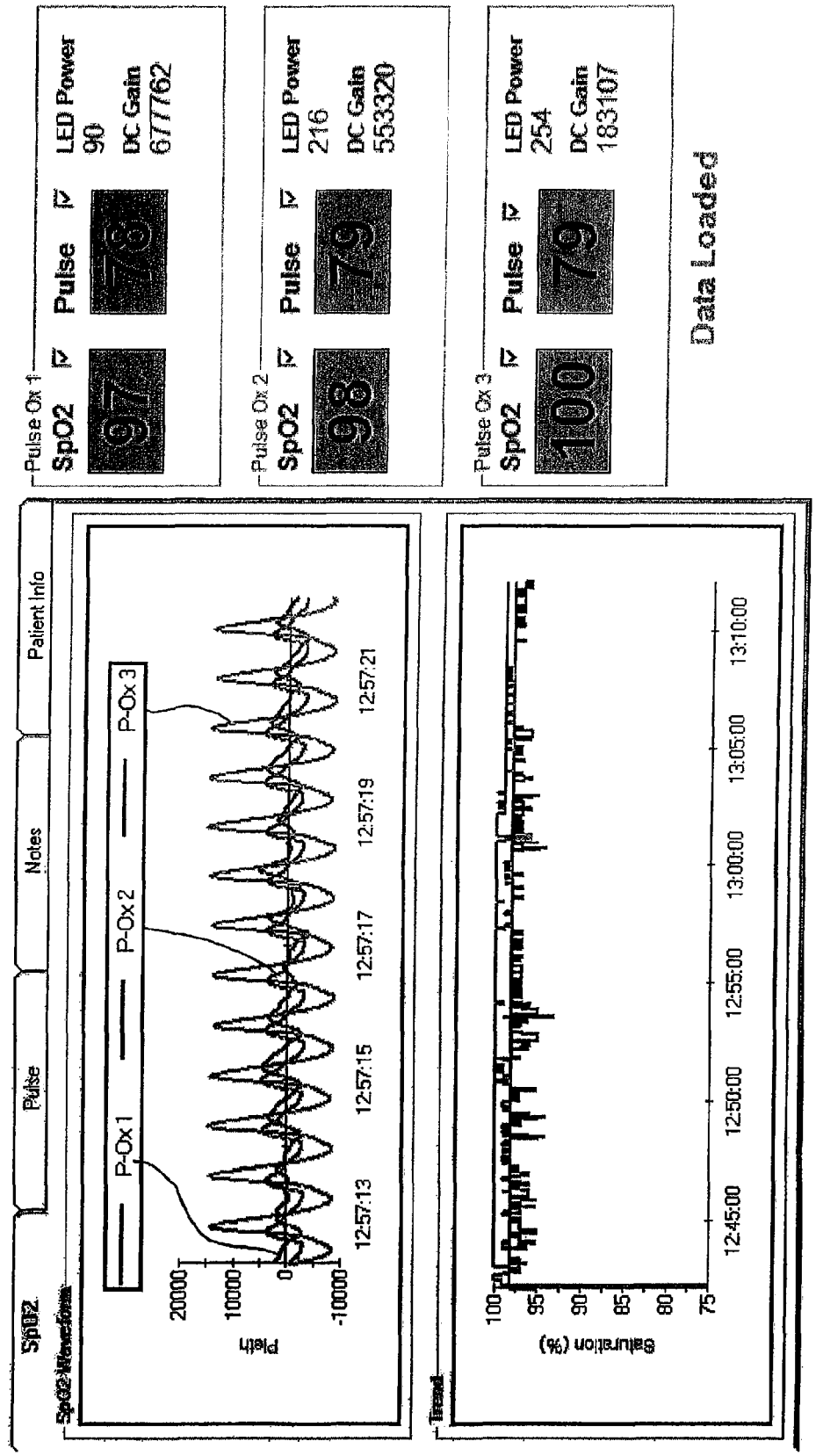

FIG. 16A-C provides photoplethysmographic and arterial blood oxygenation data from a patient who was undergoing coronary artery bypass surgery. Pulse oximeter probes of the present invention were placed in the nose and in the mouth (a cheek/lip probe), and a conventional probe was placed on a finger. FIG. 16A shows typical plethysmographic data from all three probes prior to the switching to bypass. This figure also indicates that the blood oxygenation as measured by all three probes were similar, as were the plethysmograph curves.

FIG. 16B shows data from about one minute after cardiac activity was reinitiated and the blood flow and pressure returned following bypass, but during a low flow condition (which was done to repair a tear in the aorta). This demonstrates that both the nasal and the cheek/lip probes had sufficient blood flow to obtain a plethysmograph and pulse and saturation data, whereas the finger probe did not.

FIG. 16C shows data near the end of the surgical procedure, when blood flow had returned to normal. All three sites are provided readable data. Also, although the plethysmographic data from the finger site appears stronger (i.e., the peak is higher), it should be kept in mind that this is the result of algorithms in the pulse oximeter that automatically adjust power and gain.

Figure 17A:
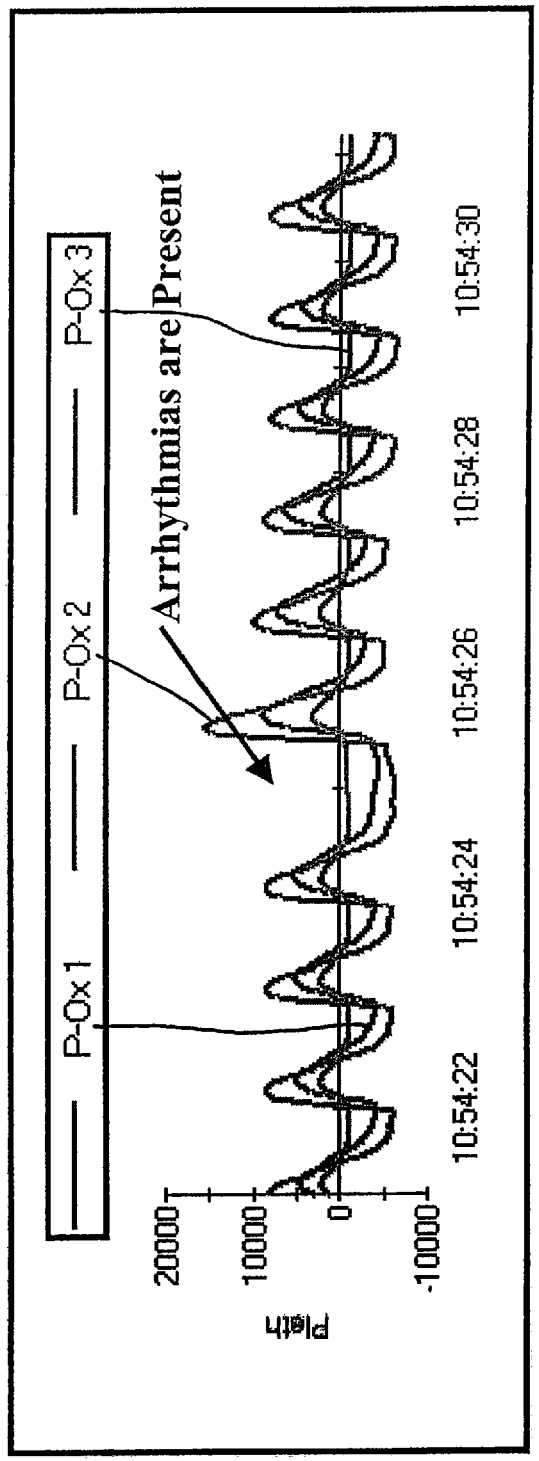
FIGS. 17A-C display data from three different volunteer subjects, all of whom, during a surgical procedure, experienced arrhythmias that were detected differentially by the three probes being evaluated and compared (one at the nasal interior septum, one at the cheek/lip, and one at the finger).
Figure 17B:
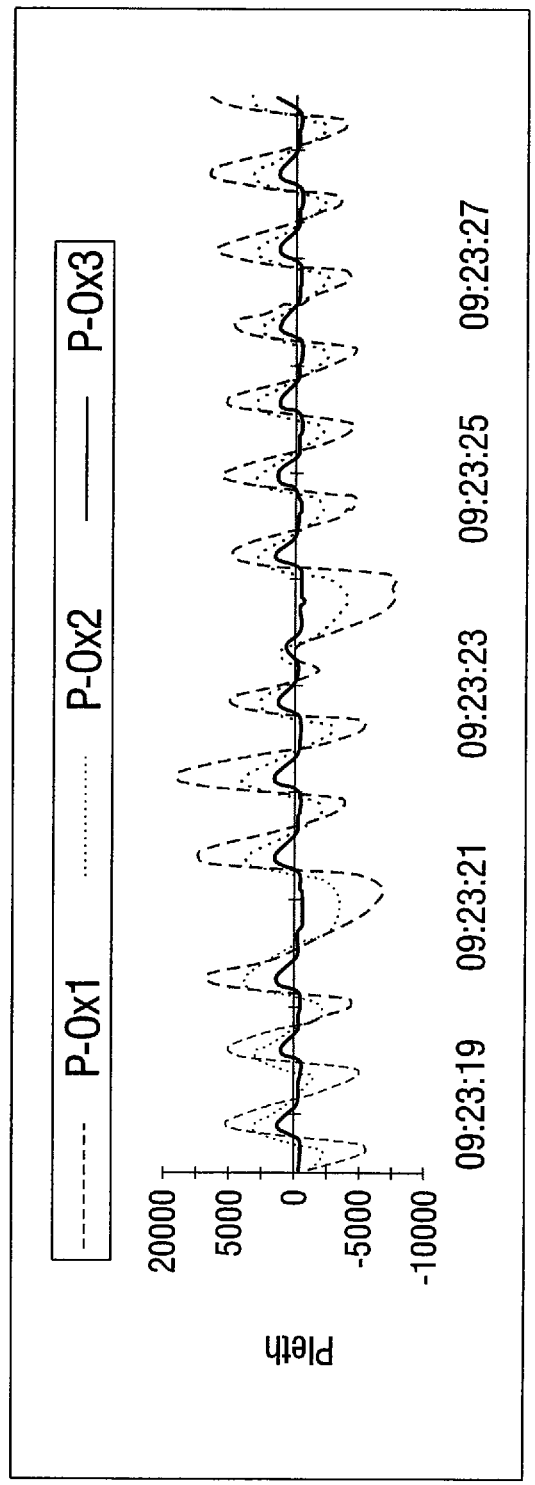
Figure 17C:
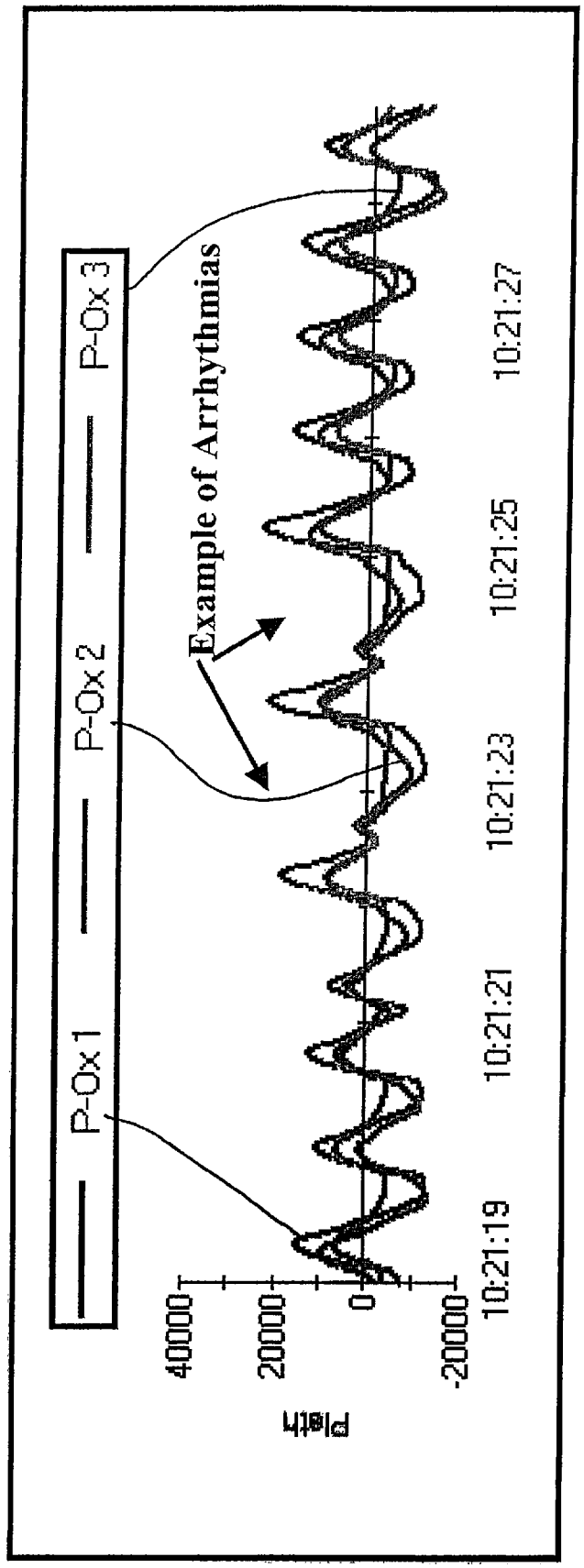
Figure 17D:
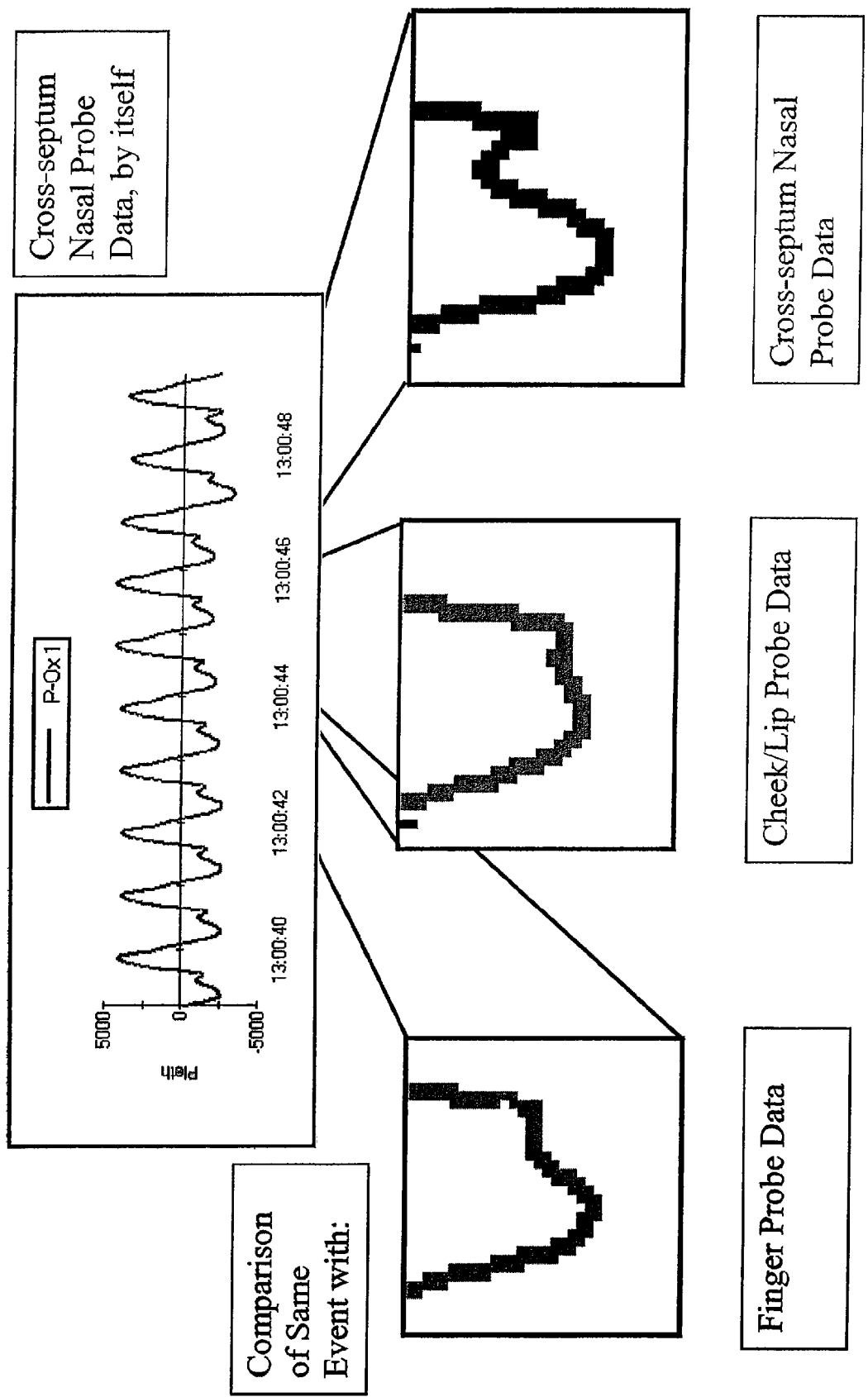
FIG. 17D provides a comparison of the three probes in their ability to detect a dicrotic notch.

FIGS. 17A-C provide data from three different patients, all of which experienced cardiac arrhythmias at some time during the observation period. In all three examples, the nasal probe and the cheek/lip probe provided clearer imaging of the arrhythmias than the finger probe. Also, as observable in FIG. 17D, taken from a fourth patient, the nasal probe most distinctly detected what appears to be a dicrotic notch (compared with the cheek/lip and finger probes). Also, it obtained this data with relatively low energy being supplied to the LED.

Also, during testing with certain patients, given increased sensitivity from the nasal probe, it was observed that respiratory rate can be accurately measured from the nasal photoplethysographs since the nasal probe is more sensitive to volume changes. That is, changes in the "envelope" of the plethysmograph DC component indicates the breathing cycle, and this, upon quantification of these cycles, can estimate respiratory rate. One example of this is provided in FIG. 18a, where the space between the two vertical lines represents one respiration cycle.

Use of the nasal or cheek probes independently or in conjunction with the finger probe can also be used to evaluate the effects on cardiac output, blood pressure and perfusion in spontaneously breathing and mechanically ventilated patients. For instance, when a normal subject breathes spontaneously, there is little or no observable effect on the plethysmograph from a finger probe. However, both the nasal and cheek probes demonstrate a drop in the "envelope" of the plethysmograph. This is explained by an increase in venous return to the right side of the heart and a decrease in blood flow from the left ventricle due to negative pressure relative to atmospheric pressure produced in the thoracic cavity during normal breathing. This fall in the "envelope" of the plethysmograph is exaggerated during spontaneous breathing against resistance, such as pulmonary diseases that narrow the airways and during hypovolemia or low cardiac output. In addition to the fall in the "envelope" of the plethysmograph, there is often a decrease in the maximum amplitude of the plethysmograph, which becomes more pronounced (a greater decrease) with hypovolemia, poor cardiac output or poor perfusion. Comparing the nasal or cheek plethysmographs with the finger plethysmograph may be an additional means to follow these effects over time.

During mechanical ventilation, changes opposite to those observed with spontaneous breathing occur in both the "envelope" of the plethysmograph and the amplitude. Positive pressure ventilation increases intrathoracic pressure, which in turn increases blood flow from the left ventricle and results in a rise above baseline in the "envelope" and an increase in the amplitude of the plethysmograph. Hypovolemia and/or poor cardiac output diminish these salutary effects. FIGS. 18A-C demonstrate the effects of positive pressure ventilation on increasing vasodilatation or hypovolemia, such as seen during anesthesia. In FIG. 18A each positive pressure ventilation results in a rise in the plethysmograph "envelope". In FIGS. 18B and C there are great excursions in the plethysmograph as the patient becomes vasodilated and the amplitude of the plethysmograph decreases.

Further, evaluation of the plethysmograph during both spontaneous and mechanical ventilation can be used to determine the optimal level of positive end expiratory pressure (PEEP) for a patient. PEEP is an important parameter for optimizing the oxygenation of a patient. Depending on the volume and cardiac status of a patient, different levels of PEEP can be tolerated. Since a higher PEEP raises the baseline intrathoracic pressure, it impedes venous return to the heart and can cause decreased cardiac output. If a subject is hypovolemic, vasodilated or has poor cardiac output, excessive PEEP may lead to hypotension, lactic acidosis and eventually shock. If inadequate PEEP is given, the patient will be hypoxemic, which can also lead to lactic acidosis and shock. Thus, there is an optimal PEEP for each subject depending on his or her pulmonary, volume and cardiac status. Excessive PEEP narrows the amplitude of the plethysmograph and causes exaggerated excursions in the "envelope" of the plethysmograph.

Evaluation of the "envelope" of the plethysmograph and the effects of ventilation on the amplitude of the plethysmograph can be used to provide a level of PEEP that allows adequate oxygenation without compromising cardiac output. If oxygenation remains poor at a given level of PEEP, volume expansion with fluids and/or drug treatment can improve cardiac output and allow the patient to tolerate the higher level of PEEP. Evaluation of the plethysmograph provides a non-invasive means of determining the effects of positive pressure ventilation and PEEP on the cardiac output of the patient.

It is noted that an appreciation of data obtainable from pulse oximetry probes is found in the scientific article, "The peripheral pulse wave: information overlooked," W. B. Murray and P. A. Foster, J. Clin. Monitoring 12:365-377, 1996. This reference discusses in detail the bases for changes in the wave form obtainable from pulse oximeter peripheral probes, and the significance of changes in such wave forms during anesthesia. All material in this reference is hereby particularly incorporated by reference into this disclosure. Further, it is noted that this reference focused on the use of the ear, or peripheral locations, and so did not fully appreciate the types and improved quality of data obtainable from a desired vascular site of the interior nasal septum, or from the cheek/lip probe, as described herein. Also, it is appreciated that the probes of the present invention find utility not only in patients who are inactive, such as those undergoing anesthesia during surgery, but also in patients who are awake and, selectively, ambulatory.

Thus, as observable from the above figures, the use of a nasal probe of the present invention, which does not require pressure against the septum wall to operate, advantageously provides photophethysmographic data that is able to detect cardiac, pulmonary, and other abnormalities non-invasively, and better than more remote sites, such as a finger or a toe. While not being bound to a particular theory, this is believed due to the combination of: 1) not applying pressure to the vascularized site (thereby not damping more subtle signals of heartbeat patterns, etc.); 2) accessing an arterial bed supplied by a major vessel, the internal carotid artery; and 3) accessing this arterial bed in a position that is not subject to additional noise and dampening (as is found in extremity sites, such as the finger or toe).

EXAMPLE 9

In many instances when pulse oximetry is being used to detect, for instance, arterial blood oxygen saturation, and/or, when plethysmography is being used to detect other cardiovascular parameters, there also is a desire or need to measure carbon dioxide during exhalation, particularly the end tidal carbon dioxide of the patient. It is recognized, for instance, that monitoring the carbon dioxide during the exhalation cycle more quickly detects airway obstruction than pulse oximetry, and, where there is an endotracheal intubation, provides the most reliable indicator of proper intubation. A graph of the concentration of carbon dioxide in exhaled gas plotted over time is referred to as a capnogram. An instrument capable of displaying only end tidal values is called a capnometer, while an instrument capable of graphically displaying end tidal carbon dioxide is called a capnograph. The shape of the capnogram reveals information about the integrity of a breathing system and the physiology of the patient's cardiorespiratory system. As such, capnography is the preferred method of end tidal carbon dioxide monitoring.

Accordingly, another aspect of the present invention is the combination of the nasal pulse oximeter of the present invention with sampling structures that direct exhaled gas for carbon dioxide measurements to provide data for either a capnometer or a capnograph.

Figure 19A:
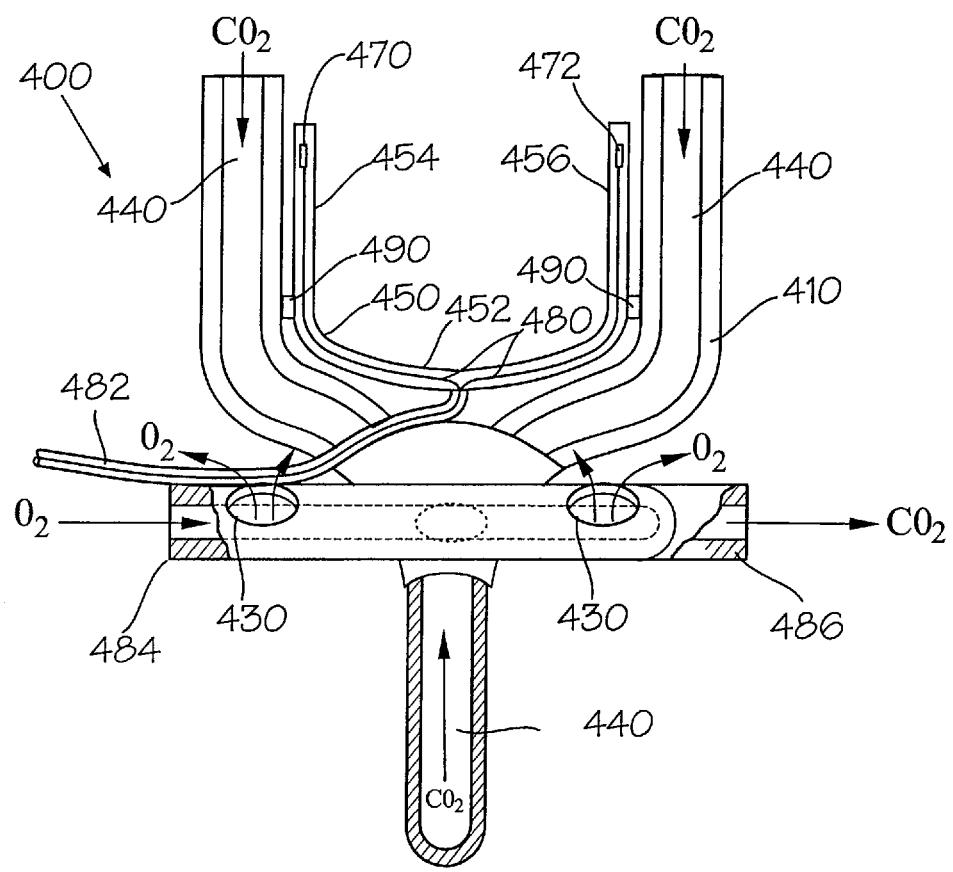
FIG. 19A is a plan/cut-away view of a nasal probe of the present invention in combination with a known design of a capnography sampling/oxygen supply device.

For instance, and not to be limiting, FIG. 19A depicts a combination pulse oximeter/cannula/carbon dioxide sampler, 400. Here the body of nasal probe, 450, is substantially comprised of extensions, 454 and 456, each sized to enter the nares, and integrally molded main section, 452, and is joined with a cannula/carbon dioxide sampler, 410, that is designed in accordance with U.S. Pat. No. 6,422,240 B1, issued Jul. 23, 2002. One of the extensions, 454 comprises the light-generating components (not specifically shown, but within 470 and including structures such as LEDs 62 and 64 in FIG. 2A-D). The other extension, 456, comprises a light detecting component(s) (not specifically shown, but within 472 and including structures such as photodetector 66 in FIG. 2A-D). Connecting wiring, 480, passes between the light-generating and light-detecting components and the pulse oximeter itself, and passes through a wire conduit, 482, that selectively travels contiguously for a length with either the oxygen supply tube, 484, or the carbon dioxide sampling tube, 486 (shown in FIG. 19A traveling with the oxygen supply tube, 484). Attaching means, 490, join the nasal probe, 450, with the structure of the cannula/carbon dioxide sampler, 410, and may be of any type known in the art, including, but not limited to: adhesive (i.e., plastic glue, thermoplastic glue), double-sided tape, and the like.

In operation, oxygen from a supply source (not shown), delivered via oxygen supply tube 484, is released at the apertures, 430, in front of the patient's nose and above the patient's mouth (seen better in FIG. 19B), and upon inhalation, some of this oxygen is taken up and passes to the lungs of the patient. Upon exhalation, whether from nose and/or mouth, exhaled gases are collected in one or more of the three intake ports, 440 (two nasal, one oral). The exhaled gases are collected and passed through the tube, 486, to a carbon dioxide detector (not shown). At the same time that this repeatedly occurs, advantageously, pulse oximeter data is collected by the nasal probe, 450, by the means described elsewhere in this disclosure. This data, communicated by connecting wiring, 480, is analyzed by a pulse oximeter and the output displayed on an appropriate output monitor (not shown).

Figure 19B:
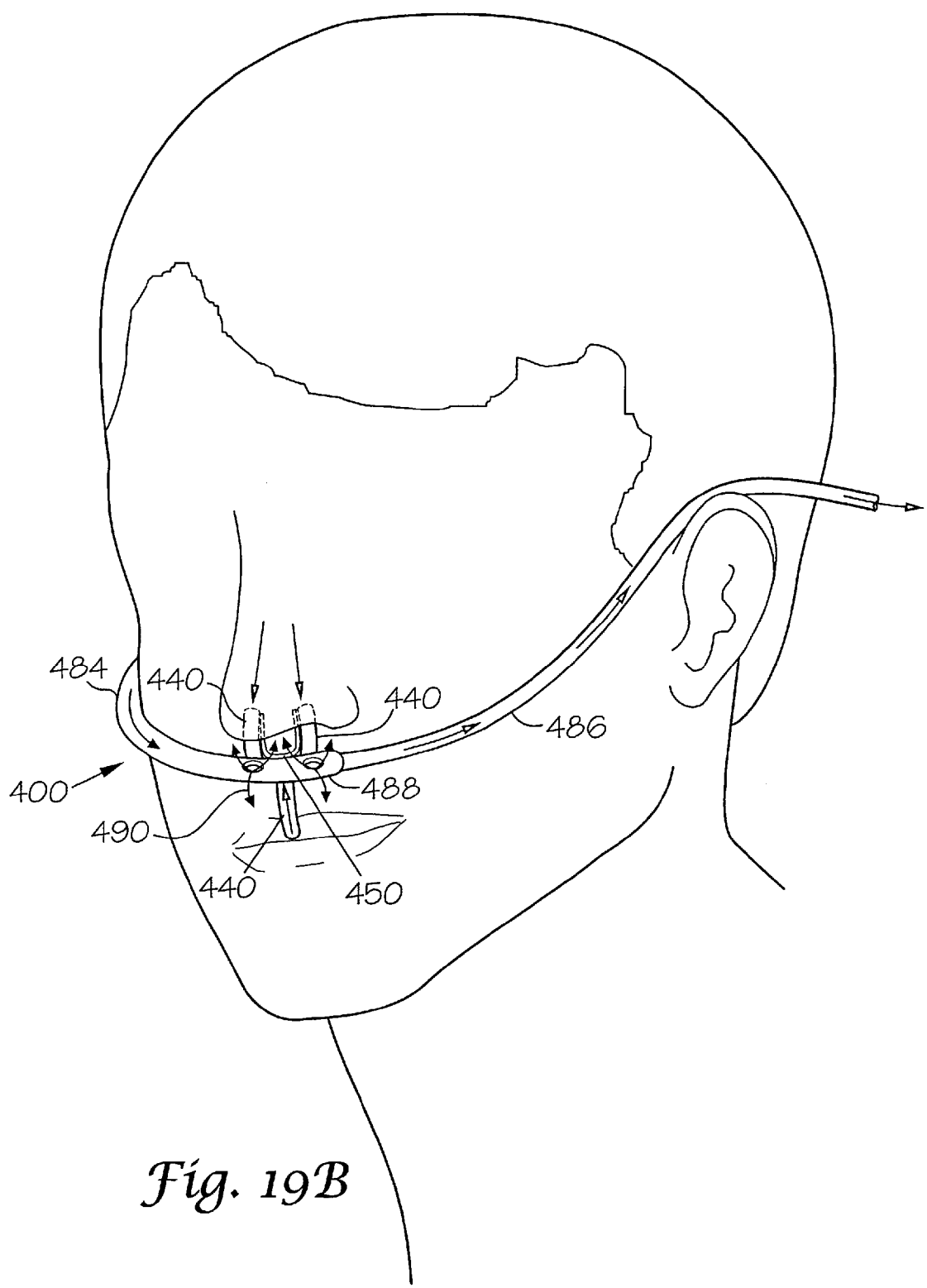
FIG. 19B is a perspective diagrammatic view of an embodiment, in place on a subject, of the combination device depicted in FIG. 19A.

FIG. 19B depicts the combination nasal probe/cannula/carbon dioxide sampler, 400 positioned on the face of a patient. Arrows 490 depict the flow of oxygen from a dual-gas manifold, 488, which directs oxygen received from the oxygen supply tube, 484. During exhalation, the exhaled breath gases, which include carbon dioxide, are collected from the intake ports, 440, one in the mouth (to collect when a patient is "mouth breathing"), and one from each nostril. The nasal pulse oximeter probe, 450, is secured along the top edge of the manifold, 488, and along the adjacent sides of the tube wall of the two nasal intake ports, 440. Details of the nasal pulse oximeter probe, 450, are observable in FIG. 19A.

EXAMPLE 10

As for the combinations described above for the nasal probe, the lip/cheek probe of the present invention also is combined with 1) a carbon dioxide sampling device, 2) a source of oxygen or oxygen-rich gas; or 3) both of these.

Figure 20:
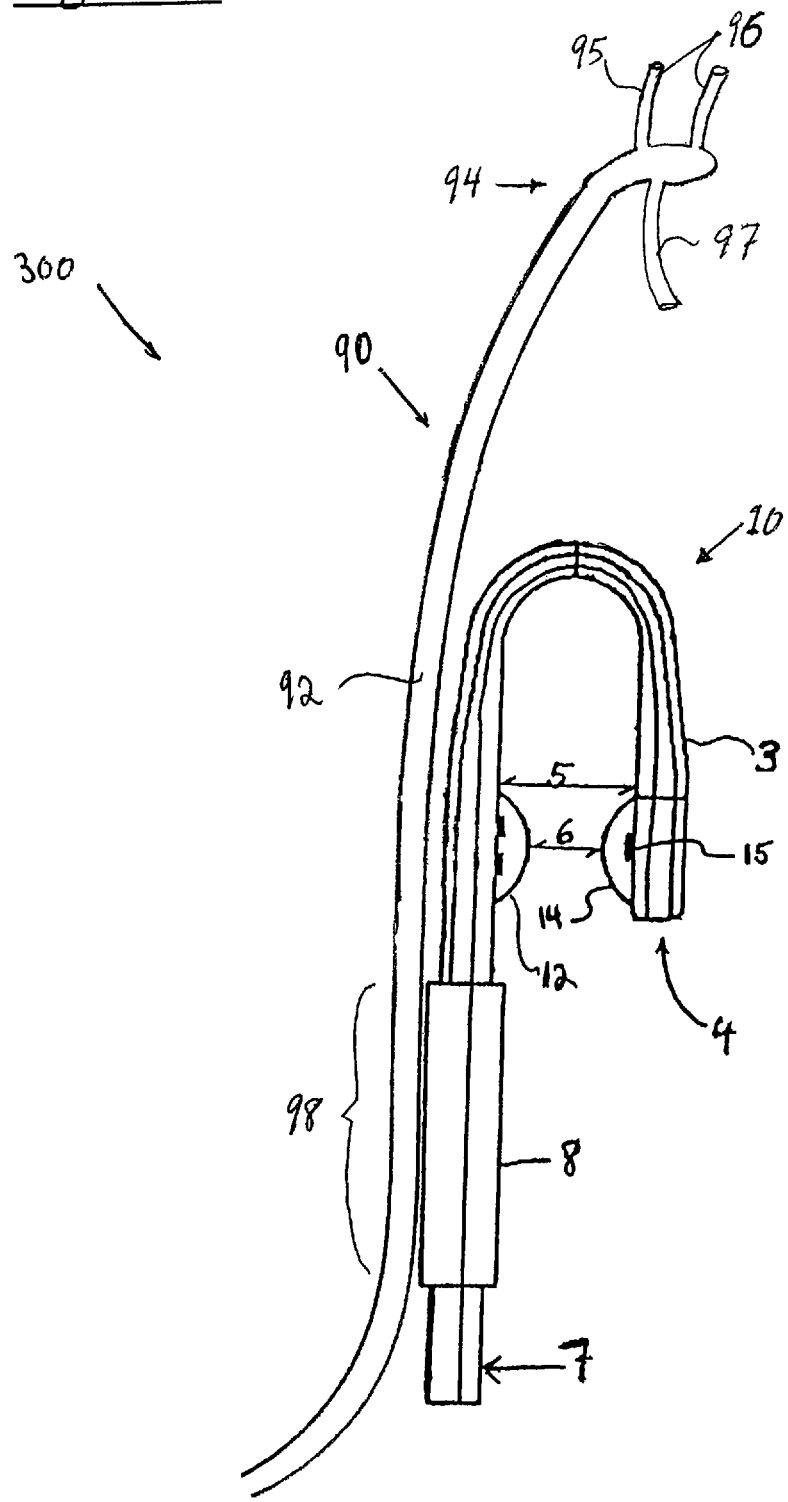
FIG. 20 is a side view of a lip/cheek in combination with a design of a capnography sampling/oxygen supply device.

For example, and not to be limiting, FIG. 20 depicts one embodiment of a combination of the lip/cheek probe of FIG. 1, 10, in combination with a carbon dioxide sampler, 90, for use in capnography. A flexible hollow tube, 92, communicates between a three-pronged sampling end, 94, and the actual carbon dioxide detector (not shown). Two upper prongs, 95 and 96, are sized and spaced for insertion into the nares of the nose of the patient (not shown), and one lower prong, 97, is sized for insertion into the mouth of the patient (not shown), or for terminating outside of the mouth of a patient (not shown), to take up sample outside the mouth. A section of the tubing, 98, is adjustably engaged to a corresponding section of the boot, 8. For instance, the distance between the boot, 8, and the three-pronged sampling end, 94, is adjusted so as to be without kinking or torsion, thereby providing for a comfortable fit. The reversible and adjustable engagement of the tubing between this section and the three-pronged sampling end, 94, is effectuated by any means for attaching known in the art, which includes, but is not limited to: hook-and-loop adjoining fabric sections, one or more loops of flexible plastic or other material encircling both the boot, 8, and the section of the tubing, 98, a snap fitting with the snap on the tube, 92, slidably movable along said tube, 92. It is noted that in other embodiments, not shown, the tubing, 92, engages a part of the probe, 10, other than the boot, 8 (such as when the probe, 10, is not comprised of a boot). Such means for attaching the tubing, 92, is present on all sides of the boot (or other part of the probe, 10), or alternatively only on one or more of the sides most likely to be used (i.e., the side situated in an upper position when the probe, 10, is placed so the bridging section, 2, of the probe, 10, is positioned in or near one corner of the mouth, with the cable leading over one ear).

Additionally, the three-pronged sampling end, 94, is taped or otherwise secured to the upper lip, as may be appropriate for a particular patient. In use, the carbon dioxide concentration is measured over time and volume, and one or more capnographs is obtainable. Such combined apparatus has use with persons undergoing sleep studies and other research, and in other applications where oxygen need not be supplied.

The lip/cheek probe also may be combined with a cannula device to provide gas, such as oxygen or an oxygen-rich gas mixture, to a patient in need thereof. For instance, and not to be limiting, the tubing assembly designated as 90 in FIG. 20 alternatively is used to supply oxygen or an oxygen-rich gas mixture to both the nose and mouth area (to accommodate mouth breathing) rather than to sample exhaled breath as described above. More generally, any number of designs of cannula devices as are known in the art are so combined, to supply such gas to the nose, to the mouth, or to both.

Thus, the lip/cheek probe of the present invention may be combined to form a single, operational unit with any other style of oxygen supply/carbon dioxide sampler device, that is, an integral multi-functional device. This provides the advantage of obtaining reliable data, such as for arterial oxygen saturation, while only occupying essentially the same space and path of tubing/wiring, as does the oxygen supply/carbon dioxide sampler device alone. The data from the probe can be integrated with the data from the capnography unit to obtain a better picture of the patient's respiratory and circulatory function and condition. Additionally, as for other types of probes described above, an additional feature is added, namely a control means to adjust the flow rate of the gas that is provided, where such control is directed by the blood oxygen saturation data obtained from the probe.

Although depicted above as separate units combined after production, the combinations described above alternatively are integral units designed and sized such that the lip/cheek probe therein functions as described in this disclosure. Also, protective sleeves, as described for the lip/cheek probe alone, are envisioned to be shaped and manufactured in accordance with the teachings herein, and used for these multi-function devices.

Preferably, the probes and sleeves are easily fabricated from low cost materials and are adaptable for use in an operating room, intensive care unit, emergency department, post-surgery recovery areas and other areas to treat patients in need of hemodynamic monitoring. The monitoring system is particularly applicable for use with patients in whom hypotension or poor perfusion are problematic. In addition, the monitoring system is particularly well suited for use with multi-trauma and thermally injured patients who either have severe peripheral vasoconstriction or have severely damaged or destroyed peripheral vascular beds. Through combining at least two pulse oximeters capable of measuring desired parameters at at least two locations into a single monitor system, the present invention provides a more accurate assessment of perfusion and resistance in patients, than any of the presently available single probe pulse oximeters.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A photoplethysmography probe comprising
(a) at least one light source and at least one photodetector;
(b) a co-fabricated structure that comprises a first substantially flattened side and a second substantially flattened side connected by a resilient section of plastic, each side comprising an inner face and an outer face, wherein said inner face of said first substantially flattened side opposes said inner face of said second substantially flattened side; and
(c) a first sleeve and a second sleeve, each comprising a stretchable aspect of one or more parts, or of the entire sleeve, wherein said first sleeve is stretched over a protrusion or prominence of said first substantially flattened side and said second sleeve is stretched over a protrusion or prominence of said second substantially flattened side.

2. The probe of claim 1, wherein the light source is an LED.

3. The probe of claim 1, wherein said photoplethysmography probe is configured to secure to a tissue of an individual's right or left nasal alar.

4. The probe according to claim 1, wherein said probe further comprises one or more other monitoring sensors configured to determine respiratory parameters.

5. The photoplethysmography probe of claim 4, wherein said one or more other monitoring sensors are configured to detect nasal air flow and/or nasal pressure.

6. The photoplethysmography probe of claim 1, wherein a ratio of a height to the greater of a length or a width of said first substantially flattened side is between about 0.2:1 and 0.001:1 and a ratio of a height to the greater of a length or width of said second substantially flattened side is between about 0.2:1 and 0.001:1.

7. The photoplethysmography probe of claim 1, wherein (a) the first sleeve encloses said at least one light source; and/or (b) said second sleeve encloses said at least one photodetector.

8. The photoplethysmography probe of claim 1, wherein (a) the first sleeve bears said at least one light source; and/or (b) said second sleeve bears said at least one photodetector.

9. A method for monitoring an individual, said method comprising:
securing at least one photoplethysmography probe of claim 1 onto said individual's right and/or left nasal alar; and
obtaining photoplethysmography signals generated by said at least one plethysmography probe.

10. The method of claim 9, further comprising:
(a) monitoring said photoplethysmography signals over time, and/or
(b) using said photoplethysmography signals to obtain at least one blood oxygen saturation measurement.

11. The method of claim 9, further comprising any one or a combination of:
(a) using said photoplethysmography signals to diagnose and/or monitor a clinical condition in said individual;
(b) using said photoplethysmography signals to monitor blood flow at a nasal alar site in said individual;
(c) using said photoplethysmography signals to obtain at least one blood pressure measurement and/or a pulse rate for said individual; and
(d) using said photoplethysmography signals to monitor changes in vascular perfusion and/or resistance in said individual.

12. The method of claim 9, wherein tissue of said right and/or left nasal alar is between said at least one light source and said at least one photodetector.

13. The method of claim 9, further comprising:
(a) obtaining breath measurements of said individual from at least one other monitoring sensor; and/or
(b) supplying oxygen or oxygen-rich gas to said individual.

14. The method according to claim 9, said method further comprising:
delivering oxygen or an oxygen-rich gas to said individual;
obtaining photoplethysmography signals generated by said at least one photoplethysmography probe; and
adjusting at least one parameter selected from flow rate, pressure, concentration and/or amount of said oxygen or said oxygen-rich gas in response to said photoplethysmography signals.

15. The method according to claim 14 wherein any one or a combination of the following applies:
(a) tissue of said right and/or left nasal alar is between said at least one light source and said at least one photodetector;
(b) said oxygen or oxygen-rich gas is delivered to said individual via a self-contained breathing apparatus;
(c) said oxygen or oxygen-rich gas is provided to said individual via mechanical ventilation; and
(d) said oxygen or said oxygen rich gas is provided via PEEP, wherein said PEEP is adjusted in response to said photoplethysmography signals.

16. The method of claim 15, wherein any one or a combination of the following applies:
(a) said self-contained breathing apparatus is used by an emergency worker;
(b) said at least one probe is combined with or part of said self-contained breathing apparatus;
(c) said oxygen or oxygen-rich gas is provided via mechanical ventilation and PEEP;
(d) PEEP is adjusted in response to an amplitude of said photoplethysmography signals; and
(e) PEEP is adjusted in response to an envelope of said photoplethysmography signals.

17. A system for obtaining photoplethysmography data from an individual, said system comprising at least one photoplethysmography probe comprising:
  (a) at least one light source and at least one photodetector;
  (b) a co-fabricated structure that comprises a first substantially flattened side and a second substantially flattened side connected by a resilient section of plastic, each side comprising an inner face and an outer face, wherein said inner face of said first substantially flattened side opposes said inner face of said second substantially flattened side; and
  (c) a first sleeve and a second sleeve, each comprising a stretchable aspect of one or more parts, or of the entire sleeve, wherein said first sleeve is stretched over a protrusion or prominence of said first substantially flattened side and said second sleeve stretched over a protrusion or prominence of said second substantially flattened side.

18. The system of claim 17, wherein the system is configured to process photoplethysmography data from said at least one photoplethysmography probe to measure or monitor any one or a combination of the following:
  (a) blood oxygen saturation levels;
  (b) blood flow;
  (c) photoplethysmography signals over time;
  (d) a clinical condition in said individual;
  (e) blood pressure and/or pulse rate; and
  (f) changes in vascular perfusion and/or resistance in said individual.

19. The system of claim 17, wherein said at least one photoplethysmography probe is configured to secure to a tissue of an individual's right and/or left nasal alar.

20. The system of claim 19 further comprising at least one probe comprising at least one light source and at least one photodetector that is configured to secure onto at least one non-alar site on said individual.

21. The system of claim 20, wherein any one or a combination of the following applies:
  (a) said at least one non-alar site comprises a finger and/or a toe;
  (b) said system is further configured to monitor said right and/or left nasal alar photoplethysmography signals and said at least one non-alar site photoplethysmography signals over time;
  (c) said system is further configured to use said right or left nasal alar photoplethysmography signals and said at least one non-alar site photoplethysmography signals to diagnose a clinical condition in said individual;
  (d) said system is further configured to use said right and/or left nasal alar photoplethysmography signals and said at least one non-alar site photoplethysmography signals to monitor a clinical condition in said individual; and
  (e) said system is further configured to use said right or left nasal alar photoplethysmography signals and said at least one non-alar site photoplethysmography signals to monitor changes in vascular perfusion and/or resistance in said individual.

22. The system of claim 17, wherein said system is further configured
  to obtain breath measurements of said individual from at least one other monitoring sensor.

23. The system of claim 17, wherein
  said at least one probe is unitary with one or more other monitoring sensors configured to determine respiratory parameters.

24. The system of claim 17, said system further comprising:
  a structure configured to deliver oxygen or an oxygen-rich gas to said individual; and
  wherein the system is configured to adjust at least one parameter selected from flow rate, pressure, concentration and/or amount of said oxygen or said oxygen-rich gas in response to photoplethysmography signals generated from said at least one photoplethysmography probe.

25. The system of claim 24, wherein any one or a combination of the following applies:
  (a) said at least one probe is configured such that tissue of said right and/or left nasal alar is between said at least one LED and said at least one photodetector;
  (b) said system is configured such that said oxygen or oxygen-rich gas is delivered to said individual via a self-contained breathing apparatus;
  (c) said system of configured such that said oxygen or oxygen-rich gas is provided to said individual via mechanical ventilation; and
  (d) said system if configured such that said oxygen or said oxygen rich gas is provided via PEEP, wherein said PEEP is adjusted in response to said photoplethysmography signals.

26. The system of claim 25, wherein any one or a combination of the following applies:
  (a) said self-contained breathing apparatus is configured to be used by an emergency worker;
  (b) said at least one probe is combined with or part of said self-contained breathing apparatus;
  (c) said system is configured so that said oxygen or oxygen-rich gas is provided via mechanical ventilation and PEEP;
  (d) said system is configured so that PEEP is adjusted in response to an amplitude of said photoplethysmography signals; and
  (e) said system is configured so that PEEP is adjusted in response to an envelope of said photoplethysmography signals.

27. The system of claim 17, wherein said system is configured to calculate a blood oxygen saturation level in said individual.

28. The system of claim 27, wherein said system is configured to increase or decrease a flow of oxygen to said individual based on said blood oxygen saturation level.

* * * * *